(12) United States Patent
Horn et al.

(10) Patent No.: US 7,700,356 B2
(45) Date of Patent: Apr. 20, 2010

(54) SYSTEM FOR GENE TARGETING AND PRODUCING STABLE GENOMIC TRANSGENE INSERTIONS

(75) Inventors: Carsten Horn, Berlin (DE); Alfred M. Handler, Gainesville, FL (US)

(73) Assignee: The United States of America as represented by the Secretary of Agriculture, Washington, DC (US)

( * ) Notice: Subject to any disclaimer, the term of this patent is extended or adjusted under 35 U.S.C. 154(b) by 549 days.

(21) Appl. No.: 10/534,226

(22) PCT Filed: Nov. 7, 2003

(86) PCT No.: PCT/US03/35587

§ 371 (c)(1),
(2), (4) Date: May 6, 2005

(87) PCT Pub. No.: WO2004/044150

PCT Pub. Date: May 27, 2004

(65) Prior Publication Data

US 2006/0218652 A1    Sep. 28, 2006

(30) Foreign Application Priority Data

Nov. 8, 2002  (DE) ................ 102 51 918

(51) Int. Cl.
*C12N 15/00* (2006.01)
*C12N 5/06* (2006.01)
*C12N 5/10* (2006.01)
*C07H 21/04* (2006.01)
*C07H 21/02* (2006.01)

(52) U.S. Cl. .............. 435/455; 435/350; 536/23.1
(58) Field of Classification Search ............ 536/23.1; 435/350, 455
See application file for complete search history.

(56) References Cited

U.S. PATENT DOCUMENTS

| 6,218,185 B1 | 4/2001 | Shirk et al. |
| 6,287,863 B1 | 9/2001 | Hodgson |
| 6,551,825 B1 | 4/2003 | Shirk et al. |
| 6,773,914 B1 | 8/2004 | Handler |
| 2002/0094575 A1 | 7/2002 | Suzuki |
| 2006/0212949 A1 | 9/2006 | Alphey |

FOREIGN PATENT DOCUMENTS

WO    WO 01/66717 A2    9/2001

OTHER PUBLICATIONS

Horn and Handler, 2005, Site-specific genomic targeting in *Drosophila*, PNAS< 102:12483-12488.*
Handler, AM et al,, 2004, Post-integration stabilization of a transposon vector by terminal sequence deletion in *Drosophila melanogaster*, Nature Biotechnology, 22:1150-1154.*
Bateman, JR et al, 2006, Site-specific transformation of *Drosophila* via oC31 integ.*
Wimmer, 2005, Nature Methods, 2:580-582.*

* cited by examiner

*Primary Examiner*—Valarie Bertoglio
(74) *Attorney, Agent, or Firm*—John Fado; Albert Y. Tsui; Lesley Shaw

(57) ABSTRACT

The novel germ-line transformation systems disclosed in this patent application allow the physical deletion of transposon DNA following the transformation process, and the targeting of transgene integrations into predefined target sites. In this way, transposase-mediated mobilization of genes-of-interest is excluded mechanistically and random genomic integrations eliminated. In contrast to conventional germ-line transformation technology, our systems provide enhanced stability to the transgene insertion. Furthermore, DNA sequences required for the transgene modification (e.g. transformation marker genes, transposase or recombinase target sites), are largely removed from the genome after the final transgene insertion, thereby eliminating the possibility for instability generated by these processes. The RMCE technology, which is disclosed in this patent application for invertebrate organisms (exemplified in *Drosophila melanogaster*) represents an extremely versatile tool with application potential far beyond the goal of transgene immobilization. RMCE makes possible the targeted integration of DNA cassettes into a specific genomic loci that are pre-defined by the integration of the RMCE acceptor plasmid. The loci can be characterized prior to a targeting experiment allowing optimal integration sites to be pre-selected for specific applications, and allowing selection of host strains with optimal fitness. In addition, multiple cassette exchange reactions can be performed in a repetitive way where an acceptor cassette can be repetitively exchanged by multiple donor cassettes. In this way several different transgenes can be placed precisely at the same genomic locus, allowing, for the first time, the ability to eliminate genomic positional effects and to comparatively study the biological effects of different transgenes.

12 Claims, 18 Drawing Sheets

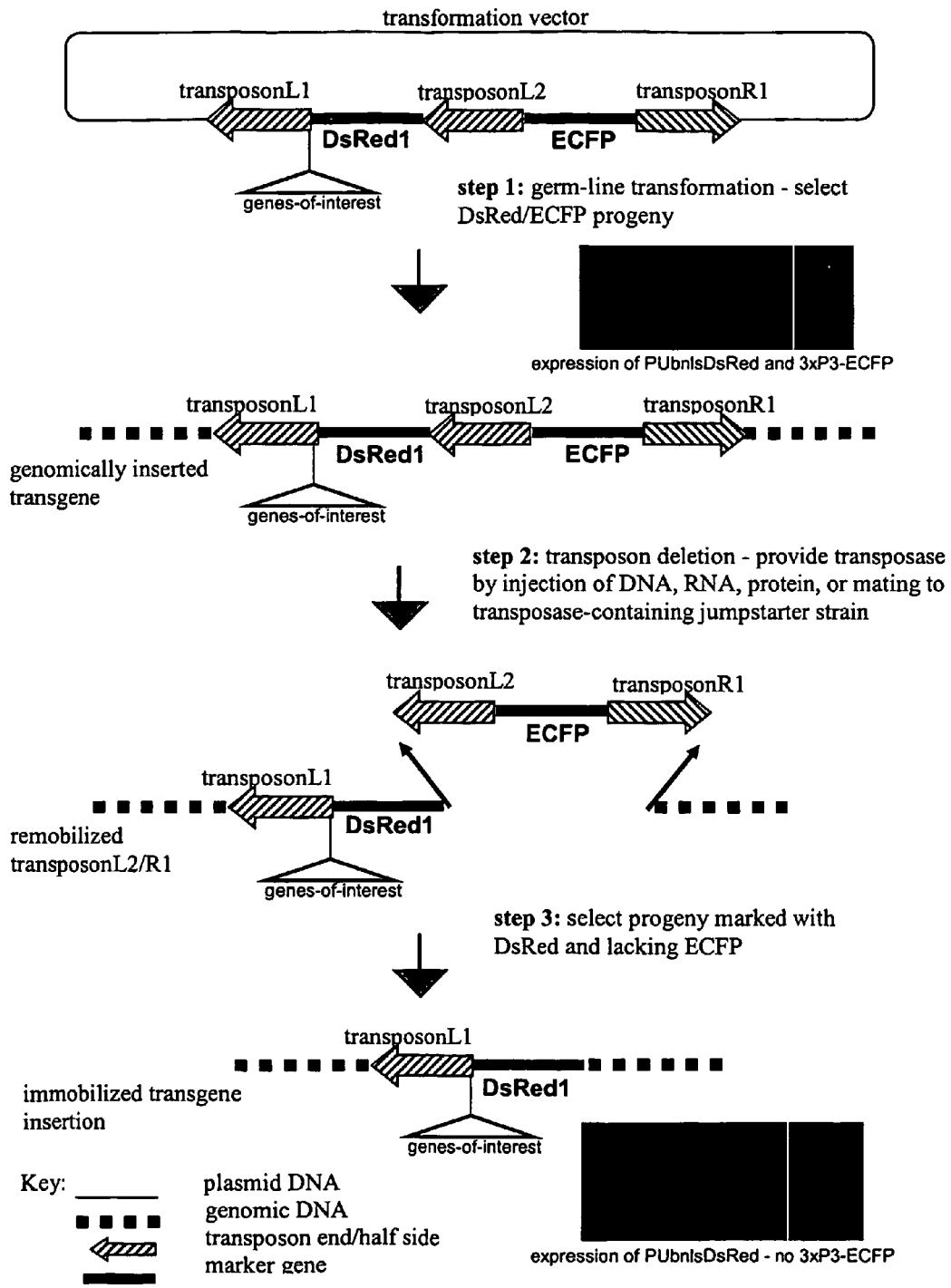

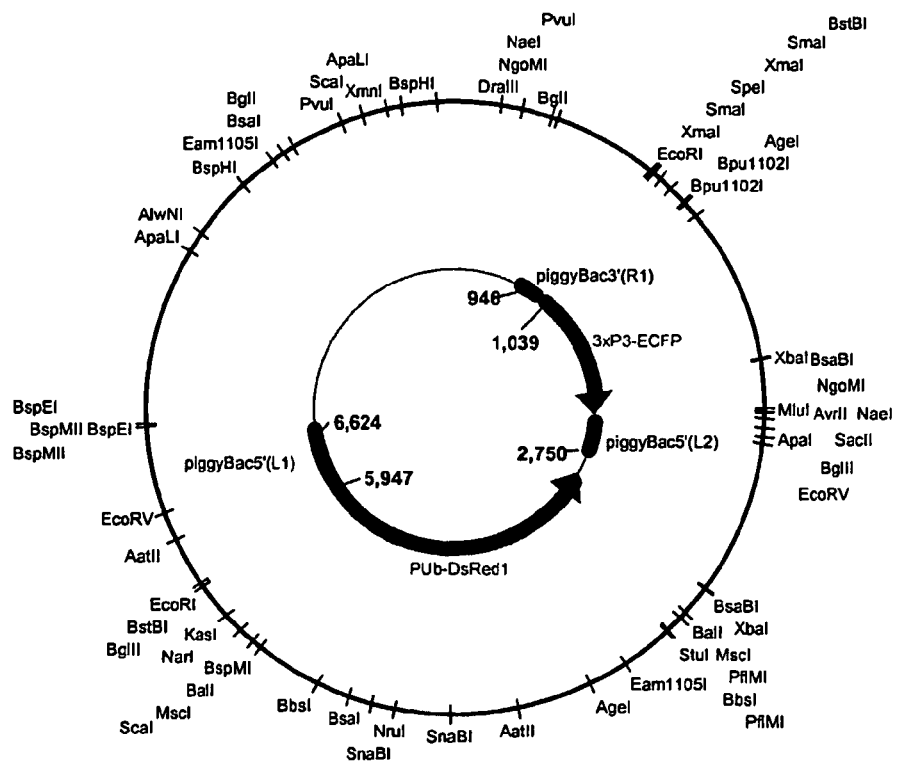
Fig. 2. Diagram of stabilization vector pBac{L1-PUbDsRed1-L2-3xP3-ECFP-R1}
Plasmid size: 9.1 kb
Unique *Kas*I cloning site Figure 3: PCR analysis and verification of pBac{L1-PUbDsRed1-L2-3xP3-ECFP-R1} vector integration in line F34 and L2-3xP3-ECFP-R1 remobilization in line F34-1M PCR Primers:
| 94F pB1-20 | 5'- CCCTAGAAAGATAGTCTGCG-3' |
| 122R pB159 | 5'- ATCAGTGACACTTACCGCATTGACA -3' |
| 139F pB445 | 5'- CCAGAGCGATACAGAAGAAGC -3' |
| 140R pB668 | 5'- TGTTCAGTGCAGAGACTCGG-3' |
| pBL-R | 5'- TATGAGTTAAATCTTAAAAGTCACG -3' |
| pBR-F | 5'- GTTGAATTTATTATTAGTATGTAAGTG -3' |
| 192R ECFP | 5'- AGAAGAACGGCATCAAGGC -3' |
| 193F DsRed | 5'- ACTCCAAGCTGGACATCACC -3' |
| 196R DmX-3' | 5'- CGCAGACGAAGAACAAACAGTA -3' |
| 197F DmX-5' | 5'- GCTGTTTGCTTTGTTGTTGTCAT -3' |

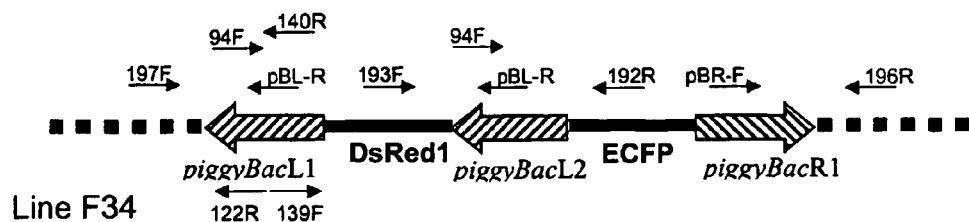

Line F34

| Primer pairs | Predicted (bp) | Obtained (kbp) |
|---|---|---|
| 1- pBR/196 | 237 | 0.2 |
| 2- 193/196 | 2,630 | 2.6 |
| 3- 192/197 | 4,897 | 4.9 |
| 4- 140/197 | 713 | 0.7 |
| 5- pBL/197 | 278 + 4,063 | 0.3 + 4.0 |
| 6- 94/196 | 2,084 + 5,958 | 2.0 |
| 7- 196/197 | 6,003 | 6.0 |

Line F34-1M

| Primer pairs | Predicted (bp) | Obtained (kbp) |
|---|---|---|
| 1- pBR/196 | - | - |
| 2- 193/196 | 624 | 0.6 |
| 3- 192/197 | - | - |
| 4- 140/197 | 713 | 0.7 |
| 5- pBL/197 | 278 | 0.3 |
| 6- 94/196 | 3,952 | 4.0 |
| 7- 196/197 | 3,997 | 4.0 |

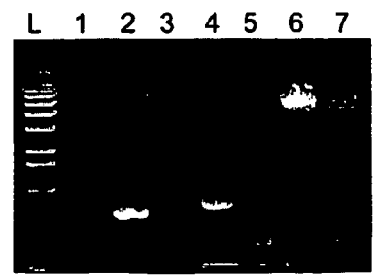

Figure 4: Conditional excision competent transformation vectors
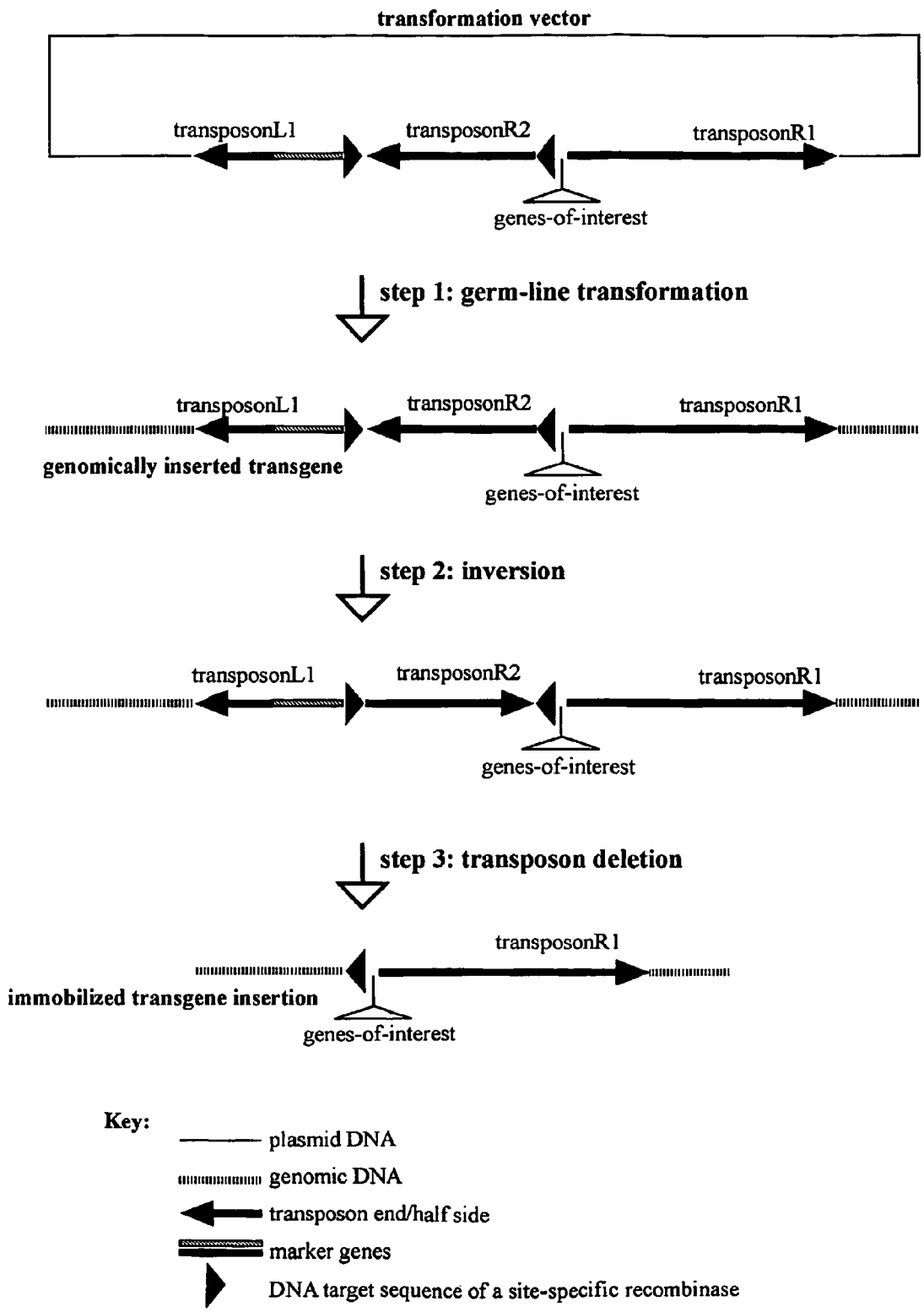

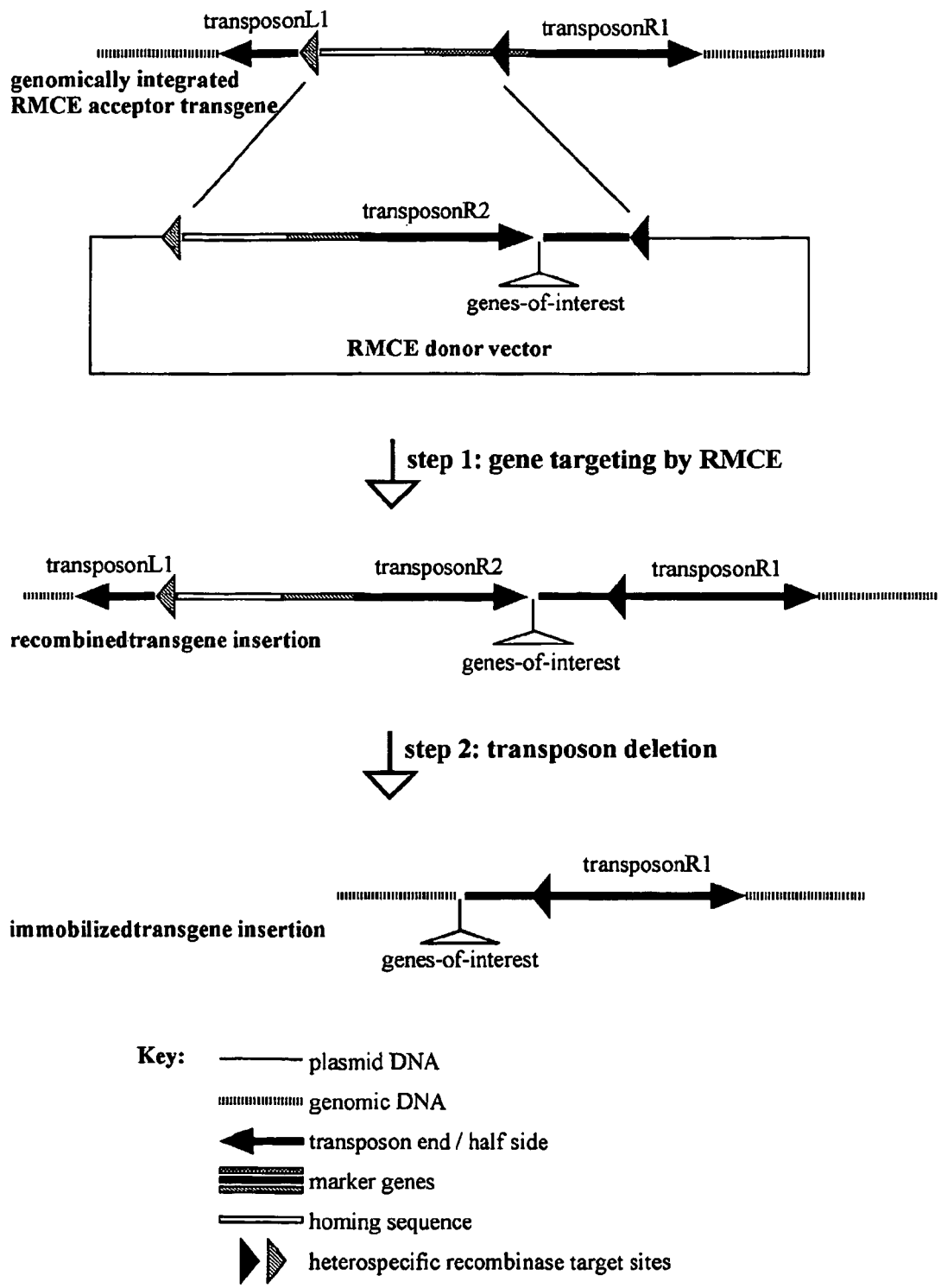
Figure 5: RMCE with subsequent transposon deletion

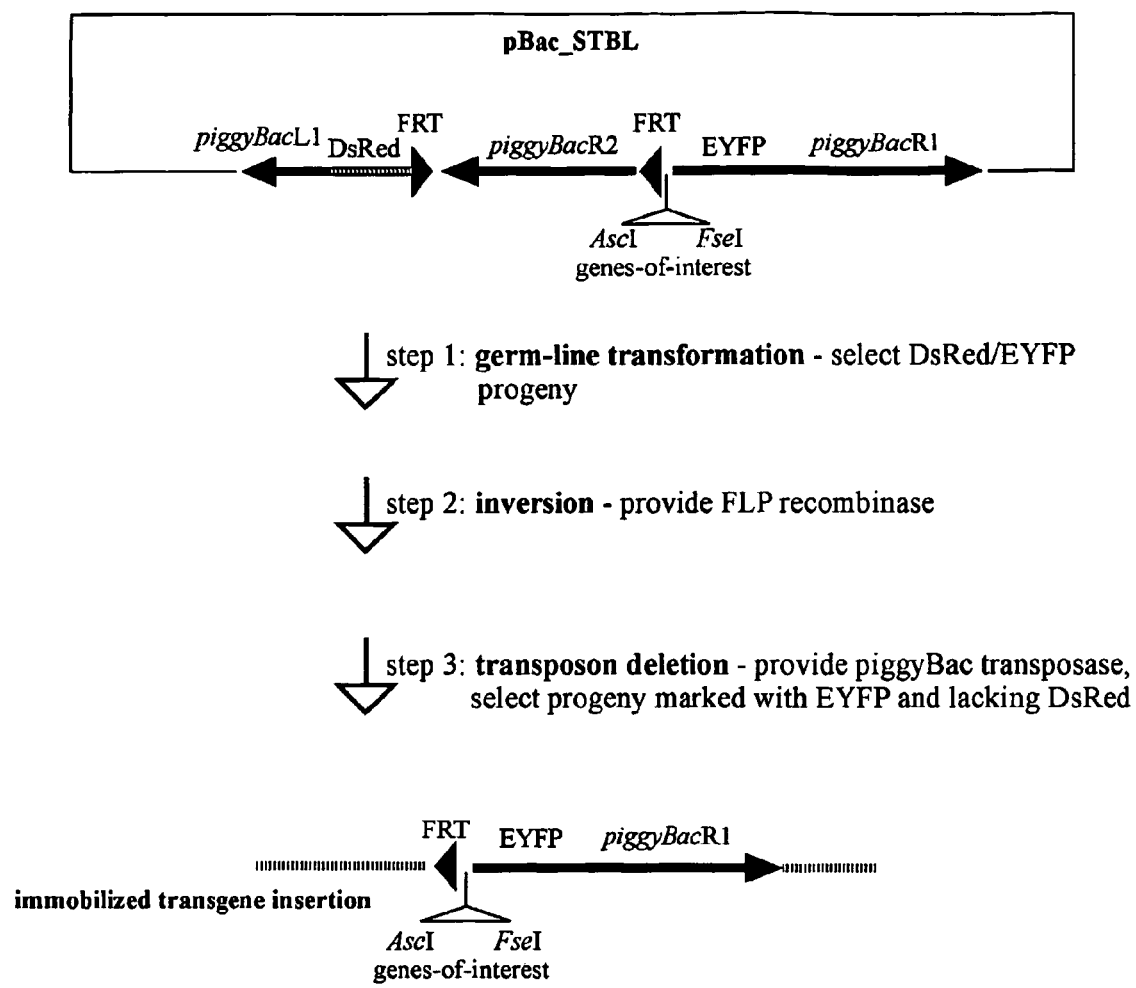
Fig 6: Embodiment: Stabilized vector creation with pBac_STBL (principle shown in Fig. 4)

Fig 7: Embodiment: Stabilized vector creation by RMCE
(principle shown in Fig. 5)
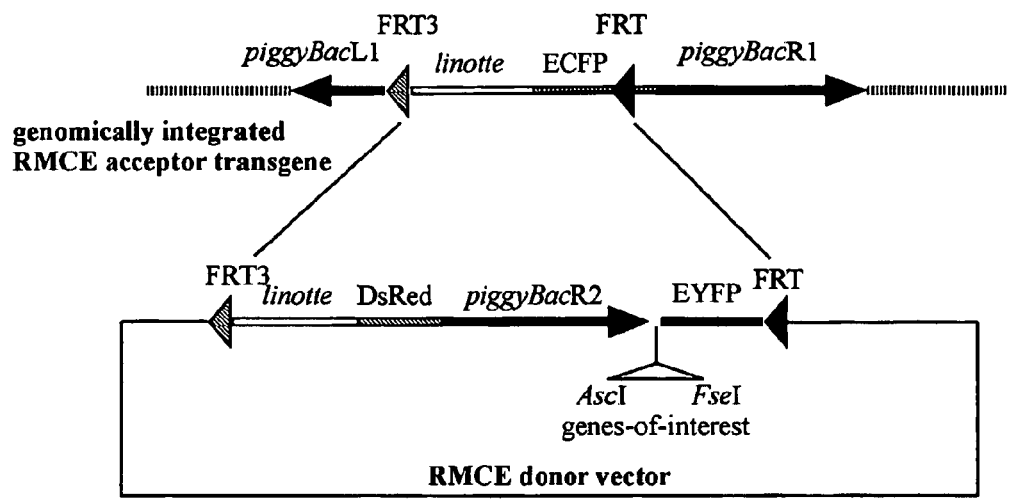
step 1: gene targeting / RMCE - provide *Flp* recombinase,
select progeny with EYFP and DsRed
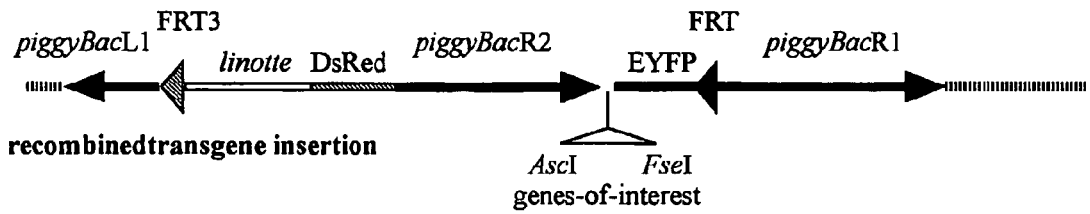
step 2: transposon deletion - provide piggyBac transposase,
select progeny with EYFP and lacking DsRed
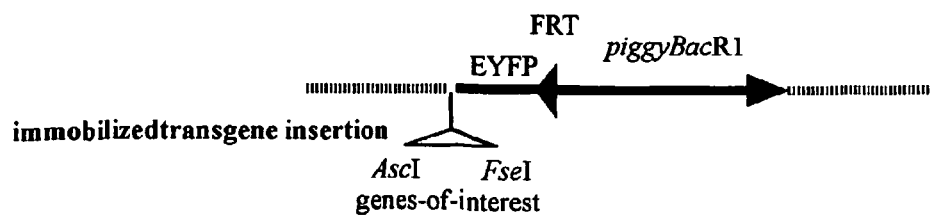

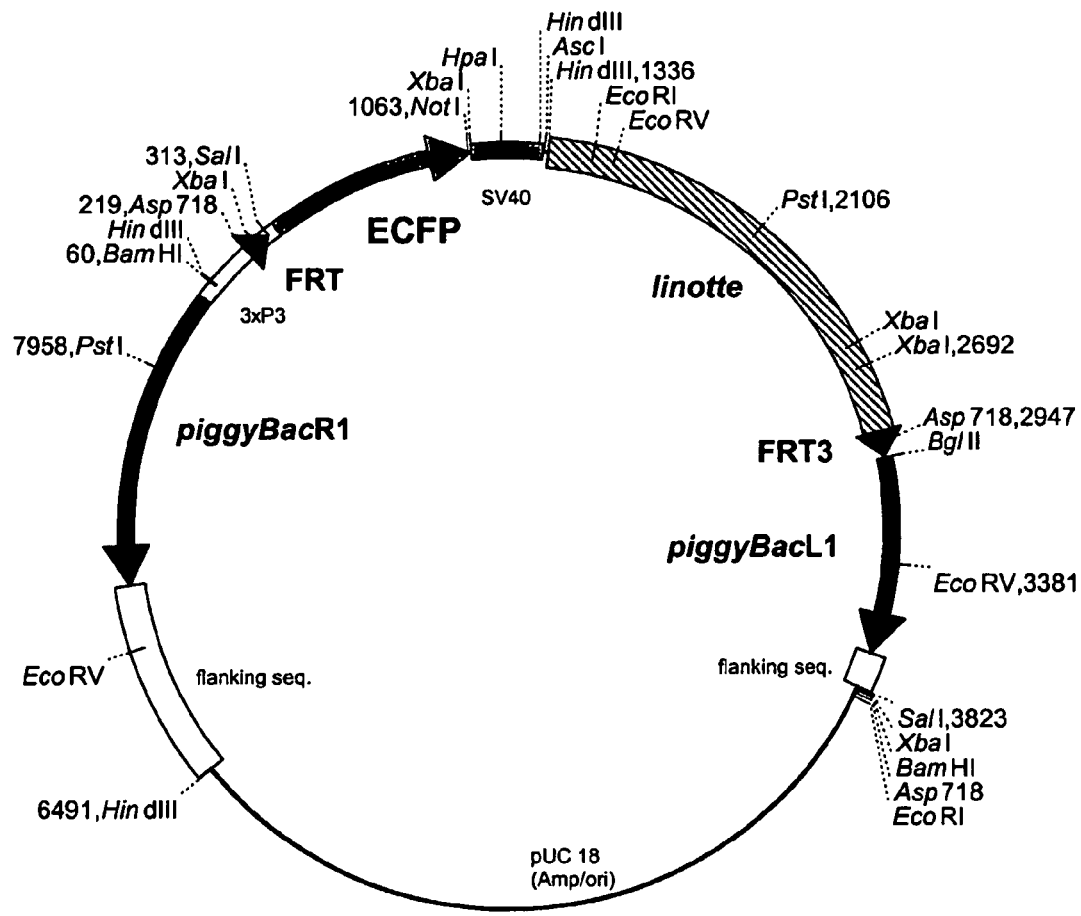
Figure.8: Diagram of RMCE acceptor vector
pBac{3xP3-FRT-ECFP-linotte-FRT3}
Plasmid size: 8.2 kb Fig. 9: Molecular analysis of RMCE acceptor and RMCE donor transgenic lines and PCR analysis of transgene mobilization a) Genomic integration of RMCE acceptor and RMCE donor can be discriminated by Southern Analysis

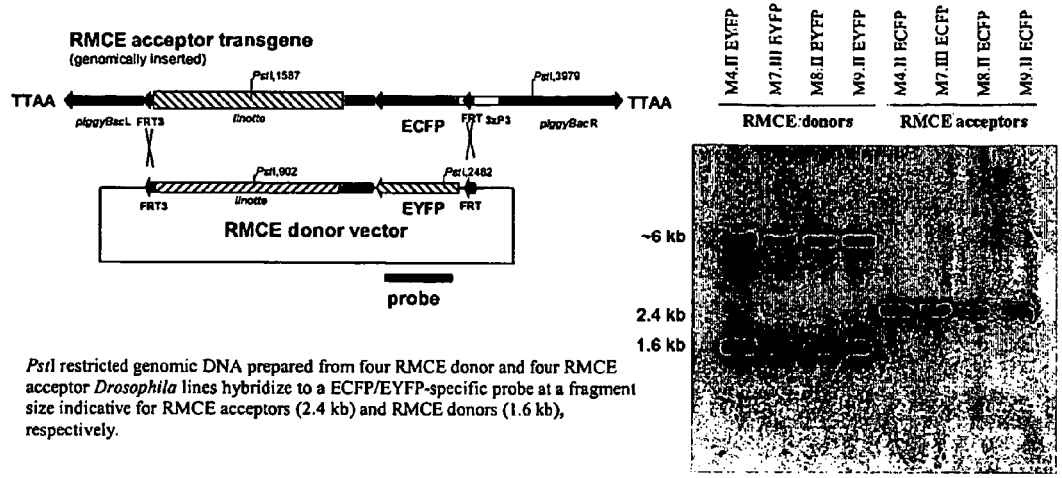

*Pst*I restricted genomic DNA prepared from four RMCE donor and four RMCE acceptor *Drosophila* lines hybridize to a ECFP/EYFP-specific probe at a fragment size indicative for RMCE acceptors (2.4 kb) and RMCE donors (1.6 kb), respectively.

b) Transgene immobilization (as shown in Fig. 7) can be verified by PCR analysis PCR Primers
- pBL-R     5'-TATGAGTTAAATCTTAAAAGTCACG-3'
- M4.II Rev     5'-GGGCCACACGATTTATGGC-3'
- lioFwd     5'-GTTTATTTTTGGCAACATGAG-3' genomically integrated RMCE acceptor (line M4.II ECFP):

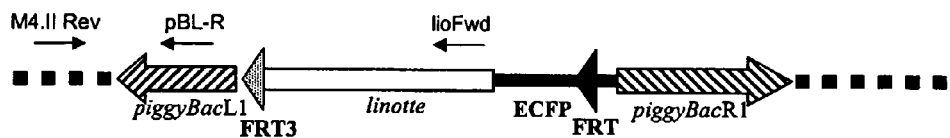

immobilized transgene insertion (lines i#7, i#8):

| Line | Primer pairs | Predicted (bp) | Obtained (kbp) |
|---|---|---|---|
| 1 - M4.II | pBL-R/M4.II Rev | 577 | 0.6 |
| 2 - M4.II | lioFwd/M4.II Rev | 2,836 | 2.8 |
| 3 - i#7 | pBL-R/M4.II Rev | no PCR product | no PCR product |
| 4 - i#7 | lioFwd/M4.II Rev | 650 | 0.6 |
| 5 - i#8 | pBL-R/M4.II Rev | no PCR product | no PCR product |
| 6 - i#8 | lioFwd/M4.II Rev | 650 | 0.6 |

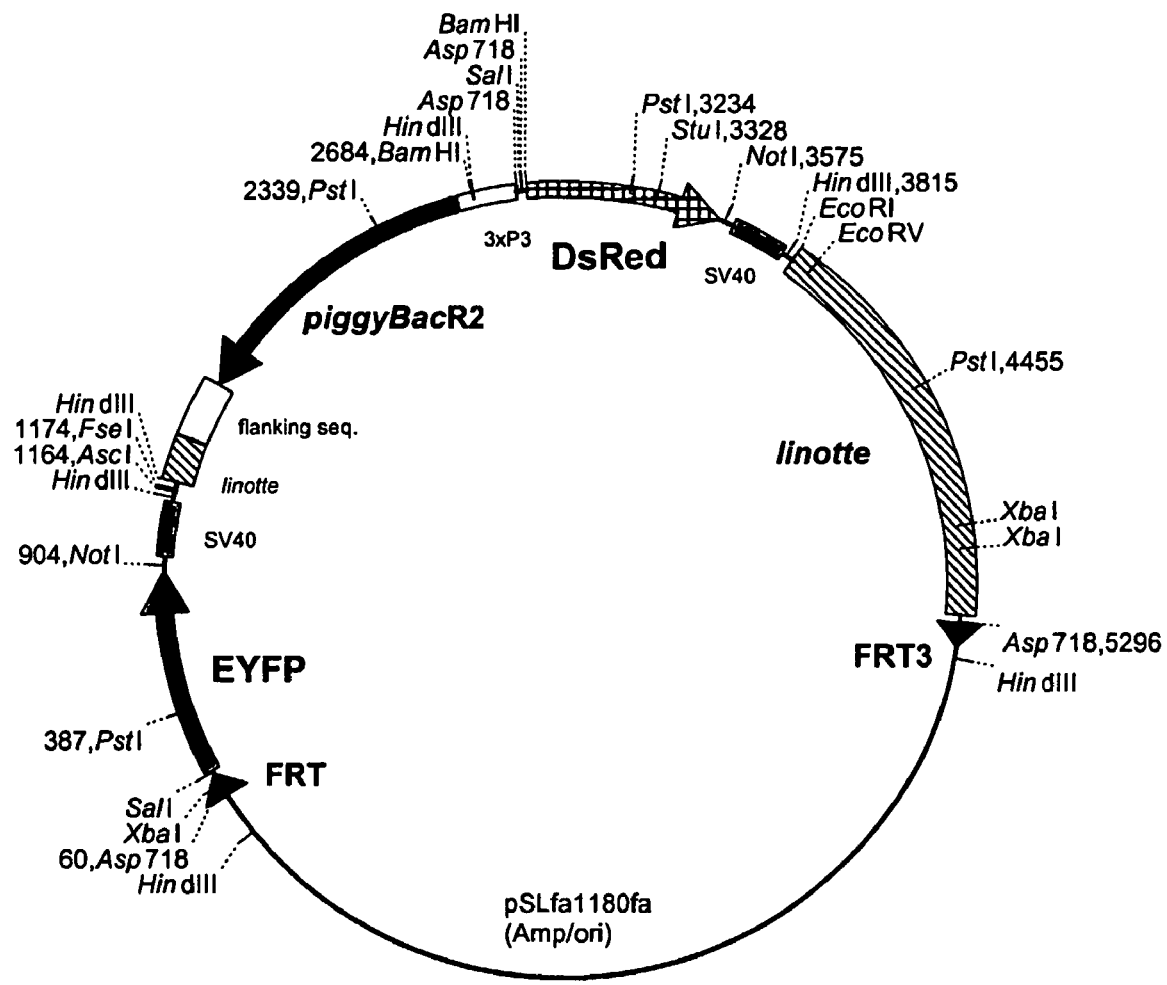
Figure 10: Diagram of final RMCE donor vector for transgene stabilization
pSL-FRT-EYFP-pBacR2-3xP3-DsRed-linotte-FRT3
Plasmid size: 8.6 kb
Unique cloning sites: *AscI*, *FseI*

Fig. 11 Approximate DNA sequence for the vector shown in Fig. 2.

```
CTAAATTGTAAGCGTTAATATTTTGTTAAAATTCGCGTTAAATTTTTGTT
AAATCAGCTCATTTTTTAACCAATAGGCCGAAATCGGCAAAATCCCTTAT
AAATCAAAAGAATAGACCGAGATAGGGTTGAGTGTTGTTCCAGTTTGGAA
CAAGAGTCCACTATTAAAGAACGTGGACTCCAACGTCAAAGGGCGAAAAA
CCGTCTATCAGGGCGATGGCCCACTACGTGAACCATCACCCTAATCAAGT
TTTTTGGGGTCGAGGTGCCGTAAAGCACTAAATCGGAACCCTAAAGGGAG
CCCCCGATTTAGAGCTTGACGGGGAAAGCCGGCGAACGTGGCGAGAAAGG
AAGGGAAGAAAGCGAAAGGAGCGGGCGCTAGGGCGCTGGCAAGTGTAGCG
GTCACGCTGCGCGTAACCACCACACCCGCCGCGCTTAATGCGCCGCTACA
GGGCGCGTCCCATTCGCCATTCAGGCTGCGCAACTGTTGGGAAGGGCGAT
CGGTGCGGGCCTCTTCGCTATTACGCCAGCTGGCGAAAGGGGGATGTGCT
GCAAGGCGATTAAGTTGGGTAACGCCAGGGTTTTCCCAGTCACGACGTTG
TAAAACGACGGCCAGTGAGCGCGCCTCGTTCATTCACGTTTTTGAACCCG
TGGAGGACGGGCAGACTCGCGGTGCAAATGTGTTTTACAGCGTGATGGAG
CAGATGAAGATGCTCGACACGCTGCAGAACACGCAGCTAGATTAACCCTA
GAAAGATAATCATATTGTGACGTACGTTAAAGATAATCATGCGTAAAATT
GACGCATGTGTTTTATCGGTCTGTATATCGAGGTTTATTTATTAATTTGA
ATAGATATTAAGTTTTATTATATTTACACTTACATACTAATAATAAATTC
AACAAACAATTTATTTATGTTTATTTATTTATTAAAAAAAAACAAAAACT
CAAAATTTCTTCTATAAAGTAACAAAACTTTTATCGAATTCCTGCAGCCC
GGGGGATCCACTAGTTCTAGTGTTCCCACAATGGTTAATTCGAGCTCGCC
CGGGGATCTAATTCAATTAGAGACTAATTCAATTAGAGCTAATTCAATTA
GGATCCAAGCTTATCGATTTCGAACCCTCGACCGCCGGAGTATAAATAGA
GGCGCTTCGTCTACGGAGCGACAATTCAATTCAAACAAGCAAAGTGAACA
CGTCGCTAAGCGAAAGCTAAGCAAATAAACAAGCGCAGCTGAACAAGCTA
AACAATCGGGGTACCGCTAGAGTCGACGGTACGATCCACCGGTCGCCACC
ATGGTGAGCAAGGGCGAGGAGCTGTTCACCGGGGTGGTGCCCATCCTGGT
CGAGCTGGACGGCGACGTAAACGGCCACAAGTTCAGCGTGTCCGGCGAGG
GCGAGGGCGATGCCACCTACGGCAAGCTGACCCTGAAGTTCATCTGCACC
ACCGGCAAGCTGCCCGTGCCCTGGCCCACCCTCGTGACCACCCTGACCTG
GGGCGTGCAGTGCTTCAGCCGCTACCCCGACCACATGAAGCAGCACGACT
TCTTCAAGTCCGCCATGCCCGAAGGCTACGTCCAGGAGCGCACCATCTTC
TTCAAGGACGACGGCAACTACAAGACCCGCGCCGAGGTGAAGTTCGAGGG
CGACACCCTGGTGAACCGCATCGAGCTGAAGGGCATCGACTTCAAGGAGG
ACGGCAACATCCTGGGGCACAAGCTGGAGTACAACTACATCAGCCACAAC
GTCTATATCACCGCCGACAAGCAGAAGAACGGCATCAAGGCCAACTTCAA
GATCCGCCACAACATCGAGGACGGCAGCGTGCAGCTCGCCGACCACTACC
AGCAGAACACCCCCATCGGCGACGGCCCCGTGCTGCTGCCCGACAACCAC
TACCTGAGCACCCAGTCCGCCCTGAGCAAAGACCCCAACGAGAAGCGCGA
TCACATGGTCCTGCTGGAGTTCGTGACCGCCGCCGGGATCACTCTCGGCA
TGGACGAGCTGTACAAGTAAAGCGGCCGCGACTCTAGATCATAATCAGCC
ATACCACATTTGTAGAGGTTTTACTTGCTTTAAAAAACCTCCCACACCTC
CCCCTGAACCTGAAACATAAAATGAATGCAATTGTTGTTGTTAACTTGTT
TATTGCAGCTTATAATGGTTACAAATAAAGCAATAGCATCACAAATTTCA
CAAATAAAGCATTTTTTTCACTGCATTCTAGTTGTGGTTTGTCCAAACTC
ATCAATGTATCTTAAAGCTTATCGATACGCGTACGGCGCGCCTAGGCCGG
CCGATACTAGAGCGGCCGCCACCGCGGTGGAGCTCCAGCTTTTGTTCCCT
TTAGTGAGGGTTAATTAGATCTTAATACGACTCACTATAGGGCGAATTGG
GTACCGGGCCCCCCCTCGAGGTCGACGGTATCGATAAGCTTGATATCTAT
AACAAGAAAATATATATATAATAAGTTATCACGTAAGTAGAACATGAAAT
AACAATATAATTATCGTATGAGTTAAATCTTAAAAGTCACGTAAAAGATA
ATCATGCGTCATTTTGACTCACGCGGTCGTTATAGTTCAAAATCAGTGAC
ACTTACCGCATTGACAAGCACGCCTCACGGGAGCTCCAAGCGGCGACTGA
GATGTCCTAAATGCACAGCGACGGATTCGCGCTATTTAGAAAGAGAGAGC
AATATTTCAAGAATGCATGCGTCAATTTTACGCAGACTATCTTTCTAGGG
TTAATCTAGCTGCATCAGGATCATATCGTCGGGTCTTTTTTTCCGGCTCAG
```

Fig. 11a

```
TCATCGCCCAAGCTGGCGCTATCTGGGCATCGGGGAGGAAGAAGCCCGTG
CCTTTTCCGCGAGGTTGAAGCGGCATGGAAAGAGTTTGCCGAGGATGAC
TGCTGCTGCATTGACGTTGAGCGAAAACGCACGTTACCATGATGATTCG
GGAAGGTGTGGGATACATTGATGAGTTTGGACAAACCACAACTAGAATGC
AGTGAAAAAATGCTTTATTTGTGAAATTTGTGATGCTATTGCTTTATTT
GTAACCATTATAAGCTGCAATAAACAAGTTAACAACAACAATTGCATTCA
TTTTATGTTTCAGGTTCAGGGGGAGGTGTGGGAGGTTTTTTAAAGCAAGT
AAAACCTCTACAAATGTGGTATGGCTGATTATGATCTAGAGTCGCGGCCG
CTACAGGAACAGGTGGTGGCGGCCCTCGGTGCGCTCGTACTGCTCCACGA
TGGTGTAGTCCTCGTTGTGGGAGGTGATGTCCAGCTTGGAGTCCACGTAG
TAGTAGCCGGGCAGCTGCACGGGCTTCTTGGCCATGTAGATGGACTTGAA
CTCCACCAGGTAGTGGCCGCCGTCCTTCAGCTTCAGGGCCTTGTGGATCT
CGCCCTTCAGCACGCCGTCGCGGGGGTACAGGCGCTCGGTGGAGGCCTCC
CAGCCCATGGTCTTCTTCTGCATTACGGGCCGTCGGAGGGGAAGTTCAC
GCCGATGAACTTCACCTTGTAGATGAAGCAGCCGTCCTGCAGGGAGGAGT
CTTGGGTCACGGTCACCACGCCGCCGTCCTCGAAGTTCATCACGCGCTCC
CACTTGAAGCCCTCGGGGAAGGACAGCTTCTTGTAGTCGGGGATGTCGGC
GGGGTGCTTCACGTACACCTTGGAGCCGTACTGGAACTGGGGGGACAGGA
TGTCCCAGGCGAAGGGCAGGGGGCCGCCCTTGGTCACCTTCAGCTTCACG
GTGTTGTGGCCCTCGTAGGGGCGGCCCTCGCCCTCGCCCTCGATCTCGAA
CTCGTGGCCGTTCACGGTGCCCTCCATGCGCACCTTGAAGCGCATGAACT
CCTTGATGACGTTCTTGGAGGAGCGCACCATGGTGGCGACCGGTGGATCC
CCGATCTGCATTTTGGATTATTCTGCGGGTCAAAATAGAGATGTGGAAAA
TTAGTACGAAATCAAATGAGTTTCGTTGAAATTACAAAACTATTGAAACT
AACTTCCTGGCTGGGGAATAAAAATGGGAACTTATTTATCGACGCCAAC
TTTGTTGAGAAACCCCTATTAACCCTCTACGAATATTGGAACAAAGGAAA
GCGAAGAAACAGGAACAAAGGTAGTTGAGAAACCTGTTCCGTTGCTCGTC
ATCGTTTTCATAATGCGAGTGTGTGCATGTATATATACACAGCTGAAACG
CATGCATACACATTATTTTGTGTGTATATGGTGACGTCACAACTACTAAG
CAATAAGAAATTTTCCAGACGTGGCTTTCGTTTCAAGCAACCTACTCTAT
TTCAGCTAAAAATAAGTGGATTTCGTTGGTAAAATACTTCAATTAAGCAA
AGAACTAACTAACTAATAACATGCACACAAATGCTCGAGTGCGTTCGTGA
TTTCTCGAATTTTCAAATGCGTCACTGCGAATTTCACAATTTGCCAATAA
ATCTTGGCGAAAATCAACACGCAAGTTTTATTTATAGATTTGTTTGCGTT
TTGATGCCAATTGATTGGGAAAACAAGATGCGTGGCTGCCAATTTCTTAT
TTTGTAATTACGTAGAGCGTTGAATAAAAAAAAATGGCCGAACAAAGAC
CTTGAAATGCAGTTTTCTTGAAATTACTCAACGTCTTGTTGCTCTTATT
ACTAATTGGTAACAGCGAGTTAAAAACTTACGTTTCTTGTGACTTTCGAG
AATGTTCTTTTAATTGTACTTTAATCACCAACAATTAAGTATAAATTTTT
CGCTGATTGCGCTTTACTTTCTGCTTGTACTTGCTGCTGCAAATGTCAAT
TGGTTTTGAAGGCGACCGTTCGCGAACGCTGTTTATATACCTTCGGTGTC
CGTTGAAAATCACTAAAAAATACCGTAGTGTTCGTAACACTTTAGTACAG
AGAAAAAAATTGTGCCGAAATGTTTTGATACGTACGAATACCTTGTAT
TAAAATTTTTTATGATTTCTGTGTATCACTTTTTTTTGTGTTTTCGTT
TAAACTCACCACAGTACAAAACAATAAAATATTTTTAAGACAATTTCAAA
TTGAGACCTTTCTCGTACTGACTTGACCGGCTGAATGAGGATTTCTACCT
AGACGACCTACTTCTTACCATGACATTGAATGCAATGCCACCTTTGATCT
AAACTTACAAAGTCCAAGGCTTGTTAGGATTGGTGTTTATTTAGTTTGC
TTTTGAAATAGCACTGTCTTCTCTACCGGCTATAATTTTGAAACTCGCAG
CTTGACTGGAAATTTAAAAAGTAATTCTGTGTAGGTAAAGGGTGTTTTAA
AAGTGTGATGTGTTGAGCGTTGCGGCAACGACTGCTATTTATGTATATAT
TTTCAAAACTTATTGTTTTTGAAGTGTTTTAAATGGAGCTATCTGGCAAC
GCTGCGCATAATCTTACACAAGCTTTTCTTAATCCATTTTTAAGTGAAAT
TTGTTTTTACTCTTTCGGCAAATAATTGTTAAATCGCTTTAAGTGGGCTT
ACATCTGGATAAGTAATGAAAACCTGCATATTATAATATTAAAACATATA
ATCCACTGTGCTTTCCCCGTGTGTGGCCATATACCTAAAAAAGTTTATTT
```

Fig. 11b

```
TCGCAGAGCCCCGCACGGTCACACTACGGTTCGGCGATTTTCGATTTTGG
ACAGTACTGATTGCAAGCGCACCGAAAGCAAAATGGAGCTGGAGATTTTG
AACGCGAAGAACAGCAAGCCGTACGGCAAGGTGAAGGTGCCCTCCGGCGC
CACGCCCATCGGCGATCTGCGCGCCCTAATTCACAAGACCCTGAAGCAGA
CCCCACACGCGAATCGCCAGTCGCTTCGTCTGGAACTGAAGGGCAAAAGC
CTGAAAGATACGGACACATTGGAATCTCTGTCGCTGCGTTCCGGCGACAA
GATCGGGTACCGTCGACTGCAGAATTCGAAGCTTGAGCTCGAGATCTGAC
AATGTTCAGTGCAGAGACTCGGCTACGCCTCGTGGACTTTGAAGTTGACC
AACAATGTTTATTCTTACCTCTAATAGTCCTCTGTGGCAAGGTCAAGATT
CTGTTAGAAGCCAATGAAGAACCTGGTTGTTCAATAACATTTTGTTCGTC
TAATATTTCACTACCGCTTGACGTTGGCTGCACTTCATGTACCTCATCTA
TAAACGCTTCTTCTGTATCGCTCTGGACGTCATCTTCACTTACGTGATCT
GATATTTCACTGTCAGAATCCTCACCAACAAGCTCGTCATCGCTTTGCAG
AAGAGCAGAGAGGATATGCTCATCGTCTAAAGAACTACCCATTTTATTAT
ATATTAGTCACGATATCTATAACAAGAAAATATATATATAATAAGTTATC
ACGTAAGTAGAACATGAAATAACAATATAATTATCGTATGAGTTAAATCT
TAAAAGTCACGTAAAAGATAATCATGCGTCATTTTGACTCACGCGGTCGT
TATAGTTCAAAATCAGTGACACTTACCGCATTGACAAGCACGCCTCACGG
GAGCTCCAAGCGGCGACTGAGATGTCCTAAATGCACAGCGACGGATTCGC
GCTATTTAGAAAGAGAGAGCAATATTTCAAGAATGCATGCGTCAATTTTA
CGCAGACTATCTTTCTAGGGTTAAAAAAGATTTGCGCTTTACTCGACCTA
AACTTTAAACACGTTAACCATGCACGCCTTTAACGGTGAACTGTTCGTTC
AGGCCACCTGGGATACCAGTTCGTCGCGGCTTTTCCGGACACAGTTCCGG
ATGGTCAGCCCGAAGCGCATCAGCAACCCGAACAATACCGGCGACAGCCG
GAACTGCCGTGCCGGTGTGCAGATTAATGACAGCGGTGCGGCGCTGGGAT
ATTACGTCAGCGAGGACGGGTATCCTGGCTGGATGCCGCAGAAATGGACA
TGGATACCCCGTGAGTTACCCGGCGGGCGCGCTTGGCGTAATCATGGTCA
TAGCTGTTTCCTGTGTGAAATTGTTATCCGCTCACAATTCCACACAACAT
ACGAGCCGGAAGCATAAAGTGTAAAGCCTGGGGTGCCTAATGAGTGAGCT
AACTCACATTAATTGCGTTGCGCTCACTGCCCGCTTTCCAGTCGGGAAAC
CTGTCGTGCCAGCTGCATTAATGAATCGGCCAACGCGCGGGGAGAGGCGG
TTTGCGTATTGGGCGCTCTTCCGCTTCCTCGCTCACTGACTCGCTGCGCT
CGGTCGTTCGGCTGCGGCGAGCGGTATCAGCTCACTCAAAGGCGGTAATA
CGGTTATCCACAGAATCAGGGGATAACGCAGGAAAGAACATGTGAGCAAA
AGGCCAGCAAAAGGCCAGGAACCGTAAAAAGGCCGCGTTGCTGGCGTTTT
TCCATAGGCTCCGCCCCCTGACGAGCATCACAAAAATCGACGCTCAAGT
CAGAGGTGGCGAAACCCGACAGGACTATAAAGATACCAGGCGTTTCCCCC
TGGAAGCTCCCTCGTGCGCTCTCCTGTTCCGACCCTGCCGCTTACCGGAT
ACCTGTCCGCCTTTCTCCCTTCGGGAAGCGTGGCGCTTTCTCATAGCTCA
CGCTGTAGGTATCTCAGTTCGGTGTAGGTCGTTCGCTCCAAGCTGGGCTG
TGTGCACGAACCCCCCGTTCAGCCCGACCGCTGCGCCTTATCCGGTAACT
ATCGTCTTGAGTCCAACCCGGTAAGACACGACTTATCGCCACTGGCAGCA
GCCACTGGTAACAGGATTAGCAGAGCGAGGTATGTAGGCGGTGCTACAGA
GTTCTTGAAGTGGTGGCCTAACTACGGCTACACTAGAAGGACAGTATTTG
GTATCTGCGCTCTGCTGAAGCCAGTTACCTTCGGAAAAAGAGTTGGTAGC
TCTTGATCCGGCAAACAAACCACCGCTGGTAGCGGTGGTTTTTTTGTTTG
CAAGCAGCAGATTACGCGCAGAAAAAAAGGATCTCAAGAAGATCCTTTGA
TCTTTTCTACGGGGTCTGACGCTCAGTGGAACGAAAACTCACGTTAAGGG
ATTTTGGTCATGAGATTATCAAAAAGGATCTTCACCTAGATCCTTTTAAA
TTAAAAATGAAGTTTTAAATCAATCTAAAGTATATATGAGTAAACTTGGT
CTGACAGTTACCAATGCTTAATCAGTGAGGCACCTATCTCAGCGATCTGT
CTATTTCGTTCATCCATAGTTGCCTGACTCCCCGTCGTGTAGATAACTAC
GATACGGGAGGGCTTACCATCTGGCCCCAGTGCTGCAATGATACCGCGAG
ACCCACGCTCACCGGCTCCAGATTTATCAGCAATAAACCAGCCAGCCGGA
AGGGCCGAGCGCAGAAGTGGTCCTGCAACTTTATCCGCCTCCATCCAGTC
TATTAATTGTTGCCGGGAAGCTAGAGTAAGTAGTTCGCCAGTTAATAGTT
TGCGCAACGTTGTTGCCATTGCTACAGGCATCGTGGTGTCACGCTCGTCG
TTTGGTATGGCTTCATTCAGCTCCGGTTCCCAACGATCAAGGCGAGTTAC
```

Fig. 11c
ATGATCCCCCATGTTGTGCAAAAAAGCGGTTAGCTCCTTCGGTCCTCCGA
TCGTTGTCAGAAGTAAGTTGGCCGCAGTGTTATCACTCATGGTTATGGCA
GCACTGCATAATTCTCTTACTGTCATGCCATCCGTAAGATGCTTTTCTGT
GACTGGTGAGTACTCAACCAAGTCATTCTGAGAATAGTGTATGCGGCAC
CGAGTTGCTCTTGCCCGGCGTCAATACGGGATAATACCGCGCCACATAGC
AGAACTTTAAAAGTGCTCATCATTGGAAAACGTTCTTCGGGGCGAAAACT
CTCAAGGATCTTACCGCTGTTGAGATCCAGTTCGATGTAACCCACTCGTG
CACCCAACTGATCTTCAGCATCTTTTACTTTCACCAGCGTTTCTGGGTGA
GCAAAAACAGGAAGGCAAAATGCCGCAAAAAAGGGAATAAGGGCGACACG
GAAATGTTGAATACTCATACTCTTCCTTTTTCAATATTATTGAAGCATTT
ATCAGGGTTATTGTCTCATGAGCGGATACATATTTGAATGTATTTAGAAA
AATAAACAAATAGGGGTTCCGCGCACATTTCCCCGAAAAGTGCCAC

Fig. 12 Approximate DNA sequence for the vector shown in Fig. 8
pBac{3xP3-FRT-ECFP-linotte-FRT3}

1
GAGCTCGCCCGGGGATCTAATTCAATTAGAGACTAATTCAATTAGAGCTAATTCAATTAGGATCCAAGCTTAT
CGATTTCGAACCCTCGACCGCCGGAGTATAAATAGAGGCGCTTCGTCTACGGAGCGACAATTCAATTCAAACA
AGCAAAGTGAACACGTCGCTAAGCGAAAGCTAAGCAAATAAACAAGCGCAGCTGAACAAGCTAAACAATCGGG
GTACCCGGGGATCTTGAAGTTCCTATTCCGAAGTTCCTATTCTCTAGAAAGTATAGGAACTTCAGAGCGCTTT
TGAAGCTAGGCGGCCCTAGAGTCGACGGTACGATCCACCGGTCGCCACCATGGTGAGCAAGGGCGAGGAGCTG
TTCACCGGGGTGGTGCCCATCCTGGTCGAGCTGGACGGCGACGTAAACGGCCACAAGTTCAGCGTGTCCGGCG
AGGGCGAGGGCGATGCCACCTACGGCAAGCTGACCCTGAAGTTCATCTGCACCACCGGCAAGCTGCCCGTGCC
CTGGCCCACCCTCGTGACCACCCTGACCTGGGGCGTGCAGTGCTTCAGCCGCTACCCCGACCACATGAAGCAG
CACGACTTCTTCAAGTCCGCCATGCCCGAAGGCTACGTCCAGGAGCGCACCATCTTCTTCAAGGACGACGGCA
ACTACAAGACCCGCGCCGAGGTGAAGTTCGAGGGCGACACCCTGGTGAACCGCATCGAGCTGAAGGGCATCGA
CTTCAAGGAGGACGGCAACATCCTGGGGCACAAGCTGGAGTACAACTACATCAGCCACAACGTCTATATCACC
GCCGACAAGCAGAAGAACGGCATCAAGGCCAACTTCAAGATCCGCCACAACATCGAGGACGGCAGCGTGCAGC
TCGCCGACCACTACCAGCAGAACACCCCCATCGGCGACGGCCCCGTGCTGCTGCCCGACAACCACTACCTGAG
CACCCAGTCCGCCCTGAGCAAAGACCCCAACGAGAAGCGCGATCACATGGTCCTGCTGGAGTTCGTGACCGCC
GCCGGGATCACTCTCGGCATGGACGAGCTGTACAAGTAAAGCGGCCGCGACTCTAGATCATAATCAGCCATAC
CACATTTGTAGAGGTTTTACTTGCTTTAAAAAACCTCCCACACCTCCCCCTGAACCTGAAACATAAAATGAAT
GCAATTGTTGTTGTTAACTTGTTTATTGCAGCTTATAATGGTTACAAATAAAGCAATAGCATCACAAATTTCA
CAAATAAAGCATTTTTTTCACTGCATTCTAGTTGTGGTTTGTCCAAACTCATCAATGTATCTTAAAGCTTATC
GATACGCGTACGGCGCGCCAAAAGCTTCTGTCTCTCTTTCTGTAATAAACTAACGATTTATAAAGTATAAAAT
GTCGTAATGTTTATTTTTGGCAACATGAGTTTAATTCGAAATTGAATCAAACACAATAAAAAAAAGTTAAAAG
GTTAAAATCATTATATTACATCATTAATTCGAATTCATTTGGGAAGTTTGTGGGTCTATTTTTTAAACTTTAT
ATGAATGTTTGTTTAGTTAATTTAATAAAGGATATCGAACAGTATGCCAGTTTTGGTATTTAGCCAATTGGAG
ATGTTCGATGAGATGTTCGAACTGCAACCGAGTTCGAGGTTCCAACACGACTGTTATACGGGTTCCAGCCTTC
AAGTTCTACAGAACAAGTCCACGAGCGCCACACACAGTCCACAGTCCACACTCCACTCCGCTCGGCGTGGAAG
CCATTCGCTTCGTGGCGAAGTGTTTGTTTATCCAGTTGACAGTTTGTGGAAAATCGTCACGGTGAGCGGATCA
AACGCGGAAAACGAACGCGGACGAACGGCGAGAAAAGCGAGGAAAAACGGGTGCAGAGACAGAGACTGATTGG
GAAATATGTGCGCCTGAGTTTTCCCGGCCAGAAGGCAAAGTGCCAAATGCTCTGACAAATAATTCCTGTAATA
ATCAGCGCGATTGAAATCAACGCGACGCTCGTAAAATTGCAAATGCAGCGCAAAAAGTGAACAGCAGTGCAGC
GGAAATTAAATCGTTTTAGCGAGTGCCAAACGGGAAATAGAAAATCGGCAGAGTAGCCGAACTGCAGTTAAAA
CTATCTCTTCCTCTTATTGCGACTAAACAACCGGCGGATTAATCGAATCCGAAAGATGGCCCCCAACTTGCTA
ACAATCGGATTACTTTTGACCCTGATCGCCAGCGGTCAGGCCCATCTCAATATTTTCCTCAACTTGCACGAGG
TGCTGCGCCTAATCGGTAAGTAATCGTGTTGATTTTCGCCTGCCTTTTGGCTTTTCAATTAACTGGGCAATTA
TTTGCCACTTTGTGTGCGTTCGTTCGACTTTAAATCAAATTTGATTTATGCCAAGCCGGGATTTTGTCTCCTG
GGCAAACGAATGCGACTTGCTGGGATTATTTACTCTTTTTGCGTAAATAATATATGCCTTTTAATTGTTTCTA
GCCTCGGAGCTACATATAAAGTAGTATTGTCCCTCCTTCAATTGGCCAGCTCACCGAGAAACAAGAAAACATT
CTATTTGTCTAGCATGATTTCCTGTTTCTTTGATTTAATTGTTCGTTAGACTTATCTAGATAAATAGAAATGC
TAAAGCGATTTAAATTTGTATTTCTTTGCGTTAAATTAAATTCGATTGGCAAGTGGATTCATCTCTAGATAAG
TAATCCCTCTATAATCAAAGTTTTTATTTAAAAAATCATATTTTTTCATAGTTTATCCAATTTAAAACAATAC
AAAACAATTTTAGATATATTTTATAAACGTCTTCAAAAGAAAATAAATAGTAAAATCATGTAGTCAAAAAATG
ACACCAAAATGAGTATTTAAATATTTAGTTTAGTTTAGTTTATATTATTTATTTAGCCTAACTATTTTCCATA
GAAGAATACTACTCTAATAAGCTTGGGGTACCCGGGGATCTTGAAGTTCCTATTCCGAAGTTCCTATTCTTCA
AATAGTATAGGAACTTCAGATCTGACAATGTTCAGTGCAGAGACTCGGCTACGCCTCGTGGACTTTGAAGTTG
ACCAACAATGTTTATTCTTACCTCTAATAGTCCTCTGTGGCAAGGTCAAGATTCTGTTAGAAGCCAATGAAGA
ACCTGGTTGTTCAATAACATTTTGTTCGTCTAATATTTCACTACCGCTTGACGTTGGCTGCACTTCATGTACC
TCATCTATAAACGCTTCTTCTGTATCGCTCTGGACGTCATCTTCACTTACGTGATCTGATATTTCACTGTCAG
AATCCTCACCAACAAGCTCGTCATCGCTTTGCAGAAGAGCAGAGAGGATATGCTCATCGTCTAAAGAACTACC
CATTTTATTATATATTAGTCACGATATCTATAACAAGAAAATATATATATAATAAGTTATCACGTAAGTAGAA
CATGAAATAACAATATAATTATCGTATGAGTTAAATCTTAAAAGTCACGTAAAAGATAATCATGCGTCATTTT
GACTCACGCGGTCGTTATAGTTCAAAATCAGTGACACTTACCGCATTGACAAGCACGCCTCACGGGAGCTCCA
AGCGGCGACTGAGATGTCCTAAATGCACAGCGACGGATTCGCGCTATTTAGAAAGAGAGAGCAATATTTCAAG
AATGCATGCGTCAATTTTACGCAGACTATCTTTCTAGGGTTAAAAAAGATTTGCGCTTTACTCGACCTAAACT
TTAAACACGTCATAGAATCTTCGTTTGACAAAAACCACATTGTGGCCAAGCTGTGTGACGCGACGCGCGCTAA
AGAATGGCAAACCAAGTCGCGCGAGCGTCGACTCTAGAGGATCCCCGGGTACCGAGCTCGAATTCGTAATCAT
GGTCATAGCTGTTTCCTGTGTGAAATTGTTATCCGCTCACAATTCCACACAACATACGAGCCGGAAGCATAAA
GTGTAAAGCCTGGGGTGCCTAATGAGTGAGCTAACTCACATTAATTGCGTTGCGCTCACTGCCCGCTTTCCAG
TCGGGAAACCTGTCGTGCCAGCTGCATTAATGAATCGGCCAACGCGCGGGGAGAGGCGGTTTGCGTATTGGGC

Fig. 12 a

```
GCTCTTCCGCTTCCTCGCTCACTGACTCGCTGCGCTCGGTCGTTCGGCTGCGGCGAGCGGTATCAGCTCACTC
AAAGGCGGTAATACGGTTATCCACAGAATCAGGGGATAACGCAGGAAAGAACATGTGAGCAAAAGGCCAGCAA
AAGGCCAGGAACCGTAAAAAGGCCGCGTTGCTGGCGTTTTTCCATAGGCTCCGCCCCCCTGACGAGCATCACA
AAAATCGACGCTCAAGTCAGAGGTGGCGAAACCCGACAGGACTATAAAGATACCAGGCGTTTCCCCCTGGAAG
CTCCCTCGTGCGCTCTCCTGTTCCGACCCTGCCGCTTACCGGATACCTGTCCGCCTTTCTCCCTTCGGGAAGC
GTGGCGCTTTCTCAATGCTCACGCTGTAGGTATCTCAGTTCGGTGTAGGTCGTTCGCTCCAAGCTGGGCTGTG
TGCACGAACCCCCCGTTCAGCCCGACCGCTGCGCCTTATCCGGTAACTATCGTCTTGAGTCCAACCCGGTAAG
ACACGACTTATCGCCACTGGCAGCAGCCACTGGTAACAGGATTAGCAGAGCGAGGTATGTAGGCGGTGCTACA
GAGTTCTTGAAGTGGTGGCCTAACTACGGCTACACTAGAAGGACAGTATTTGGTATCTGCGCTCTGCTGAAGC
CAGTTACCTTCGGAAAAAGAGTTGGTAGCTCTTGATCCGGCAAACAAACCACCGCTGGTAGCGGTGGTTTTTT
TGTTTGCAAGCAGCAGATTACGCGCAGAAAAAAAGGATCTCAAGAAGATCCTTTGATCTTTTCTACGGGGTCT
GACGCTCAGTGGAACGAAAACTCACGTTAAGGGATTTTGGTCATGAGATTATCAAAAAGGATCTTCACCTAGA
TCCTTTTAAATTAAAAATGAAGTTTTAAATCAATCTAAAGTATATATGAGTAAACTTGGTCTGACAGTTACCA
ATGCTTAATCAGTGAGGCACCTATCTCAGCGATCTGTCTATTTCGTTCATCCATAGTTGCCTGACTCCCCGTC
GTGTAGATAACTACGATACGGGAGGGCTTACCATCTGGCCCCAGTGCTGCAATGATACCGCGAGACCCACGCT
CACCGGCTCCAGATTTATCAGCAATAAACCAGCCAGCCGGAAGGGCCGAGCGCAGAAGTGGTCCTGCAACTTT
ATCCGCCTCCATCCAGTCTATTAATTGTTGCCGGGAAGCTAGAGTAAGTAGTTCGCCAGTTAATAGTTTGCGC
AACGTTGTTGCCATTGCTACAGGCATCGTGGTGTCACGCTCGTCGTTTGGTATGGCTTCATTCAGCTCCGGTT
CCCAACGATCAAGGCGAGTTACATGATCCCCCATGTTGTGCAAAAAAGCGGTTAGCTCCTTCGGTCCTCCGAT
CGTTGTCAGAAGTAAGTTGGCCGCAGTGTTATCACTCATGGTTATGGCAGCACTGCATAATTCTCTTACTGTC
ATGCCATCCGTAAGATGCTTTTCTGTGACTGGTGAGTACTCAACCAAGTCATTCTGAGAATAGTGTATGCGGC
GACCGAGTTGCTCTTGCCCGGCGTCAATACGGGATAATACCGCGCCACATAGCAGAACTTTAAAAGTGCTCAT
CATTGGAAAACGTTCTTCGGGGCGAAAACTCTCAAGGATCTTACCGCTGTTGAGATCCAGTTCGATGTAACCC
ACTCGTGCACCCAACTGATCTTCAGCATCTTTTACTTTCACCAGCGTTTCTGGGTGAGCAAAAACAGGAAGGC
AAAATGCCGCAAAAAAGGGAATAAGGGCGACACGGAAATGTTGAATACTCATACTCTTCCTTTTTCAATATTA
TTGAAGCATTTATCAGGGTTATTGTCTCATGAGCGGATACATATTTGAATGTATTTAGAAAAATAAACAAATA
GGGGTTCCGCGCACATTTCCCCGAAAAGTGCCACCTGACGTCTAAGAAACCATTATTATCATGACATTAACCT
ATAAAAATAGGCGTATCACGAGGCCCTTTCGTCTCGCGCGTTTCGGTGATGACGGTGAAAACCTCTGACACAT
GCAGCTCCCGGAGACGGTCACAGCTTGTCTGTAAGCGGATGCCGGGAGCAGACAAGCCCGTCAGGGCGCGTCA
GCGGGTGTTGGCGGGTGTCGGGGCTGGCTTAACTATGCGGCATCAGAGCAGATTGTACTGAGAGTGCACCATA
TGCGGTGTGAAATACCGCACAGATGCGTAAGGAGAAAATACCGCATCAGGCGCCATTCGCCATTCAGGCTGCG
CAACTGTTGGGAAGGGCGATCGGTGCGGGCCTCTTCGCTATTACGCCAGCTGGCGAAAGGGGGATGTGCTGCA
AGGCGATTAAGTTGGGTAACGCCAGGGTTTTCCCAGTCACGACGTTGTAAAACGACGGCCAGTGCCAAGCTTT
GTTTAAAATATAACAAAATTGTGATCCCACAAAATGAAGTGGGGCAAAATCAAATAATTAATAGTGTCCGTAA
ACTTGTTGGTCTTCAACTTTTTGAGGAACACGTTGGACGGCAAATCCGTGACTATAACACAAGTTGATTTAAT
AATTTTAGCCAACACGTCGGGCTGCGTGTTTTTGCCGACGCGTCTGTGTACACGTTGATTAACTGGTCGATT
AAACTGTTGAAATAATTTAATTTTTGGTTCTTCTTTAAATCTGTGATGAAATTTTTTAAAATAACTTTAAATT
CTTCATTGGTAAAAAATGCCACGTTTTGCAACTTGTGAGGGTCTAATATGAGGTCAAACTCAGTAGGAGTTTT
ATCCAAAAAAGAAAACATGATTACGTCTGTACACGAACGCGTATTAACGCAGAGTGCAAAGTATAAGAGGGTT
AAAAAATATATTTTACGCACCATATACGCATCGGGTTGATATCGTTAATATGGATCAATTTGAACAGTTGATT
AACGTGTCTCTGCTCAAGTCTTTGATCAAAACGCAAATCGACGAAAATGTGTCGGACAATATCAAGTCGATGA
GCGAAAAACTAAAAAGGCTAGAATACGACAATCTCACAGACAGCGTTGAGATATACGGTATTCACGACAGCAG
GCTGAATAATAAAAAAATTAGAAACTATTATTTAACCCTAGAAAGATAATCATATTGTGACGTACGTTAAAGA
TAATCATGCGTAAAATTGACGCATGTGTTTTATCGGTCTGTATATCGAGGTTTATTTATTAATTTGAATAGAT
ATTAAGTTTTATTATATTTACACTTACATACTAATAATAAATTCAACAAACAATTTATTTATGTTTATTTATT
TATTAAAAAAAAACAAAACTCAAAATTTCTTCTATAAAGTAACAAAACTTTTAAACATTCTCTCTTTTACAA
AAATAAACTTATTTTGTACTTTAAAAACAGTCATGTTGTATTATAAAATAAGTAATTAGCTTAACTTATACAT
AATAGAAACAAATTATACTTATTAGTCAGTCAGAAACAACTTTGGCACATATCAATATTATGCTCTCGACAAA
TAACTTTTTTGCATTTTTTGCACGATGCATTTGCCTTTCGCCTTATTTTAGAGGGGCAGTAAGTACAGTAAGT
ACGTTTTTTCATTACTGGCTCTTCAGTACTGTCATCTGATGTACCAGGCACTTCATTTGGCAAAATATTAGAG
ATATTATCGCGCAAATATCTCTTCAAAGTAGGAGCTTCTAAACGCTTACGCATAAACGATGACGTCAGGCTCA
TGTAAAGGTTTCTCATAAATTTTTTGCGACTTTGGACCTTTTCTCCCTTGCTACTGACATTATGGCTGTATAT
AATAAAAGAATTTATGCAGGCAATGTTTATCATTCCGTACAATAATGCCATAGGCCACCTATTCGTCTTCCTA
CTGCAGGTCATCACAGAACACATTTGGTCTAGCGTGTCCACTCCGCCTTTAGTTTGATTATAATACATAACCA
TTTGCGGTTTACCGGTACTTTCGTTGATAGAAGCATCCTCATCACAAGATGATAATAAGTATACCATCTTAGC
TGGCTTCGGTTTATATGAGACGAGAGTAAGGGGTCCGTCAAAACAAAACATCGATGTTCCCACTGGCCTGGAG
CGACTGTTTTTCAGTACTTCCGGTATCTCGCGTTTGTTTGATCGCACGGTTCCCACAATGGTTAATTC
8244
```

Fig. 13 Approximate DNA sequence for the vector shown in Fig. 10
pSL-FRT-EYFP-pBacR-3xP3-DsRed-linotte-FRT3

```
CGTCGCTAAGCGAAAGCTAAGCAAATAAACAAGCGCAGCTGAACAAGCTAAACAATCGGGGTACCCGGGGATCTT
GAAGTTCCTATTCCGAAGTTCCTATTCTCTAGAAAGTATAGGAACTTCAGAGCGCTTTTGAAGCTAGGCGGCCCT
AGAGTCGACGGTACGATCCACCGGTCGCCACCATGGTGAGCAAGGGCGAGGAGCTGTTCACCGGGGTGGTGCCCA
TCCTGGTCGAGCTGGACGGCGACGTAAACGGCCACAAGTTCAGCGTGTCCGGCGAGGGCGAGGGCGATGCCACCT
ACGGCAAGCTGACCCTGAAGTTCATCTGCACCACCGGCAAGCTGCCCGTGCCCTGGCCCACCCTCGTGACCACCT
TCGGCTACGGCCTGCAGTGCTTCGCCCGCTACCCCGACCACATGAAGCAGCACGACTTCTTCAAGTCCGCCATGC
CCGAAGGCTACGTCCAGGAGCGCACCATCTTCTTCAAGGACGACGGCAACTACAAGACCCGCGCCGAGGTGAAGT
TCGAGGGCGACACCCTGGTGAACCGCATCGAGCTGAAGGGCATCGACTTCAAGGAGGACGGCAACATCCTGGGGC
ACAAGCTGGAGTACAACTACAACAGCCACAACGTCTATATCATGGCCGACAAGCAGAAGAACGGCATCAAGGTGA
ACTTCAAGATCCGCCACAACATCGAGGACGGCAGCGTGCAGCTCGCCGACCACTACCAGCAGAACACCCCCATCG
GCGACGGCCCCGTGCTGCTGCCCGACAACCACTACCTGAGCTACCAGTCCGCCCTGAGCAAAGACCCCAACGAGA
AGCGCGATCACATGGTCCTGCTGGAGTTCGTGACCGCCGCCGGGATCACTCTCGGCATGGACGAGCTGTACAAGT
AAAGCGGCCGCGACTCTAGATCATAATCAGCCATACCACATTTGTAGAGGTTTTACTTGCTTTAAAAAACCTCCC
ACACCTCCCCCTGAACCTGAAACATAAAATGAATGCAATTGTTGTTGTTAACTTGTTTATTGCAGCTTATAATGG
TTACAAATAAAGCAATAGCATCACAAATTTCACAAATAAAGCATTTTTTTCACTGCATTCTAGTTGTGGTTTGTC
CAAACTCATCAATGTATCAAGCTTATCGATACGCGTACGGCGCGCCTAGGCCGGCCGATCTCGCGCGCCAAAAGC
TTCTGTCTCTCTTTCTGTAATAAACTAACGATTTATAAAGTATAAAATGTCGTAATGTTTATTTTTGGCAACATG
AGTTTAATTCGAAATTGAATCAAACACAATAAAAAAAAGTTAAAAGGTTAAAATCATTATATTACATCATTAATT
CGAATTATCGTTAATATGGATCAATTTGAACAGTTGATTAACGTGTCTCTGCTCAAGTCTTTGATCAAAACGCAA
ATCGACGAAAATGTGTCGGACAATATCAAGTCGATGAGCGAAAAACTAAAAAGGCTAGAATACGACAATCTCACA
GACAGCGTTGAGATATACGGTATTCACGACAGCAGGCTGAATAATAAAAAAATTAGAAACTATTATTTAACCCTA
GAAAGATAATCATATTGTGACGTACGTTAAAGATAATCATGCGTAAAATTGACGCATGTGTTTATCGGTCTGTA
TATCGAGGTTTATTTATTAATTTGAATAGATATTAAGTTTTATTATATTTACACTTACATACTAATAATAAATTC
AACAAACAATTTATTTATGTTTATTTATTTATTAAAAAAAAACAAAAACTCAAAATTTCTTCTATAAAGTAACAA
AACTTTTAAACATTCTCTCTTTTACAAAAATAAACTTATTTTGTACTTTAAAAACAGTCATGTTGTATTATAAAA
TAAGTAATTAGCTTAACTTATACATAATAGAAACAAATTATACTTATTAGTCAGTCAGAAACAACTTTGGCACAT
ATCAATATTATGCTCTCGACAAATAACTTTTTTGCATTTTTTGCACGATGCATTTGCCTTTCGCCTTATTTTAGA
GGGGCAGTAAGTACAGTAAGTACGTTTTTTCATTACTGGCTCTTCAGTACTGTCATCTGATGTACCAGGCACTTC
ATTTGGCAAAATATTAGAGATATTATCGCGCAAATATCTCTTCAAAGTAGGAGCTTCTAAACGCTTACGCATAAA
CGATGACGTCAGGCTCATGTAAAGGTTTCTCATAAATTTTTTGCGACTTTGGACCTTTTCTCCCTTGCTACTGAC
ATTATGGCTGTATATAATAAAAGAATTTATGCAGGCAATGTTTATCATTCCGTACAATAATGCCATAGGCCACCT
ATTCGTCTTCCTACTGCAGGTCATCACAGAACACATTTGGTCTAGCGTGTCCACTCCGCCTTTAGTTTGATTATA
ATACATAACCATTTGCGGTTTACCGGTACTTTCGTTGATAGAAGCATCCTCATCACAAGATGATAATAAGTATAC
CATCTTAGCTGGCTTCGGTTTATATGAGACGAGAGTAAGGGGTCCGTCAAAACAAAACATCGATGTTCCCACTGG
CCTGGAGCGACTGTTTTTCAGTACTTCCGGTATCTCGCGTTTGTTTGATCGCACGGTTCCCACAATGGTAATTCG
AGCTCGCCCGGGGATCTAATTCAATTAGAGACTAATTCAATTAGAGCTAATTCAATTAGGATCCAAGCTTATCGA
TTTCGAACCCTCGACCGCCGGAGTATAAATAGAGGCGCTTCGTCTACGGAGCGACAATTCAATTCAAACAAGCAA
AGTGAACACGTCGCTAAGCGAAAGCTAAGCAAATAAACAAGCGCAGCTGAACAAGCTAAACAATCGGGGTACCGC
TAGAGTCGACGGTACGCGGGCCCGGGATCCACCGGTCGCCACCATGGTGCGCTCCTCCAAGAACGTCATCAAGG
AGTTCATGCGCTTCAAGGTGCGCATGGAGGGCACCGTGAACGGCCACGAGTTCGAGATCGAGGGCGAGGGCGAGG
GCCGCCCCTACGAGGGCCACAACACCGTGAAGCTGAAGGTGACCAAGGGCGGCCCCCTGCCCTTCGCCTGGGACA
TCCTGTCCCCCCAGTTCCAGTACGGCTCCAAGGTGTACGTGAAGCACCCCGCCGACATCCCCGACTACAAGAAGC
TGTCCTTCCCCGAGGGCTTCAAGTGGGAGCGCGTGATGAACTTCGAGGACGGCGGCGTGGTGACCGTGACCCAGG
ACTCCTCCCTGCAGGACGGCTGCTTCATCTACAAGGTGAAGTTCATCGGCGTGAACTTCCCCTCCGACGGCCCCG
TAATGCAGAAGAAGACCATGGGCTGGGAGGCCTCCACCGAGCGCCTGTACCCCCGCGACGGCGTGCTGAAGGGCG
AGATCCACAAGGCCCTGAAGCTGAAGGACGGCGGCCACTACCTGGTGGAGTTCAAGTCCATCTACATGGCCAAGA
AGCCCGTGCAGCTGCCCGGCTACTACTACGTGGACTCCAAGCTGGACATCACCTCCCACAACGAGGACTACACCA
TCGTGGAGCAGTACGAGCGCACCGAGGGCCGCCACCACCTGTTCCTGTAGCGGCCGCGACTCTAGATCATAATCA
GCCATACCACATTTGTAGAGGTTTTACTTGCTTTAAAAAACCTCCCACACCTCCCCCTGAACCTGAAACATAAAA
TGAATGCAATTGTTGTTGTTAACTTGTTTATTGCAGCTTATAATGGTTACAAATAAAGCAATAGCATCACAAATT
TCACAAATAAAGCATTTTTTCACTGCATTCTAGTTGTGGTTTGTCCAAACTCATCAATGTATCAAGCTTATCGA
TACGCGTACGGCGCGAATTCATTTGGGAAGTTTGTGGGTCTATTTTTTAAACTTTATATGAATGTTTGTTTAGTT
AATTTAATAAAGGATATCGAACAGTATGCCAGTTTTGGTATTTAGCCAATTGGAGATGTTCGATGAGATGTTCGA
ACTGCAACCGAGTTCGAGGTTCCAACACGACTGTTATACGGGTTCCAGCCTTCAAGTTCTACAGAACAAGTCCAC
GAGCGCCACACACAGTCCACAGTCCACACTCCACTCCGCTCGGCGTGGAAGCCATTCGCTTCGTGGCGAAGTGTT
TGTTTATCCAGTTGACAGTTTGTGGAAAATCGTCACGGTGAGCGGATCAAACGCGGAAAACGAACGCGGACGAAC
GGCGAGAAAAGCGAGGAAAAACGGGTGCAGAGACAGAGACTGATTGGGAAATATGTGCGCCTGAGTTTTCCCGGC
CAGAAGGCAAAGTGCCAAATGCTCTGACAAATAATTCCTGTAATAATCAGCGCGATTGAAATCAACGCGACGCTC
```

Fig. 13a

```
GTAAAATTGCAAATGCAGCGCAAAAAGTGAACAGCAGTGCAGCGGAAATTAAATCGTTTTAGCGAGTGCCAAACG
GGAAATAGAAAATCGGCAGAGTAGCCGAACTGCAGTTAAAACTATCTCTTCCTCTTATTGCGACTAAACAACCGG
CGGATTAATCGAATCCGAAAGATGGCCCCCAACTTGCTAACAATCGGATTACTTTTGACCCTGATCGCCAGCGGT
CAGGCCCATCTCAATATTTTCCTCAACTTGCACGAGGTGCTGCGCCTAATCGGTAAGTAATCGTGTTGATTTTCG
CCTGCCTTTTGGCTTTTCAATTAACTGGGCAATTATTTGCCACTTTGTGTGCGTTCGTTCGACTTTAAATCAAAT
TTGATTTATGCCAAGCCGGGATTTTGTCTCCTGGGCAAACGAATGCGACTTGCTGGGATTATTTACTCTTTTTGC
GTAAATAATATATGCCTTTTAATTGTTTCTAGCCTCGGAGCTACATATAAAGTAGTATTGTCCCTCCTTCAATTG
GCCAGCTCACCGAGAAACAAGAAAACATTCTATTTGTCTAGCATGATTTCCTGTTTCTTTGATTTAATTGTTCGT
TAGACTTATCTAGATAAATAGAAATGCTAAAGCGATTTAAATTTGTATTTCTTTGCGTTAAATTAAATTCGATTG
GCAAGTGGATTCATCTCTAGATAAGTAATCCCTCTATAATCAAAGTTTTTATTTAAAAAATCATATTTTTTCATA
GTTTATCCAATTTAAAACAATACAAAACAATTTTAGATATATTTTATAAACGTCTTCAAAAGAAAATAAATAGTA
AAATCATGTAGTCAAAAAATGACACCAAAATGAGTATTTAAATATTTAGTTTAGTTTAGTTTATATTATTTATTT
AGCCTAACTATTTTCCATAGAAGAATACTACTCTAATAAGCTTGGGGTACCCGGGGATCTTGAAGTTCCTATTCC
GAAGTTCCTATTCTTCAAATAGTATAGGAACTTCAGATCCGACCGCGGACATGTACAGAGCTCGAGAAGTACTAG
TGGCCACGTGGGCCGTGCACCTTAAGCTTGGCACTGGCCGTCGTTTTACAACGTCGTGACTGGGAAAACCCTGGC
GTTACCCAACTTAATCGCCTTGCAGCACATCCCCCTTTCGCCAGCTGGCGTAATAGCGAAGAGGCCCGCACCGAT
CGCCCTTCCCAACAGTTGCGCAGCCTGAATGGCGAATGGCGCCTGATGCGGTATTTTCTCCTTACGCATCTGTGC
GGTATTTCACACCGCATACGTCAAAGCAACCATAGTACGCGCCCTGTAGCGGCGCATTAAGCGCGGCGGGTGTGG
TGGTTACGCGCAGCGTGACCGCTACACTTGCCAGCGCCCTAGCGCCCGCTCCTTTCGCTTTCTTCCCTTCCTTTC
TCGCCACGTTCGCCGGCTTTCCCCGTCAAGCTCTAAATCGGGGGCTCCCTTTAGGGTTCCGATTTAGTGCTTTAC
GGCACCTCGACCCCAAAAAACTTGATTTGGGTGATGGTTCACGTAGTGGGCCATCGCCCTGATAGACGGTTTTTC
GCCCTTTGACGTTGGAGTCCACGTTCTTTAATAGTGGACTCTTGTTCCAAACTGGAACAACACTCAACCCTATCT
CGGGCTATTCTTTTGATTTATAAGGGATTTTGCCGATTTCGGCCTATTGGTTAAAAAATGAGCTGATTTAACAAA
AATTTAACGCGAATTTTAACAAAATATTAACGTTTACAATTTTATGGTGCACTCTCAGTACAATCTGCTCTGATG
CCGCATAGTTAAGCCAGCCCCGACACCCGCCAACACCCGCTGACGCGCCCTGACGGGCTTGTCTGCTCCCGGCAT
CCGCTTACAGACAAGCTGTGACCGTCTCCGGGAGCTGCATGTGTCAGAGGTTTTCACCGTCATCACCGAAACGCG
CGAGACGAAAGGGCCTCGTGATACGCCTATTTTTATAGGTTAATGTCATGATAATAATGGTTTCTTAGACGTCAG
GTGGCACTTTTCGGGGAAATGTGCGCGGAACCCCTATTTGTTTATTTTTCTAAATACATTCAAATATGTATCCGC
TCATGAGACAATAACCCTGATAAATGCTTCAATAATATTGAAAAAGGAAGAGTATGAGTATTCAACATTTCCGTG
TCGCCCTTATTCCCTTTTTTGCGGCATTTTGCCTTCCTGTTTTTGCTCACCCAGAAACGCTGGTGAAAGTAAAAG
ATGCTGAAGATCAGTTGGGTGCACGAGTGGGTTACATCGAACTGGATCTCAACAGCGGTAAGATCCTTGAGAGTT
TTCGCCCCGAAGAACGTTTTCCAATGATGAGCACTTTTAAAGTTCTGCTATGTGGCGCGGTATTATCCCGTATTG
ACGCCGGGCAAGAGCAACTCGGTCGCCGCATACACTATTCTCAGAATGACTTGGTTGAGTACTCACCAGTCACAG
AAAAGCATCTTACGGATGGCATGACAGTAAGAGAATTATGCAGTGCTGCCATAACCATGAGTGATAACACTGCGG
CCAACTTACTTCTGACAACGATCGGAGGACCGAAGGAGCTAACCGCTTTTTTGCACAACATGGGGGATCATGTAA
CTCGCCTTGATCGTTGGGAACCGGAGCTGAATGAAGCCATACCAAACGACGAGCGTGACACCACGATGCCTGTAG
CAATGGCAACAACGTTGCGCAAACTATTAACTGGCGAACTACTTACTCTAGCTTCCCGGCAACAATTAATAGACT
GGATGGAGGCGGATAAAGTTGCAGGACCACTTCTGCGCTCGGCCCTTCCGGCTGGCTGGTTTATTGCTGATAAAT
CTGGAGCCGGTGAGCGTGGGTCTCGCGGTATCATTGCAGCACTGGGGCCAGATGGTAAGCCCTCCCGTATCGTAG
TTATCTACACGACGGGGAGTCAGGCAACTATGGATGAACGAAATAGACAGATCGCTGAGATAGGTGCCTCACTGA
TTAAGCATTGGTAACTGTCAGACCAAGTTTACTCATATATACTTTAGATTGATTTAAAACTTCATTTTTAATTTA
AAAGGATCTAGGTGAAGATCCTTTTTGATAATCTCATGACCAAAATCCCTTAACGTGAGTTTTCGTTCCACTGAG
CGTCAGACCCCGTAGAAAAGATCAAAGGATCTTCTTGAGATCCTTTTTTTCTGCGCGTAATCTGCTGCTTGCAAA
CAAAAAAACCACCGCTACCAGCGGTGGTTTGTTTGCCGGATCAAGAGCTACCAACTCTTTTTCCGAAGGTAACTG
GCTTCAGCAGAGCGCAGATACCAAATACTGTTCTTCTAGTGTAGCCGTAGTTAGGCCACCACTTCAAGAACTCTG
TAGCACCGCCTACATACCTCGCTCTGCTAATCCTGTTACCAGTGGCTGCTGCCAGTGGCGATAAGTCGTGTCTTA
CCGGGTTGGACTCAAGACGATAGTTACCGGATAAGGCGCAGCGGTCGGGCTGAACGGGGGGTTCGTGCACACAGC
CCAGCTTGGAGCGAACGACCTACACCGAACTGAGATACCTACAGCGTGAGCTATGAGAAAGCGCCACGCTTCCCG
AAGGGAGAAAGCGGACAGGTATCCGGTAAGCGGCAGGGTCGGAACAGGAGAGCGCACGAGGGAGCTTCCAGGGG
GAAACGCCTGGTATCTTTATAGTCCTGTCGGGTTTCGCCACCTCTGACTTGAGCGTCGATTTTTGTGATGCTCGT
CAGGGGGCGGAGCCTATGGAAAAACGCCAGCAACGCGGCCTTTTTACGGTTCCTGGCCTTTTGCTGGCCTTTTG
CTCACATGTTCTTTCCTGCGTTATCCCCTGATTCTGTGGATAACCGTATTACCGCCTTTGAGTGAGCTGATACCG
CTCGCCGCAGCCGAACGACCGAGCGCAGCGAGTCAGTGAGCGAGGAAGCGGAAGAGCGCCCAATACGCAAACCGC
CTCTCCCCGCGCGTTGGCCGATTCATTAATGCAGCTGGCACGACAGGTTTCCCGACTGGAAAGCGGGCAGTGAGC
GCAACGCAATTAATGTGAGTTAGCTCACTCATTAGGCACCCCAGGCTTTACACTTTATGCTTCCGGCTCGTATGT
TGTGTGGAATTGTGAGCGGATAACAATTTCACACAGGAAACAGCTATGACCATGATTACGAATTGATCCAAGCTT
ATCGATTTCGAACCCTCGACCGCCGGAGTATAAATAGAGGCGCTTCGTCTACGGAGCGACAATTCAATTCAAACA
AGCAAAGTGAACA
8638
```

SYSTEM FOR GENE TARGETING AND PRODUCING STABLE GENOMIC TRANSGENE INSERTIONS

The instant application is a 371 national phase application of PCT International Patent Application Number PCT US/03/35587, filed Nov. 7, 2003, which claims priority to German Application Number DE 102 51 918 A1, filed Nov. 7, 2002.

FIELD OF THE INVENTION

The invention relates to novel methods and techniques to produce transgenic, or genetically modified, organisms (transgenesis). The focus of the innovation is on manipulation techniques that allow for the targeting and the stable anchoring of homologous or heterologous DNA-sequences (in the following description referred to as: "transgene" or "gene-of-interest") into the genome of a target species. To achieve this goal, we have developed three different systems of transformation vectors that are capable of integrating a transgene into invertebrate and vertebrate organisms via transposon- or recombinase-mediated transformation events. In addition, following the germline transformation procedure, both systems make possible the physical deletion of mobile DNA-sequences, brought in with the vector, from the target genome and therefore to stabilize the gene-of-interest. Stable (genomic) transgene insertions are regarded to be an essential pre-requisite for the safe production of genetically modified organisms at a large industrial scale.

DESCRIPTION OF THE RELATED ART

Current state-of-the-art technology to produce genetically modified insect organisms relies on transposon-mediated germ-line transformation. This transformational technique is based on mobilizable DNA, i.e. transformation vectors derived from Class II transposable elements having terminal inverted sequences, which transpose via a DNA-mediated process (see Finnegan, D. J., 1989. Eucaryotic transposable elements and genome evolution. Trends Genet. 5, 103-107, and Atkinson, P. W., Pinkerton, A. C., Of3 Brochta, D. A., 2001. Genetic transformation systems in insects. Annu. Rev. Entomol. 46, 317-346, the contents of which are incorporated herein by reference). The two ends of such a transposable element carrying within all functional parts necessary and sufficient for in vivo mobilization are termed TransposonL (5' end) and TransposonR (3' end). Several different germ-line transformation systems have in common that a gene-of-interest/transgene originally located within a transgene construct is transferred into genomic DNA of germ-line cells of the target species. The transformation process is catalyzed by the transposase enzyme provided by a helper plasmid. This enzyme recognizes DNA target sites flanking the gene-of-interest/transgene and mobilizes the transgene into the genome of germ-line cells of the insect species. In addition, transformed DNA contains a marker gene that allows detection of successful germ-line transformation events (by producing a dominantly visible phenotype).

Transposon-mediated germ-line transformation systems are currently available for a diverse spectrum of insect species. Systems based on the P-element revolutionized the genetics of the vinegar fly *Drosophila melanogaster* (see Engels, W. R. (1996). P elements in *Drosophila*. Curr. Top. Microbiol. Immunol. 204, 103-123, the contents of which are incorporated herein by reference), but they were not applicable to non-drosophilid insect species because of the dependence of P-elements on *Drosophila*-endogenous host factors (see Rio, D. C. & Rubin, G. M. (1988). Identification and purification of a *Drosophila* protein that binds to the terminal 31-base-pair inverted repeats of the P transposable element. Proc. Natl. Acad. Sci. USA 85, 8929-8933, the contents of which are incorporated herein by reference). Therefore, insect species of medical or economic importance have been transformed using host factor-independent "broad host range" transposable elements (see Atkinson, P. W. & James, A. A. (2002). Germline transformants spreading out to many insect species. Adv. Genet. 47, 49-86, the contents of which are incorporated herein by reference). Germline transformation systems based on the transposable elements piggyBac (see U.S. Pat. No. 6,218,185; WO 01/14537; and Handler, A. M., McCombs, S. D., Fraser, M. J., Saul, S. H. (1998). The lepidopteran transposon vector, piggyBac, mediates germline transformation in the Mediterranean fruitfly. Proc. Natl. Acad. Sci. USA 95, 7520-7525, the contents of which are incorporated by reference herein), Hermes (see U.S. Pat. No. 5,614,398, the contents of which are incorporated herein by reference), Minos (see European Patent No. EP 0 955 364 A36, the contents of which are incorporated herein by reference) and mariner (see WO 99/09817, the contents of which are incorporated herein by reference) are currently state-of-the-art technology to genetically modify important pest or useful insect species including, for example, malaria transmitting anopheline or culicine mosquitoes (*Anopheles gambiae, Anopheles stephensi, Anopheles albimanus, Culex quinquefasciatus, Aedes aegypti*; see Catteruccia, F., Nolan, T., Loukeris, T. G., Blass, C., Savakis, C., Kafatos, F. C. & Crisanti, A. (2000). Stable germline transformation of the malaria mosquito *Anopheles stephensi*. Nature 405, 959-962, and Allen, M. L., O-3 Brochta, D. A., Atkinson, P. W. & Levesque, C. S. (2001). Stable, germ-line transformation of *Culex* quinquefasciatus (Diptera: Culicidae). J. Med. Entomol. 38, 701-710, and Coates J. C., Jasinskiene, N., Miyashiro, L. & James, A. A. (1998). Mariner transposition and transformation of the yellow fever mosquito, *Aedes aegypti*. Proc. Natl. Acad. Sci. USA 95, 3748-3751, and Jasinskiene, N., Coates, C. J., Benedict, M. Q., Cornel, A. J., Rafferty, C. S., James, A. A. & Collins, F. H. (1998). Stable transformation of the yellow fever mosquito, *Aedes aegypti*, with the Hermes element from the housefly. Proc. Natl. Acad. Sci. USA 95, 3743-3747, and Perera, O. P., Harrell, R. A., Handler, A. M. (2002) Germ-line transformation of the South American malaria vector, *Anopheles albimanus*, with a piggyBac/EGFP transposon vector is routine and highly efficient. Insect Mol. Biol., 11, 291-297, the contents of which are incorporated herein by reference), the Mediterranean fruit fly, *Ceratitis capitata* (see Handler, A. M., McCombs, S. D., Fraser, M. J., Saul, S. H. (1998). The lepidopteran transposon vector, piggyBac, mediates germline transformation in the Mediterranean fruitfly. Proc. Natl. Acad. Sci. USA 95, 7520-7525 and Loukeris, G. T., Livadaras, I., Arca, B, Zabalou, S. & Savakis, C. (1995). Gene transfer into the Medfly, *Ceratitis capitata*, with a *Drosophila hydei* transposable element. Science 270, 2002-2005, the contents of which are incorporated herein by reference) and the silkworm, *Bombyx mori* (see Tamura, T. et al. (2000). Germline transformation of the silkworm *Bombyx mori* L. using a piggyBac transposon-derived vector. Nat. Biotechnol. 18, 81-84, the contents of which are incorporated herein by reference). Moreover, the application potential of broad host range transposable elements is not restricted to insect species: mariner-derived transformation vectors have been shown to integrate stably into the germ-line of the nematode, *Caenorhabditis elegans* (see Bessereau, J.-L., Wright, A., Williams, D. C., Schuske, K., Davis, M. W. & Jorgensen, E. M. (2001). Mobilization of a *Drosophila* transposon in the *Caenorhabditis elegans* germ line. Nature 413, 7074, the contents of which are incorporated herein by reference), the zebrafish, *Danio rerio* (see Fadool J. M., Hartl, D. L. & Dowling, J. E. (1998). Transposition of the mariner element from *Drosophila mauritiana* in Zebrafish. Proc. Natl. Acad. Sci. USA 95, 5182-5186, the contents of which are incorporated herein by reference) and chicken, *Gallus* spp. (see Sherman, A., Dawson, A., Mather, C., Gilhooley, H., Li, Y., Mitchell, R., Finnegan, D. & Sang, H. (1998). Transposition of the *Drosophila* element mariner into the chicken germ line. Nat. Biotechnol. 16, 1050-1053, the contents of which are incorporated herein by reference).

In order to follow germ-line transformation success, both species-specific and species-independent transformation markers have been established (see Horn, C., Schmid, B. G. M., Pogoda, F. S. & Wimmer, E. A. (2002). Fluorescent transformation markers for insect transgenesis. Insect Biochem. Mol. Biol. 32, 1221-1235, the contents of which are incorporated herein by reference). Species-independent markers consist of a combination of a promoter sequence which is phylogenetically conserved and a gene for a fluorescent protein placed under control of such a promoter (for example, GFP [green fluorescing protein] and derivatives thereof, or DsRed [*Discosoma* species red fluorescing protein] (see Chalfie, M. Tu, Y., Euskirchen, G., Ward, W., Prasher, D. C. (1994). Green fluorescent protein as a marker for gene expression. Science 263, 802-805, and Matz, M. V., Fradkov, A. F., Labas, Y. A., Savitsky, A. P., Zaraisky, A. G., Markelov, M. L., Lukyanov, S. A. (1999). Fluorescent proteins from nonbioluminescent *Anthozoa* species. Nat. Biotechnol. 17: 969-973, the contents of which are incorporated herein by reference). Species-independent markers are advantageous over species-specific markers because they are directly applicable to different insect species (and other organisms). The polyubiquitin-promoter (see Patent Cooperation Treaty PCT WO 01/14537 A1 and Handler, A. M. & Harrell, R. A. (1999). Germline transformation of *Drosophila melanogaster* with the piggyBac transposon vector. Insect Mol. Biol. 8, 449-457, the contents of which are incorporated herein by reference) as well as the "3×P3"-promoter (see Patent Cooperation Treaty PCT WO 01/12667 A1 and Berghammer, A. J., Klingler, M., & Wimmer, E. A. (1999). A universal marker for transgenic insects. Nature 402, 370-371, the contents of which are incorporated herein by reference) linked to genes for fluorescent proteins have been used most widely for this purpose.

A transposon-independent technology aiming at targeting a gene-of-interest/transgene into the genome of cells relies on the principle of site-specific recombination. This is possible by using a recombinase enzyme and corresponding DNA target sites that are heterospecific. The steps are: First, incorporating into the genome by transposon-mediated transformation, a DNA cassette that is flanked by heterospecific recombinase target sites and contains a marker system for positive-negative selection. Second, recombinase-mediated targeting into the marked genomic locus the gene-of-interest, which is located within a plasmid and is flanked by the same heterospecific recombinase target sites. This principle has been described as RMCE or recombinase-mediated cassette exchange (see European Patent No. EP 0 939 120 A1 and Baer, A. & Bode, J. (2001). Coping with kinetic and thermodynamic barriers: RMCE, an efficient strategy for the targeted integration of transgenes. Curr Opin Biotechnol.12, 473-480 and Kolb, A. F. (2002). Genome engineering using site-specific recombinases. Cloning Stem Cells. 4, 65-80, the contents of which are incorporated herein by reference). The functionality of DNA cassette exchange systems has been demonstrated in different cell lines (comprising also murine embryonic stem cells) using the FLP-recombinase enzyme and heterospecific FRT target sites (see Schlake, T. & Bode, J. (1994). Use of mutated FLP recognition target (FRT) sites for the exchange of expression cassettes at defined chromosomal loci. Biochemistry 33, 12746-12751, and Seibler, J., Schübeler, D., Fiering, S, Groudine, M. & Bode, J. (1998). DNA cassette exchange in ES cells mediated by Flp recombinase: an efficient strategy for repeated modification of tagged loci by marker-free constructs. Biochemistry 37, 6229-6234, and European Patent No. EP 0 939 120 A1, the contents of which are incorporated herein by reference) as well as using the Cre-recombinase enzyme and heterospecific loxP target sites (see Kolb, A. F. (2001). Selection-marker-free modification of the murine beta-casein gene using a lox2272 [correction of lox2722] site. Anal Biochem. 290, 260-271.26), the contents of which are incorporated herein by reference). However, RMCE has not been applied to genetically modified invertebrate organisms thus far.

Limitations of Prior Art/Improvements Over Prior Art

Transposon-based plasmid vectors have proven to be efficient tools for producing genetically modified insects for research purposes, but so far only on a small laboratory scale. However, the mobile nature of DNA transposable elements will be disadvantageous when scaling up the production/rearing of genetically modified insects. Owing to potential re-mobilization, the stability of genomic transgene integrations cannot be assured and, connected to this issue, concerns relating to the safety of release of such genetically modified insects will be raised.

Stability of Genomic Transgene Integrations in Large Industrial Scale

The current state-of-the-art provides, typically, for random transposon vector integrations into the host genome. While this may be advantageous for functional genomics studies that use vector integrations to cause random mutations (e.g. for transposon-tagging and enhancer trapping), it is typically disadvantageous for the creation of transgenic strains for applied use where high fitness levels and optimal transgene expression are desired. This results from integrations that create mutations by insertion into genomic sites that eliminate or disrupt normal gene function that negatively effect viability, reproduction, or behavior. Genomic position effects also influence expression of transgenes, typically causing decreased expression and/or mis-expression of genes of interest and markers so that transformants may not be easily identified, and the desired transgene expression for application is not achieved. Thus, most transformation experiments require the screening of multiple transform ant strains for optimal fitness and transgene expression, and often such strains cannot be identified. An important improvement over the current state-of-the-art would be an efficient and routine system to target transgene integrations to specific and defined genomic sites that are known not to disrupt normal gene function and whose position effects are limited or well characterized.

Transgene integrations that negatively effect host strain fitness and reproduction also confer a selective disadvantage to the transformed organism in a population relative to wild type organisms. Thus, a selective advantage is provided to non-transformed organisms or transformants that have lost or relocated the transgene due to a re-mobilization event. Re-mobilization requires the activity of a transposase enzyme corresponding to, and acting upon, the transposon sequences flanking the genomic transgene. Although the transposase used for germ-line transformation usually is not encoded by the host species' genome, transposase introduction by symbiotic or infectious agents is possible, and cross-reactivity to related transposase enzymes that are genomically encoded cannot be excluded. Such cross-reactivities have been reported between the transposable elements Hermes, from *Musca domestica*, and hobo, from *Drosophila melanogaster*, that caused significant instablity of Hermes-flanked transgenes in hobo-containing *Drosophila* strains (see Sundararajan, P., Atkinson, P. W. & O'Brochta, D. A. (1999). Transposable element interactions in insects: crossmobilization of hobo and Hermes. Insect Mol. Biol. 8, 359-368, the contents of which are incorporated herein by reference). It should be noted that well-characterized families of transposable elements contain multiple members and the cross-reactivity of them is largely unknown to date (e.g. the mariner/Tc1 superfamily (see Hartl, D. L., Lohe, A. R. & Lozovskaya, E. R. (1997). Modern thoughts on an ancyent marinere: function, evolution, regulation. Annu. Rev. Genet. 31, 337-358, the contents of which are incorporated herein by reference). For these reasons, a transformation technology that excludes the possibility of transgene re-mobilization events a priori will provide a higher standard of transgene stability and will be superior to currently available technology.

Transgene instability resulting from vector remobilization will have several negative consequences. The first is loss or change in desired transgene expression. Secondly, strain breakdown will result after relocated transgenes can segregate freely in meiosis and selection pressure acts against transgene-carrying chromosomes. Research results on the stability of transgene insertions in insects, reared at an industrial scale, have not been reported thus far. However, data for insect strains selected by classical Mendelian genetics and carrying translocations are available (see Franz, G., Gencheva, E. & Kerremans, Ph. (1994). Improved stability of genetic sex-separation strains for the Mediterranean fruit fly, *Ceratitis capitata*. Genome 37, 72-82, the contents of which are incorporated herein by reference). When reared at an industrial scale, such translocation strains, constructed for the Mediterranean fruit fly (see Franz, G., Gencheva, E. & Kerremans, Ph. (1994). Improved stability of genetic sex-separation strains for the Mediterranean fruit fly, *Ceratitis capitata*. Genome 37, 72-82, the contents of which are incorporated herein by reference) suffered from instability. Recombination events causing reversion of the selected recessive trait were observed at a frequency of $10^{-3}$-$10^{-4}$ (see Franz, G. (2002). Recombination between homologous autosomes in medfly (*Ceratitis capitata*) males: type-1 recombination and the implications for the stability of genetic sexing strains. Genetica 116, 73-84, the contents of which are incorporated herein by reference). Because the recessive trait conferred a selective disadvantage to the individual insect, such reversion events caused strain breakdown rapidly. Most interestingly, these events were not observed at a small laboratory scale and therefore were not anticipated. As strain breakdown during a continuous industrial production of those insects is not acceptable, major research efforts have been made to improve the situation. Currently a laborious (and expensive) but efficient manual detection system for quality control has been implemented (see Fisher, K. & Caceres, C. (2000). A filter rearing system for mass reared medfly, S. 543-550 in *Area-wide control of fruit flies and other insect pests*, Ed.: Tan, K. H., Penerbit Universiti Sains Malaysia, Penang, Malaysia, the contents of which are incorporated herein by reference) and allows the successful production of this translocation strain at a scale of $10^6$-$10^7$ individuals per week (see Franz, G. (2002). Recombination between homologous autosomes in medfly (*Ceratitis capitata*) males: type-1 recombination and the implications for the stability of genetic sexing strains. Genetica 116, 73-84, the contents of which are incorporated herein by reference).

Safety Aspects Concerning Release of Genetically Modified Insects

Another important concern for remobilization is the potential for lateral transmission of the transgene into unintended host strains or species. Many industrial applications of insect transgene technology will include the release of genetically modified insects into the environment (e.g. the Sterile Insect Technique). Therefore, aspects of biosafety and ecological risk assessment will be of fundamental importance. Biosafety includes minimizing the risk of unintended transgene transmission from the host to other procaryotic or eucaryotic species during rearing or after release into the field. Horizontal gene transfer cannot be excluded per se, because the mechanisms of nucleic acid exchange between species are not sufficiently investigated to date. While most transposon vectors have their transposase source eliminated and are not self-mobilizable, functional autonomous transposons can be transmitted among species horizontally, and transposase may be provided to the vector by associated organisms or by a related enzyme in the host species. Thus, the risk for transgene vector re-mobilization by a transposase-mediated event can be most definitively eliminated when transposon sequences, required for germ-line transformation, are removed from the genomic integration after the transformation process. Systems disclosed in this patent application contribute to risk minimization by introducing techniques for transposon sequence removal. It is probable that, in the future, procedures to remove such sequences, and therefore to assure a higher standard of biosafety, will become an obligate precondition for permission by regulatory organizations for release of transgenic organisms. In fact, there are sound prospects that such systems will set the safety standards and will become normative which in turn demonstrates the commercial potential of the invention.

BRIEF SUMMARY OF THE INVENTION

The Strategy: Post-transformational Immobilization of Transgenes

Disadvantages stated in the previous section show the need for novel germ-line transformation systems that enable the stable integration of transgenes/genes-of-interest. The challenge is to develop a transformation method that prevents re-mobilization of transgenes which have been incorporated into the genome. The strategy disclosed in this patent application is to remove the intact transposon parts (containing transposase-recognition sites) following the transformation procedure (i.e. post-transformational). Three variants of this invention are disclosed as embodiments. These variants allow (i) modification of transgene DNA, (ii) post-transformational inactivation of at least one of the transposon parts and (iii) inactivation of at least one of the two transposon recognition sites required for re-mobilization by physical deletion from the genome.

The first embodiment disclosed has been termed "excision-competent stabilization vectors" (FIG. 1). This embodiment comprises a transformation vector that, in addition to currently applied vectors that contain solely a TransposonL1 half side and TransposonR1 half side (now referred to as TransposonL1 and R1), contains an additional internally-positioned TransposonL half side (referred to as TransposonL2 in FIG. 1) placed in-between the original Transposon L1 and R1 sides. L and R half sides are placed in the normal, or same, terminal inverted repeat orientation to one another as found in the original transposable element. Marker genes that can be distinguished from one another are placed in-between TransposonL1 and TransposonL2 and in-between TransposonL2 and TransposonR1. The steps of transformation are as follows. First, the transformation procedure is carried out according to the current state-of-the-art germ-line transformation technology that will result in individuals transformed by one of two possible events with this vector. One possible event is the integration of TransposonL1 and TransposonR1 and all intervening DNA including the two marker genes, TransposonL2, and other genes of interest. The second possible event is integration of TransposonL2 and TransposonR1 and all intervening DNA including the marker gene. For the purposes of this embodiment, only individuals transformed with TransposonL1 and TransposonR1, which are identified by expression of the two marker genes, are conserved for further experimentation. The internal vector containing TransposonL2 and TransposonR1, within TransposonL1 and TransposonR1, is then re-mobilized by introduction of a source of transposase derived from mating to a jumpstarter strain having a genomic transposase gene, or physical injection of the transposase DNA, RNA, or protein into embryos. Deletion by transposon excision of the TransposonL2 and TransposonR1 half sides is identified by loss of the intervening marker gene. The remaining TransposonL1 half-side, with the downstream marker gene and genes-of-interest, is identified by the single marker gene phenotype and verified by sequencing of amplified DNA. This remaining TransposonL1 half side, marker gene and genes-of-interest should be incapable of re-mobilization by transposase in the absence of the requisite TransposonR1 half side.

The second embodiment disclosed has been termed "conditional excision-competent transformation vectors" (FIG. 4). This embodiment comprises a modified excision-competent transformation vector that contains a transposonR2 half-side in an inverted orientation, relative to the R1 half side, with R2 also flanked by recombinase target sites in inverted orientation. In this configuration, only the TransposonL1 and R1 half-sides can integrate by transposition, and remobilization of the TransposonL1 and R2 half-sides can only occur after a recombinase-mediated inversion between the recombinase target sites. This modification will facilitate the stabilization process, by transposon L1 and R2 half-side deletion, for those excision-competent transformation vectors and/or host species where the primary transposition is highly favored or limited to the internal TransposonL1 and R2 half-sides if R2 was in a normal orientation.

A similar result is achieved by the third embodiment which has been termed "RMCE with subsequent transposon deletion" (FIG. 5). Completely new in this embodiment is a DNA targeting strategy. The ultimate germ-line transformation process is conducted as a recombinase-mediated process, instead of a transposase-mediated process, into an existing (and pre-defined) genomic target site. This involves the RMCE principle, i.e. a site-specific recombinase recognizes heterospecific DNA target sites and exchanges DNA-cassettes between a RMCE-acceptor and a RMCE-donor (step 1 in FIG. 5). The success of this cassette exchange is indicated by the exchange of the acceptor target marker gene (e.g. ECFP, see FIG. 7) by the donor vector marker gene (e.g. EYFP, see FIG. 7). It is important to stress that only the coding region of the transformation marker genes is exchanged, not the promoter regions (which are not present in the RMCE-donor plasmid). The advantage of this promoter-free exchange is that side-reactions, which involve non-targeted integration of the donor into the genome, will not be recognized. Most important to this first step of cassette exchange, is a "homing DNA sequence" that is present in both the RMCE-acceptor and the RMCE-donor and is identical in both functional parts. The homing DNA sequence functions to significantly enhance the cassette exchange efficiency. The principle of stably integrating a gene-of-interest via a RMCE strategy into the genome of an invertebrate organism is completely novel and extends previously described RMCE-technology (see European Patent No. EP 0 939 120 and Schlake, T. & Bode, J. (1994). Use of mutated FLP recognition target (FRT) sites for the exchange of expression cassettes at defined chromosomal loci. Biochemistry 33, 12746-12751, and Seibler, J., Schübeler, D., Fiering, S, Groudine, M. & Bode, J. (1998). DNA cassette exchange in ES cells mediated by Flp recombinase: an efficient strategy for repeated modification of tagged loci by marker-free constructs. Biochemistry 37, 6229-6234, and European Patent No. EP 0 939 120, the contents of which are incorporated herein by reference) to invertebrate organisms. Because the RMCE-acceptor also carries a transposon half-side (Transposon R1 in FIG. 5), a fully remobilizable internal transposon is reconstituted after a successful RMCE reaction. This reconstituted transposon is subsequently physically deleted from the organism's genome by the action of a transposase (step 2 in FIG. 5 and FIG. 7) exactly as described for the first embodiment. In conclusion, the gene-of-interest is only flanked by one transposon half side end and hence is immobilized because it does not provide a complete substrate for transposase-mediated mobilization.

BRIEF DESCRIPTION OF THE FIGURES

For a fuller understanding of the nature and objects of the present invention, reference should be made by the following detailed description taken with the accompanying figures, in which:

FIG. 1 shows a protocol for integration and re-mobilization for stabilized vector creation;

FIG. 2 shows a diagram of stabilization vector pBac{L1-PUbDsRed1-L2-3×P3-ECFP-R1};

FIG. 3 shows a PCR analysis and verification of pBac{L1-PubDsRed1-L2-3×P3-ECFP-R1} vector integration in line F34 and L2-3×P3-ECFP-R1 remobilization in line F34-1M (SEQ ID NOS 13-22, respectively in order of appearance);

FIG. 4 shows the principle of "conditional excision competent transformation vectors";

FIG. 5 shows the principle of "RMCE with subsequent transposon deletion";

FIG. 6 shows an embodiment of the principle as shown in FIG. 4

FIG. 7 shows an embodiment of the principle as shown in FIG. 5: Stabilized vector creation by RMCE;

FIG. 8 shows a diagram of RMCE acceptor vector;

FIG. 9 shows molecular analysis of RMCE acceptor and RMCE donor transgenic lines and PCR analysis of transgene mobilization (SEQ ID NOS 17, and 23-24, respectively in order of appearance);

FIG. 10 shows a diagram of a final RMCE donor vector for transgene stabilization;

FIG. 11 shows the approximate sequence of the vector shown in FIG. 2 (SEQ ID NO: 1);

FIG. 12 shows the approximate sequence of the vector shown in FIG. 8 (SEQ ID NO: 2); and FIG. 13 shows the approximate sequence of the vector shown in FIG. 10 (SEQ ID NO: 3).

DETAILED DESCRIPTION OF THE INVENTION

Embodiment 1

Excision-competent Stabilization Vectors

The experimental steps for the method are described in FIG. 1, and the structure of the excision competent transformation vector, pBac{L1-PUbDsRed1-L2-3×P3-ECFP-R1}, is described in FIG. 2. Integration and re-mobilization of the vector was verified by PCR and sequence analysis described in FIG. 3. pBac{L1-PUbDsRed1-L2-3×P3-ECFP-R1} was constructed based on the transposable element "piggyBac" (see U.S. Pat. No. 6,218,185, the contents of which are incorporated herein by reference). Conventional piggyBac-based transformation vectors (see WO 01/14537 and WO 01/12667, the contents of which are incorporated herein by reference) typically contain piggyBac-half sides or parts thereof, including 5' piggyBac terminal sequences (referred to as piggyBacL) and 3' piggyBac terminal sequences (referred to as piggyBacR), which flank a transformation marker gene and a cloning site to insert the genes-of-interest. (see Handler, A. M., 2001. A current perspective on insect gene transfer. Insect Biochem. Mol. Biol., 31, 111-128, the contents of which are incorporated herein by reference.) For vectors that are not autonomously transpositionally active, the transposase gene is partially deleted or interrupted by marker genes or genes-of-interest, thereby mutating the transposase. Non-autonomous vectors require an independent source of functional transposase for mobilization resulting in transposition. In contrast to conventional vectors, pBac{L1-PUbDsRed1-L2-3×P3-ECFP-R1} is provided with an additional piggyBacL half side (referred to as L2 half side) that is in the same orientation as the L1 half side, and positioned internal to the piggyBac L1 and R1 half sides. In this orientation, transposition can occur utilizing the L1 and R1 half sides, or the internal L2 and R1 half sides.

In addition, pBac{L1-PUbDsRed1-L2-3×P3-ECFP-R1} contains a unique KasI restriction endonuclease site in the piggyBacL1 region that can be used to insert genes of interest. In order to follow the primary transformation integration event of the L1 and R1 half-sides and to distinguish it from integration of L2 and R1 half-sides, independent transformation marker genes are placed in-between the two half-side pairs. In pBac{L1-PUbDsRed1-L2-3×P3-ECFP-R1}, the PUbDsRed1(see WO 01/14537, the contents of which are incorporated herein by reference) marker is placed in-between the L1 and L2 half sides, and the 3×P3-ECFP (see WO 01/12667, the contents of which are incorporated herein by reference) marker is placed in-between the L2 and R1 half sides.

pBac{L1-PUbDsRed1-L2-3×P3-ECFP-R1}:

A 3.7-kb AflIII-AflII fragment from pB[PUbDsRed1], containing 0.7 kb of piggyBac L1 half-side DNA and adjacent 5' insertion site DNA and the polyubiquitin:DsRed1 DNA gene, was blunted by Klenow-mediated nucleotide fill-in reaction and isolated by agarose gel purification. The blunted fragment was ligated into the MscI site of pXL-BacII-3×P3-ECFP. Plasmids having the 3×P3-ECFP and polyubiquitin:DsRed1 reading frames in opposite orientation were selected.

phspBac Transposase Helper Plasmid:

For germline transformation experiments, the helper phspBac was (see PCT WO 01/14537, the contents of which are incorporated herein by reference).

Experimental Steps of the Transgene Immobilization Process:

a) Germ-line Transformation with pBac{L1-PUbDsRed1-L2-3×P3-ECFP-R1}

The pBac{L1-PUbDsRed1-L2-3×P3-ECFP-R1} vector was integrated into the *Drosophila* genome of the white eye w[m] strain by coinjection with the phspBac helper plasmid into pre-blastoderm embryos. Using conventional piggyBac-mediated germ-line transformation methods (see U.S. Pat. No. 6,218,185 and WO 01/14537, the contents of which are incorporated herein by reference), seven putative G 1 transformant lines expressing only the 3×P3-ECFP marker were observed and discarded. One G1 male fly exhibited both thoracic expression of DsRed and eye expression of ECFP, and it was backcrossed to w[m] females to create a line designated as F34. Transformation by an intact pBac{L1-PUbDsRed1-L2-3×P3-ECFP-R 1} vector by piggyBac-mediated transformation in F34 was confirmed by sequencing of internal PCR products and inverse PCR products, derived from F34 genomic DNA, which provided the insertion site DNA sequence (see below).

b) piggyBac Transposase-Induced Excision of piggyBacL2 and piggyBacR1

Transformed individuals identified and confirmed to have the marker genes 3×P3-ECFP and PUbDsRed1 were backcrossed to w[m] flies for two generations. The presence of both markers solely in female progeny from F34 parental males indicated X-chromosome sex-linkage for the primary integration. F34 flies were mated as transgene heterozygotes to a piggyBac jumpstarter strain (w+/Y;pBac/pBac;+/+) having a homozygous P-element-mediated integration of an hsp70-regulated piggyBac transposase gene into chromosome 2 and marked with the wild type white+ allele. Larval and pupal offspring of these matings were heat shocked at 37° C. for 60 minutes every second day until adult emergence to promote transposase gene expression. Male and female progeny of these matings were screened, with those carrying the transposase gene (red eye pigmentation) and expressing the fluorescent protein markers, PUb-DsRed1 and 3×P3-ECFP, being mated to w[m] individuals. Ten matings of 4 to 5 appropriately marked females to w[m] males and 18 matings of 2 to 3 marked males to w[m] females were set up. Progeny from these matings were screened for expression of PUb-DsRed1 and the absence of 3×P3-ECFP, which would indicate loss by remobilization of the piggyBacL2 and piggyBacR1 half sides with the intervening 3×P3-ECFP marker DNA. Progeny expressing only DsRed1 fluorescence were detected at an approximate frequency of 2% of all flies screened. A single white eye male (lacking the transposase gene) and expressing DsRed1 and not ECFP, was outcrossed to w[m] females with the resultant line designated as F34-1M.

c) Molecular Analysis of the Vector Integration Before and After Remobilization

The pBac{L1-PUbDsRed1-L2-3×P3-ECFP-R1} integration into the F34 *Drosophila* genome was initially identified by phenotypic expression of the DsRed and ECFP marker genes and verified by PCR amplication of transformant DNA using primers internal to the vector sequence (see FIG. 3). Genomic insertion site DNA flanking the integration was obtained by inverse PCR of the piggyBacL1 5'-end half side using the 122R and 139F primers, in outward orientation, to F34 genomic DNA digested with MspI endonuclease and circularized by ligation. The 5'end insertion site sequence was compared by BLAST analysis to the *Drosophila* Genome Sequence Database, and consistent with segregation analysis, was found to be homologous to sequence found on the X-chromosome at locus 9B4. The database sequence was used to derive the piggyBacR1 3'-end insertion site, and the 197F and 196R PCR primers were created to genomic insertion site DNA at the 5' and 3'-end flanking sequences, respectively. The genomic primers were then used to amplify and sequence DNA that spans the pBac{L1-PUbDsRed1-L2-3×P3-ECFP-R1 } integration in F34, to further verify it as a primary intact piggyBac vector integration. The 197F and 196R primers were then used for PCR of F34-1M genomic DNA, which confirmed remobilization of the L2-PUbDsRed1-R1 internal vector DNA in F34. Further verification of the vector integration and subsequent re-mobilization was achieved by sequencing of PCR products obtained with primers 196 and 197 in combination with primers to internal vector DNA described in FIG. 3. In all cases, positive PCR results yielded sequences consistent with a primary integration of pBac{L 1-PubDsRed 1-L2-3×P3-ECFP-R1 } in F34, and remobilization of the L2-PUbDsRed1-R1 sequence in F34-1M flies. PCR products were not obtained in F34-1M flies using primers to the L2-PUbDsRed1-R1 sequence consistent with its deletion from the genomic DNA after re-mobilization.

Embodiment 2

Conditional Excision-competent Transformation Vectors

The structure of the conditional excision-competent transformation vector, pBac_STBL, as well as the experimental steps are depicted schematically in FIGS. 4 and 6. pBac_STBL is based on the transposable element "piggyBac" (see U.S. Pat. No. 6,218,185, the contents of which are incorporated herein by reference) and is a modified version of pBac{L1-PUbDsRed 1-L2-3×P3-ECFP-R1 }. In pBac-STBL the internal transposon half-side (R2) is a duplication of the piggyBac 3'-end, and it is in reverse, or opposite, orientation to R1. In addition, it is flanked in upstream and downstream positions by FRT (FLP recombinase target) sites in opposite directions that create an inversion by recombination in the presence of FLP recombinase (see FIGS. 4 and 6). Therefore, in this vector, only the piggyBacL1 and R1 half sides and intervening DNA can integrate, but re-mobilization of piggyBacR2 together with piggyBacL1 or piggyBacR1 should not be possible. Mobilization of piggyBacR2 and L1 is only possible after FRT recombination.

In addition, pBac_STBL contains unique cloning sites for the rare octamer-specific restriction enzymes AscI and FseI. pBac_STBL is equipped with two separable transformation marker genes (see WO 01/12667, the contents of which are incorporated herein by reference), which are located upstream of the AscI/FseI cloning sites (3×P3-EYFP; FIG. 6) and downstream of the FRT-sites (3×P3-DsRed; FIG. 6), respectively. In the following, the details of pBac_STBL plasmid construction starting from plasmid vectors already published are disclosed:

pSL-3×P3-DsRedaf:
A 0.8 kb SalI-NotI fragment from pDsRed1-1 (Clontech, Palo Alto, Calif.) is cloned into the plasmid pSL-3×P3-EGFPaf (see WO 01/12667, the contents of which are incorporated herein by reference) previously digested with SalI-NotI. Thereby, the EGFP (0.7 kb) open reading frame was replaced by the DsRed (0.8 kb) open reading frame.

pSLfaFRTfa:
The FRT sequence (90bp) is prepared by SalI-Asp718 restriction of pSL>AB> and cloned into the plasmid pSLfa1180fa previously digested with XhoI-Asp718. The FRT sequence corresponds to the substrate of the FLP recombinase:

TTGAAGTTCCTATTCCGAAGTTCCTATTCTCTAGAAAGTATAGGAACTTC AGAGCGCTTTTGAAGCT(SEQ ID NO: 4)

pSL-3×P3-DsRed-FRT:
A 1.0 kb EcoRI-BsiWI fragment from pSL-3×P3-DsRedaf (containing the DsRed-ORF under 3×P3 promoter control) is cloned into pSLfaFRTfa previously digested with EcoRI-Asp718.

pSL-3×P3-DsRed-FRT-FRT:
The PCR amplification product of the FRT sequence (template: pSL>AB>; Primers: CH_FRT_F 5'-GAGCT-TAAGGGTACCCGGGGATCTTG -3'(SEQ ID NO: 5) and CH_FRT_R 5'-GACTAGTCGATATCTAGGGCCGC-CTAGCTTC-3'(SEQ ID NO: 6)) is digested with BfrI-SpeI and cloned into pSL-3×P3-DsRed-FRT previously digested with BfrI-SpeI. Both FRT sequences are oriented in opposite directions.

pSL-3×P3-DsRed-FRT-pBacR2-FRT:
The piggyBac 3' sequence (referred to as: piggyBacR2) is prepared as a 1.3 kb HpaI-EcoRV fragment from the plasmid p3E1.2 (see U.S. Pat. No. 6,218,185, the contents of which are incorporated herein by reference) and cloned into the plasmid pSL-3×P3-DsRed-FRT-FRT previously cut with EcoRV. The piggyBacR2 insertion with an orientation opposite to the DsRed-ORF is chosen (the EcoRV cloning site is restored at the 5'end of the insertion).

pBac_STBL:
A 2.7 kb EcoRI-BfrI fragment (both restriction sites filled in by Klenow reaction) from pSL-3×P3-DsRed-FRT-pBacR2-FRT is cloned into pBac-3×P3-EYFPaf (see WO 01/12667, the contents of which are incorporated herein by reference) previously cut with BglII (Klenow fill-in reaction). The insertion with an opposite orientation of the DsRed- and EYFP-ORFs is chosen. This final plasmid contains piggy-BacR2 in opposite orientation to piggyBacR1 (FIG. 6).

phspBac Transposase Helper Plasmid:
For germline transformation experiments, the helper phsp-Bac is used (see PCT WO 01/14537, the contents of which are incorporated herein by reference).

Experimental Steps of the Transgene Immobilization Process (FIG. 4 and FIG. 6)
a) Germline Transformation of pBac_STBL (Step 1 in FIG. 4 and FIG. 6)
DNA-sequences included in the plasmid pBac_STBL within the ends of piggyBacL1 and piggyBacR1 are integrated into the Drosophila genome by piggyBac-mediated germline transformation (see U.S. Pat. No. 6,218,185 and WO 01/14537, the contents of which are incorporated herein by reference). Similar constructs incorporating genes-of-interests inserted at the unique cloning sites would be treated in the same way.
b) FLP Recombinase Induced Inversion (Step 2 in FIG. 4 and FIG. 6)
Genomic integrations of the pBac_STBL transgene are identifiable by both EYFP and DsRed eye fluorescence (see WO 01/12667, the contents of which are incorporated herein by reference). Following the identification of transgenic founder individuals (and to establish Drosophila strains carrying the transgene in the homozygous state), the inversion of the piggyBacR2 sequence is carried out. This is performed by crossing in the strain beta2t-FLP that expresses FLP-recombinase during spermatogenesis. Alternatives of step 2 in FIG.

6 include crossing in hsp70-FLP and hsFLP-strains, respectively, or microinjection of a FLP-recombinase encoding plasmid, e.g. pKhsp82-FLP (into preblastoderm embryos of homozygous transgenic pBac_STBL lines). Though the inversion event cannot be detected by the marker genes included into pBac_STBL, a statistical equilibrium of original and inverted orientation of the piggyBacR1 sequence can be assumed. Thus, the inversion process is detected by testing several independent sublines by sequencing of vector PCR products to identify sublines having undergone piggyBacR1 inversion.

c) piggyBac Transposase Induced Deletion (Step 3 in FIG. 4 and FIG. 6)

Strains with inverted piggyBacR2 sequence are crossed to piggyBac transposase expressing strains (referred to as jumpstarter). Different lines of the *Drosophila* strain Her{3×P3-ECFP, alphaltub-piggyBacK10} are available for this step. Progeny from this cross expressing both EYFP/DsReD (indicating the presence of pBac_STBL) and ECFP (indicating the presence of the jumpstarter) are crossed out in single male setups.

d) Identification of Immobilized Transgene DNA

ECFP⁻ progeny (selection against the jumpstarter) of single male crossings are analyzed for both the presence of EYFP fluorescence and the absence of DsRed fluorescence. Individuals putatively containing a transposon deletion event should show EYFP but absence of DsRed fluorescence and can be analyzed further. By inverse PCR, the transposon deletion can be molecularly confirmed and stability of the potentially immobilized transgene insertion can be assessed by challenging the transgene insertion with piggyBac transposase.

Embodiment 3

RMCE with Subsequent Transposon Deletion

The RMCE-acceptor plasmid, pBac{3×P3-FRT-ECFP-linotte-FRT3} (FIG. 8), is a piggyBac-based transformation vector that was provided additionally with a DNA exchange cassette. This cassette consists of two heterospecific FRT sites (referred to as FRT and FRT3 equivalent to F and F3 (published in European Patent No. EP 0 939 120 A1, the contents of which are incorporated herein by reference)) in parallel orientation.

European Patent No. EP 0 939 120 A1 (see page 2, line 50 to page 3, line 6) teaches the technology of the RMCE reaction:

"Recombinases such as FLP and Cre have emerged as powerful tools to manipulate the eucaryotic genome (Kilby, N. J., Snaith, M. R., Murray, J. A. H. (1993). Site-specific recombinases: tools for genome engineering. Trends Genet. 9, 413-421, and Sauer B. (1994). Site-specific recombination: developments and applications. Curr. Opin. Biotechnol. 5, 521-527, the contents of which are incorporated by reference herein). These enzymes mediate a recombination between two copies of their target sequence and have mainly been used for deletions. We show here that FLP-RMCE can be applied to introduce secondary mutations at a locus which has been previously tagged by a positive/negative selectable marker, and that these secondary mutations can be produced without depending on a selectable marker on the incoming DNA. FLP-RMCE utilizes a set of two 48 bp FLP target sites, in this case wild type (F) and F3, a mutant that was derived from a systematic mutagenesis of the 8 bp spacer localized between the FLP binding elements (see Schlake T., Bode, J. (1994). Use of mutated FLP recognition target (FRT) sites for the exchange of expression cassettes at defined chromosomal loci. Biochemistry 33, 12746-12751, the contents of which are incorporated by reference herein). FLP effects recombination between the F3/F3 couple which is as efficient as between the wild type sites (F/F) but it does not catalyze recombination between a F/F3 pair (Seibler J., Bode J. (1997). Double-reciprocal crossover mediated by FLP-recombinase: a concept and an assay. Biochemistry 36, 1740-1747, the contents of which are incorporated by reference herein). Thereby FLP-RMCE enables the specific exchange of an expression cassette in the genome which is flanked by a F3-site on one end and a F-site on the other for an analogous cassette comprising virtually any sequence which is provided on a plasmid in a single step without the need of introducing a positive selectable marker. Nothing else in the genome is altered and no plasmid sequences are inserted. In contrast to approaches using a single recombination site the targeting product is stable even under the permanent influence of the recombinase unless it is exposed to an exchange plasmid (Seibler J., Bode J. (1997). Double-reciprocal crossover mediated by FLP-recombinase: a concept and an assay. Biochemistry 36, 1740-1747, the contents of which are incorporated by reference herein). The system can be used to analyze the function of either a gene product or of regulatory sequences in ES-cells or of the derived transgenic mice." (citations added)

In the present invention, FRT and FRT3 flank the ECFP open reading frame and a "homing sequence". As a "homing sequence", the 1.6 kb HindIII fragment of the *Drosophila* linotte locus was chosen (see Taillebourg, E. & Dura, J. M. (1999). A novel mechanism for P element homing in *Drosophila*. Proc. Natl. Acad. Sci. USA 96, 6856-6861, the contents of which are incorporated herein by reference. This particular sequence has been described to act as "bait" for homing of identical/homologous DNA sequences by a process called "para-homologous pairing". We have shown previously that the positioning of the FRT site between the 3×P3 promoter and the start codon of the ECFP open reading frame does not interfere with expression of the 3×P3-ECFP gene (see PCT WO 01/12667, the contents of which are incorporated herein by reference). The RMCE donor plasmid, pSL-FRT-EYFP-pBacR2-3×P3-DsRed-linotte-FRT 3 (FIG. 10), contains the DNA cassette to be recombined in. The donor cassette comprises the two heterospecific FRT sites (FRT and FRT3) flanking the EYFP open reading frame (promoter-free), a piggyBacR2 3'-half side sequence, the transformation marker gene 3×P3-DsRed and the homing sequence from the linotte locus (identical to the linotte sequence in the RMCE acceptor). The RMCE donor plasmid is a derivative of the plasmid pSLfa1180fa (see Patent Cooperation Treaty PCT WO 01/12667 A1), which does not contain any transposon sequences. AscI/FseI cloning sites have been incorporated to ease the insertion of gene(s)-of-interest upstream of the piggyBacR2 sequence.

In the following, the details of the RMCE plasmids construction starting from plasmid already published are disclosed:

Construction of the RMCE Acceptor Plasmid (FIG. 8):

pSL-3×P3-FRT-ECFPaf:

A 90 bp SalI-Asp718 fragment from the plasmid pSL>AB> containing the FRT sequence was cloned into the plasmid pSL-3×P3-ECFPaf (see Patent Cooperation Treaty PCT WO 01/12667, the contents of which are incorporated herein by reference) previously digested with SalI-Asp718. The FRT sequence corresponds to the substrate of the FLP recombinase:

TTGAAGTTCCTATTCCGAAGTTCCTATTCTCTAGAAAGTATAGGAACTTCAGAGCGCTTTTGAAGCT (SEQ ID NO: 4)

pBac{3×P3-FRT-ECFPaf}:

A 1.3 kb EcoRI-(blunted by Klenow fill in reaction)-NruI fragment from the plasmid pSL-3×P3-FRT-ECFPaf was cloned into the plasmid p3E1.2 previously digested with HpaI.

pBac{3×P3-FRT-ECFP-linotte-FRT}, Final RMCE Acceptor Plasmid:

The plasmid pBac {3×P3-FRT-ECFPaf} was digested with AscI-Bg/II, and the following sequences were cloned into the linearized vector:

i.) the AscI-Asp718 cut PCR amplification product of the 1.6 kb HindIII genomic linotte fragment. As a template, genomic DNA of *Drosophila melanogaster*, strain OregonR, was chosen and as primers:

```
CH_lioFwd
(5'-TTGGCGCGCCAAAAGCTTCTGTCTCTCTTTCTG-3')
(SEQ ID NO: 7)
and

CH_lioRev
(5'-CGGGGTACCCCAAGCTTATTAGAGTAGTATTCTTC-3')
(SEQ ID NO: 8)
``` and ii.) the Asp718-Bg/II cut PCR amplifcation product of the FRT3 sequence (mutagenic PCR). As a template, the plasmid pSL>AB> was chosen and as primers:

```
CH_F3Fwd
(5'-TTGGCGCGCCAAGGGGTACCCGGGGATCTTG-3')
(SEQ ID NO: 9)
and

CH_F3Rev
(5'-CCGCTCGAGCGGAAGATCTGAAGTTCCTATACTATTTGAAGAATA
G-3')(SEQ ID NO: 10).
```

The FRT3 sequence corresponds to the F3 sequence (European Patent No. EP 0 939 120 A1):

TTGAAGTTCCTATTCCGAAGTTCCTATTCTtcAaAtAGTATAGGAACTTCAGAGCGC(SEQ ID NO: 11)

The diagram of this final RMCE acceptor vector is shown in FIG. 8.

Construction was analogous to pSL-3×P3-FRT-ECFPaf, but into the plasmid pSL-3×P3-EYFPaf (see WO 01/12667, the contents of which are incorporated herein by reference).

pSL-FRT-EYFPaf:

The 3×P3 promoter sequence was deleted from the plasmid pSL-3×P3-FRT-EYFPaf by digestion with EcoRI-BamHI, filling-in by Klenow enzyme reaction and finally religating the blunted plasmid.

pSL-FRT-EYFP-linotte-FRT3:

A 1.7 kb AscI-BglII (both sites blunted by Klenow fill-in reaction) fragment from pBac{3×P3-FRT-ECFP-linotte-FRT 3} was cloned into the plasmid pSL-FRT-EYFPaf previously digested with NruI. The orientation with maximal distance of the FRT and FRT3 sites was chosen.

pBac{3×P3-DsRedaf}:

A 1.2 kb EcoRI (site blunted by Klenow fill-in reaction)-NruI fragment from the plasmid pSL-3×P3-DsRedaf was cloned into the plasmid p3E1.2 (see U.S. Pat. No. 6,218,185, the contents of which are herein incorporated by reference) previously digested with BglII-(site blunted by Klenow fill-in reaction)-HpaI.

pSL-FRT-EYFP-linotte-FRT3-3×P3-DsRed:

A 1.25 kb EcoRI-(site blunted by Klenow fill-in reaction)-NruI fragment from pSL-3×P3-DsRedaf was cloned into the plasmid pSL-FRT-EYFP-linotte-FRT3 previously digested with SpeI (site blunted by Klenow fill-in reaction).

pSL-FRT-EYFP-pBacR-3×P3-DsRed-linotte-FRT3, Final RMCE Donor Plasmid:

A 2.5 kb AscI-(site blunted by Klenow fill-in reaction)-EcoRV fragment from pBac{3×P3-DsRedaf} was cloned into the plasmid pSL-FRT-EYFP-linotte-FRT3 previously cut with EcoRI (site blunted by Klenow fill-in reaction).

The diagram of this final RMCE acceptor vector is shown in FIG. 10.

FLP Recombinase Plasmid Source: pKhsp82-FLP:

A 2.2 kb Asp718-XbaI (sites blunted by Klenow fill-in reaction) fragment from the plasmid pFL124 containing the FLP recombinase ORF and the 3' transcriptional terminator from the adh gene was cloned into the plasmid pKhsp82) previously cut with BamHI (site blunted by Klenow fill-in reaction).

phspBac Transposase Helper Plasmid:

For germ-line transformation experiments, the helper phspBac was used (see PCT WO 01/14537 A1).

DNA Cassette Exchange by RMCE is Highly Efficient in *Drosophila melanogaster*

Practical application of RMCE-based gene targeting and germline transformation (e.g. for the purpose of immobilizing transgenes) will depend strongly on the efficiency of the DNA cassette exchange. This efficiency should be in the range observed with conventional transposon-mediated germline transformation systems that allow the isolation of several transgenic founder individuals among 1,000-10,000 progeny screened. Previous experiments involving DNA cassette exchange have been performed only using cell culture and stringent selection conditions. Therefore the efficiency of such a system in an invertebrate organism such as *Drosophila* is hard to predict. Hence, a pilot experiment was performed. An intermediate of the RMCE donor plasmid, pSL-FRT-EYFP-linotte-FRT3 and the FLP recombinase expression vector pKhsp82-FLP were co-injected into pre-blastoderm embryos of a *Drosophila melanogaster* acceptor strain. These embryos carry the RMCE acceptor transgene vector (FIG. 8) integrated by piggyBac-mediated germ-line transformation, in a homozygous state. The final concentration of the plasmids in the injection mix was 500 ng/µl (RMCE donor plasmid) and 300 ng/µl (pKhsp82-FLP). Altogether, around 3,000 *Drosophila* embryos were injected, corresponding to ten times the number necessary for a conventional piggyBac-mediated germ-line transformation. Successful exchange of the acceptor by the donor cassette was indicated by the change in the eye fluorescence from ECFP to EYFP (in F1 individuals). Results documenting the frequency of such exchange events are given in Table 1:

TABLE 1

Results of the RMCE experiment in *Drosophila* with the donor plasmid pSL-FRT-EYFP-linotte-FRT3. Acceptor lines (II: second, III: third chromosomal homozygous, ECFP fluorescence) used for microinjection, number of injected embryos, male and fertile male injection survivors and the number of vials containing EYFP-positive progeny are given. EYFP-positive founder males resulting from targeting events were bred to homozygosity and established as stocks (referred to as "M4.II EYFP", "M7.III EYFP", "M8.II EYFP" and "M9.II EYFP", respectively). Segregation analysis (genetic mapping of transgene integrations) indicated for all four lines that the chromosomal localization of the donor and acceptor transgene is identical.

| Acceptor Line | Injected Embryos | Male Injection Survivors | Fertile Male Inj. Surv. | Vials with EYFP-pos. and ECFP-neg. progeny |
|---|---|---|---|---|
| M4.II ECFP | 750 | 121 | 70 | 22 |
| M7.III ECFP | 750 | 138 | 72 | 17 |
| M8.II ECFP | 600 | 68 | 54 | 12 |
| M9.II ECFP | 750 | 123 | 109 | 27 |

We define the DNA cassette exchange frequency as a percentage of fertile $F_1$ vials producing EYFP-positive progeny. With this definition, the frequency of RMCE events is 25% on average corresponding well to the germ-line transformation frequency usually observed with piggyBac, Hermes or Minos-based vectors in *Drosophila*). This experiment demonstrates that, with the particular design of RMCE-vectors, the process of cassette exchange is highly efficient in an invertebrate organism such as *Drosophila*.

Molecular Characterization of RMCE Events and Integration Site Analysis a) Genomic integration site of donor and acceptor transgenes The exchange of eye fluorescence from ECFP to EYFP suggests that the donor cassette (carrying the promoter-free eyfp gene) integrated at the locus of the acceptor transgene (providing the 3×P3 promoter). Therefore, the genomic integration sites of the acceptor transgene in the acceptor line and of the donor transgene in the corresponding donor line should be identical. To identify genomic integration sites, inverse PCR experiments were carried out for acceptor and donor *Drosophila* lines. To recover DNA sequences flanking piggyBac insertions, inverse PCR was performed. The purified fragments were directly sequenced for the 5' junction with primer CH_PLSeq 5'-CGGCGACTGAGATGTCC-3'(SEQ ID NO: 12). The obtained sequences were used in BLAST searches against the *Drosophila* Genome Sequence Database. For the 5'junction, genomic DNA sequence identity could be confirmed for three acceptor/donor pairs (Table 2).

TABLE 2

Genomic integration sites of the acceptor transgene pBac{3xP3-FRT-ECFP-linotte-FRT3} in four *Drosophila* lines used for RMCE targeting. Sequence numbers and nucleotide positions refer to the Release 3 sequence of the *Drosophila* Genome Sequence Database. For three corresponding RMCE donor lines, integration sites could be confirmed to be identical.

| Acceptor line | Location of insert | | | | Identical for corresponding donor line? |
|---|---|---|---|---|---|
| | Chromosome | | | | |
| | arm | genomic | scaffold | position | |
| M4.II ECFP | 2L | AE003662.3 | 204692 | yes | (M4.II EYFP) |
| M7.III ECFP | 3L | AE003558.3 | 171057 | yes | (M7.III EYFP) |
| M8.II ECFP | 2L | AE003618.2 | 15414 | yes | (M8.II EYFP) |
| M9.II ECFP | 2L | AE003662.3 | 15805 | nd. | | nd.: not determined

Interestingly, the acceptor line M9.II ECFP was found to carry the acceptor transgene integrated at the *Drosophila*-endogenous linotte locus (integration position corresponds to bp 1185). This suggests that "para-homologous pairing" of the linotte sequences included in the acceptor plasmid to the homologous genomic sequence occurred, further verifying the homing phenomenon.

b) Southern Analysis

To further verify at the molecular level that the donor transgene targeted the acceptor locus via an RMCE mechanism, Southern analysis on genomic DNA of the four acceptor and the four donor lines was performed. PstI was chosen as an indicative restriction digest and a probe hybridizing to gfp-based transformation marker genes (hybridizing to both ECFP and EYFP) was selected (FIG. 9). Only one strong hybridization signal was present in all acceptor lines which is consistent with a single integration of the acceptor transgene. The expected pattern of DNA-DNA hybridization, 2.4 kb for the acceptor transgene and 1.6 kb for the donor transgene, was detected for all four lines for each transgene (FIG. 9). Additionally, a ~6 kb hybridization signal was detected only in RMCE donor lines. As this signal might indicate the presence of the complete donor vector, further Southern experiments (using probes against the pUC plasmid backbone sequences) were carried out. The presence of pUC sequence in the donor lines could be confirmed (data not shown) pointing toward an integration of the entire donor vector in the four donor lines analyzed.

In summary, three lines of evidence let us infer that targeting of the RMCE acceptor locus by the RMCE donor vector took place: i) the exchange in eye color fluorescence from ECFP (acceptor) to EYFP (donor), ii) the identity of genomic DNA sequence flanking the piggyBac transgene integration in corresponding acceptor and donor lines, and iii) DNA hybridization signals in accordance with expectations for the exchange of the ecfp to the eyfp open reading frame.

Recombination Occurs by Cassette Exchange Via FRT and FRT3

The recombinase-mediated cassette exchange mechanism requires a double recombination event (see European Patent No. EP 0 939 120, the contents of which are incorporated herein by reference). Because the Southern analysis suggests that in the pilot RMCE experiments single recombination events caused integration of the entire donor plasmid, we analyzed in more detail whether the RMCE mechanism, which has not been established for an invertebrate organism, can occur in *Drosophila*. To this end, we modified the donor construct to include a 3×P3-DsRed marker gene downstream to the FRT3 sequence (pSL-FRT-EYFP-linotte-FRT3-3×P3-DsRed). This vector configuration allows the separation of RMCE events:
1) double cross-over via FRT and FRT3 sites resulting in ECFP to EYFP eye fluorescence exchange
2) single recombination events (via FRT site) resulting in ECFP to EYFP and DsRed eye fluorescence exchange
3) single recombination events (via FRT3 site) resulting in ECFP to DsRed (and ECFP) eye fluorescence exchange For the targeting experiment, the acceptor line M4.II ECFP (Table1) was selected for further testing. F1 individuals with ECFP to EYFP exchange indicating targeting were observed at a frequency of 13.1%:
Embryos injected: 750
single G0 male founders: 109
Fertile G0 male founders: 84
Setups producing EYFP-fluorescing F1 progeny: 11

The eleven setups yielding EYFP-fluorescing individuals were analyzed for the occurrence of double and single recombination events (Table 3).

TABLE 3

Phenotypic analysis of F1 progeny from G0 male founders of the acceptor line M4.II ECFP injected with the donor pSL-FRT-EYFP-linotte-FRT3-3×P3-DsRed. Double and single recombination events are indicated by differential analysis of eye fluorescence for ECFP, EYFP and DsRed.

| Setup# | Phenotype of individual flies | | | |
|---|---|---|---|---|
| | double recombination EYFP$^+$ (DsRed$^-$, ECFP$^-$) | single FRT rec. EYFP$^+$, DsRed$^+$ (ECFP$^-$) | single FRT3 rec. DsRed$^+$, ECFP$^+$ (EYFP$^-$) | established Stocks |
| 1 | 1 | 1 | 0 | |
| 2 | 1 | 0 | 0 | R1 |
| 3 | 2 | 6 | 0 | |
| 4 | 4 | 0 | 0 | R2 |
| 5 | 3 | 0 | 0 | R3 |
| 6 | 3 | 0 | 0 | R4 |
| 7 | 1 | 10 | 0 | R5 (EYFP$^+$, DsRed$^+$) |
| 8 | 13 | 26 | 0 | R6 (EYFP$^+$, DsRed$^+$) |
| 9 | 1 | 2 | 0 | |
| 10 | 11 | 3 | 0 | |
| 11 | 1 | 0 | 0 | |

Five out of eleven setups produced progeny showing EYFP but lacking DsRed (and ECFP) fluorescence. This phenotype is consistent with targeting via double recombination with only sequences between FRT and FRT3 being exchanged. However, single recombination events via FRT were also observed, in contrast to no single recombinations via FRT3. The results indicate that recombinase mediated cassette exchange is mechanistically feasible in an invertebrate organism (the vinegar fly Drosophila melanogaster) and, by applying a simple eye fluorescence marker scheme, double recombination events can be selected for.

Experimental Steps of the Transgene Immobilization Process (FIG. 5 and FIG. 7)

The previous results demonstrate that recombinase mediated targeting of genomic DNA loci is possible in an invertebrate organism like Drosophila. As depicted in FIG. 5, the RMCE strategy can be further employed for the purpose of post-transformational transgene immobilization. The general procedure consists of two steps. In the first step, a transformation vector containing the gene of interest, a transposon half-side (TransposonR2 in FIG. 5) and an additional marker gene is used as the RMCE donor to target the RMCE acceptor line (i.e. RMCE acceptor vector (FIG. 8) genomically integrated). By a single or double recombination event, an 'internal' piggyBac transposon comprising both half-sides (piggyBacL1 and piggyBacR2 in FIG. 5) is reconstituted. In a second step, transposase activity is introduced to remobilize the 'internal' transposon by selecting for individuals lacking the additional marker gene as demonstrated in embodiment 1.

In the following section we provide data that prove this principle:

Step1: Targeted DNA Cassette Exchange (RMCE. Step 1 in FIG. 5 and FIG. 7)

The final donor plasmid, pSL-FRT-EYFP-pBacR2-3×P3-DsRed-linotte-FRT3 (FIG. 10, in the following referred to as "final RMCE donor") contains, in-between the FRT and FRT3 sites, a cassette with: (i) a promotor-free eyfp ORF, (ii) the piggyBacR2 (3' end) transposon sequence, (iii) the transformation marker 3×P3-DsRed, and (iv) the homing sequence from the Drosophila linotte locus (see Taillebourg, E. & Dura, J. M. (1999). A novel mechanism for P element homing in Drosophila. Proc. Natl. Acad. Sci. USA 96, 6856-6861, the contents of which are incorporated herein by reference). Derivatives of the final RMCE donor vector carrying additional DNA sequences (genes-of-interest) can be constructed by insertion into the unique AscI and FseI cloning sites which are located upstream of the piggyBacR2 transposon sequence (FIG. 10).

Microinjection of the final RMCE donor was carried out using the Drosophila acceptor line M4.II ECFP (Table 2). This line carries the acceptor transgene pBac{3×P3-FRT-ECFP-linotte-FRT3} in the homozygous state. Embryos were injected under the conditions described previously. Single G0 founder males were crossed out and progeny (generation F1) were screened for the presence of both EYFP fluorescence and DsRed fluorescence (see FIG. 7). Targeting (i.e. individuals with ECFP to EYFP exchange) were observed at a frequency of 22.2%.

| | |
|---|---|
| Embryos injected: | 750 |
| single G0 male founders: | 178 |
| Fertile G0 male founders: | 158 |
| Setups producing EYFP and DsRed fluorescing F1 progeny: | 34 |

In total, 91 female and 62 male individuals were obtained which consistently showed an EYFP and DsRed eye fluorescence phenotype. Moreover, in these individuals ECFP fluorescence was absent as expected for recombination events. Though the exact mechanism (single versus double recombination) was not investigated for individuals from this targeting experiment, the previous pilot experiments suggest a significant fraction of double recombination events resulting from cassette exchange via FRT and FRT3 sites.

The results confirm a high efficiency of the gene targeting system disclosed in this embodiment, which is comparable to 'conventional' transposon-mediated germ-line transformation, at least for the vinegar fly Drosophila. In particular, the efficiency did not decrease significantly due to the interruption of the linotte sequence in the final donor plasmid or the increased size (2.6 kb compared to previous "pilot" donor vector) of the final donor plasmid (FIG. 10). This suggests that recombinants can also be generated with derivatives of the final donor plasmid carrying additional gene(s)-of-interest.

Step 2: piggyBac Transposase Induced Transposon Deletion of a Targeted Vector (Step 2 in FIG. 5 and FIG. 7)

Successful re-mobilization of the reconstituted piggyBac transposon is indicated by loss of DsRed fluorescence. Progeny lacking the sequence between piggyBacR2 and piggyBacL1 exclusively express EYFP fluorescence (see FIG. 7).

To examine whether the reconstituted internal piggyBac transposon vector can be re-mobilized by piggyBac transposase activity, individuals of generation F1 with EYFP and DsRed eye fluorescence were crossed to the following piggyBac-expressing jumpstarter lines:

(1) line Her{3×P3-ECFP; αtub-piggyBac} M6.II, referred to as "HerM6"
(2) line Her{3×P3-ECFP; αtub-piggyBac} M10.III, referred to as "HerM10"
(3) line Mi{3×P3-DsRed; hsp70-piggyBac} M5.II, referred to as "MiM5"

Progeny (generation F2) carrying both the final RMCE donor and the jumpstarter transgenes were crossed individually to non-transgenic Drosophila and progeny from these crosses (generation F3) were analyzed for the presence of individuals carrying EYFP but lacking DsRed eye fluorescence (Table 4).

TABLE 4

Phenotypic analysis for piggyBac transposon remobilization events. Progeny from single crosses of males carrying both final RMCE donor and jumpstarter transgenes (Js) to non-transgenic Drosophila virgin females were analyzed for individuals showing EYFP eye fluorescence but lacking DsRed eye fluorescence. Such a phenotype is consistent with a deletion of the internally reconstituted piggyBac transposon (FIG. 7).

| Js | HerM6 | | HerM10 | | MiM5 | |
|---|---|---|---|---|---|---|
| Setup | EYFP+ | DsRed− | EYFP+ | DsRed− | EYFP+ | DsRed− |
| 1 | 73 | 0 | 62 | 0 | 38 | 32 |
| 2 | 67 | 0 | 57 | 1 | 42 | 0 |
| 3 | 47 | 0 | 48 | 0 | 56 | 1 |
| 4 | 53 | 0 | 52 | 0 | 68 | 3 |
| 5 | 36 | 0 | 34 | 0 | 48 | 5 |
| 6 | 61 | 1 | 48 | 1 | 37 | 0 |
| 7 | 50 | 1 | 55 | 0 | 38 | 1 |
| 8 | 40 | 0 | 52 | 0 | 71 | 5 |
| 9 | 39 | 0 | 55 | 0 | 41 | 0 |
| 10 | 86 | 0 | 43 | 0 | 72 | 2 |
| 11 | 53 | 0 | 40 | 0 | 49 | 0 |
| 12 | 57 | 0 | 71 | 0 | 30 | 0 |
| 13 | 17 | 0 | 52 | 0 | 46 | 0 |
| 14 | 58 | 1 | 66 | 0 | 48 | 1 |
| 15 | 65 | 2 | 56 | 0 | 41 | 0 |
| 16 | 54 | 2 | 55 | 0 | 54 | 0 |
| 17 | 55 | 2 | 51 | 0 | 53 | 0 |
| 18 | 54 | 0 | 43 | 1 | 66 | 2 |
| 19 | 63 | 1 | 18 | 0 | 56 | 1 |
| 20 | 78 | 0 | 38 | 1 | 63 | 1 |
| Sum: | 1106 | 10 | 996 | 4 | 1017 | 25 |

Depending on the jumpstarter line employed, the frequency of remobilization ranged from 0.4% (HerM10) to 2.5% (MiM5). This indicates that the reconstituted internal piggyBac transposon vector can be remobilized efficiently, and the combination of different fluorescence markers allows the straightforward identification of remobilization events. Finally, the physical deletion of the reconstituted piggyBac transposon could be verified at a molecular level by PCR analysis (FIG. 9): Utilizing a primer pair binding to genomic region flanking to the RMCE acceptor transgenic line M4.II (primer M4.II Rev) and to piggyBacL1 sequences (primer pBL-R), the deletion of piggyBacL1 could be confirmed (compare PCR amplification products for acceptor line M4.II and immobilized lines #7 and #8 in FIG. 9). Moreover, utilizing a primer pair binding to genomic region flanking to the RMCE acceptor transgenic line M4.II (primer M4.II Rev) and to the linotte sequence (primer lioFwd) the truncation of the immobilized transgene could be confirmed (FIG. 9). The piggyBac remobilization event can be further confirmed by DNA sequencing over the genomic DNA to transgene DNA junction.

In conclusion, our data provide a proof-of-principle for the strategy of transgene immobilization by "RMCE with subsequent transposon deletion" in an invertebrate organism (Drosophila melanogaster).

Advantages of the Invention Over the Prior Art

The major advantage of the novel transformation systems disclosed in this patent application is the possibility to physically delete transposon DNA following the germ-line transformation process, in addition to targeting transgene integrations into predefined target sites. In this way, transposase-mediated mobilization or cross-mobilization of the genes-of-interest are excluded mechanistically and random genomic integrations are eliminated. In contrast to conventional germ-line transformation technology, our systems provide enhanced stability to the transgene insertion. Furthermore, DNA sequences required for the modification (e.g. transformation marker genes, transposase or recombinase target sites) are, to a large extent, removed from the genome after the final experimental step (step 2 in FIG. 1, step 3 in FIG. 4 and step 2 in FIG. 5). The final transgene insertion does not contain DNA sequences encoding complete target sites for the recombinases or transposases employed during the process, thereby eliminating the possibility for instability generated by these processes.

The RMCE technology, which is disclosed in this patent application for invertebrate organisms (exemplified in Drosophila melanogaster) represents an extremely versatile tool with application potential far beyond the goal of transgene immobilization. RMCE makes possible the targeted integration of DNA cassettes into a specific genomic DNA locus. This locus is pre-defined by the integration of the RMCE acceptor plasmid and can be characterized prior to a targeting experiment. In addition to the expected expression properties of the transgenes (including strength of expression, stage-specificity, tissue-specificity, and sex-specificity), the genomic environment of the transgene integration can have a significant effect on the level and tissue-specificity of expression. Therefore, suitable loci for integrations can be pre-selected before performing a gene targeting experiment according to the requirements specific for the experimental setup, and in addition, host strains with optimal fitness may be selected. Moreover, multiple cassette exchange reactions can be performed in a repetitive way, i.e. an acceptor cassette in a particular invertebrate strain with a specific genetic makeup can be repetitively exchanged by multiple donor cassettes. Furthermore, several different transgenes can be placed exactly at the same genomic locus. This allows for the first time the ability to eliminate genomic positional effects and to comparatively study the biological effects of different transgenes.

The particular embodiments of the invention are highly flexible. The functionality of systems disclosed is neither dependent on the particular transposable elements used in the embodiments, nor on the particular transformation marker genes used in the embodiments, nor on the particular site-specific recombination system used in the embodiments, nor on the particular homing sequence used in embodiment 3. Finally, all embodiments have broad general application potential in vertebrate and invertebrate organisms that are subject to transposon-mediated transformation or recombinase-mediated recombination, and fluorescent protein marking systems.

What is claimed is:

1. A method for targeting a heritable integration of a transgene within a genome of a somatic or germ line cell of an invertebrate organism, said method comprising:

integrating into said genome a first DNA cassette carrying a first transposon half side at one end, a second transposon half side in opposite orientation at the other end, a first wild-type, non-mutated recombinase target site, and a second, mutated recombinase target site that is heterospecific to the first recombinase target site, wherein the recombinase target sites are flanked by said transposon half sides, catalyzing an exchange between said first DNA cassette for a second DNA cassette by introducing into the cell comprising said genome a site-specific recombinase that catalyzes a DNA recombination reaction between homospecific recombinase target sites and said second DNA cassette, said second DNA cassette comprising the same first, wild-type, non-mutated and second, mutated recombinase target sites in the same orientation as those of the first DNA cassette, an internal transposon half side flanked by said recombinase target sites, said internal half side being in the same orientation as the second transposon half side of the first DNA cassette, and the transgene positioned between said internal half side and the second, mutated recombinase site, to result in integration of the transgene into the genome; and identifying that said transgene has been integrated into said genome.

2. The method of claim 1, wherein said site-specific recombinase is FLP recombinase, and wherein said recombinase target sites are FRT sites or mutated derivatives of said FRT sites.

3. The method of claim 1, wherein said site-specific recombinase is Cre recombinase, and wherein said recombinase target sites are loxP sites or mutated derivatives of said loxP sites.

4. The method of claim 1, wherein said first DNA cassette further comprises a marker gene coding region operably linked to a promoter DNA, said marker gene coding region being positioned between the recombinase target sites.

5. The method of claim 1, wherein said first cassette further comprises a homing sequence to enhance pairing with said homospecific recombinase target sites in said second cassette.

6. The method of claim 5, wherein said homing sequence comprises a *Drosophila* linotte homing sequence.

7. The method of claim 1 further comprising the step of excising the transposon positioned by the first transposon half side and said internal half side with a transposase following the exchange of the first DNA cassette with said second DNA cassette, wherein the transgene is immobilized into said genome.

8. The method of claim 4, wherein said second cassette further comprises a second marker gene coding region lacking a promoter, and wherein, following the exchange between said first DNA cassette and said second DNA cassette, said second marker gene is placed under the control of the promoter of the first cassette.

9. The method of claim 5, wherein said second cassette comprises the same homing sequence as said first cassette within said recombinase target sites.

10. The method of claim 1, wherein said second cassette further comprises a pair of phenotypically distinguishable marker genes flanking said internal half side and positioned between said first and second recombinase target sites.

11. The method of claim 10, wherein one of said marker genes lacks a promoter.

12. An invertebrate organism comprising the heritable transgene produced according to claim 1.

* * * * *

```
                        SEQUENCE LISTING

<160> NUMBER OF SEQ ID NOS: 24

<210> SEQ ID NO 1
<211> LENGTH: 9096
<212> TYPE: DNA
<213> ORGANISM: Artificial Sequence
<220> FEATURE:
<223> OTHER INFORMATION: Description of Artificial Sequence: Synthetic
      vector sequence

<400> SEQUENCE: 1
ctaaattgta agcgttaata ttttgttaaa attcgcgtta aattttttgtt aaatcagctc      60 atttttttaac caataggccg aaatcggcaa aatcccttat aaatcaaaag aatagaccga    120
gatagggttg agtgttgttc cagtttggaa caagagtcca ctattaaaga acgtggactc    180
caacgtcaaa gggcgaaaaa ccgtctatca gggcgatggc ccactacgtg aaccatcacc    240
ctaatcaagt tttttggggt cgaggtgccg taaagcacta aatcggaacc ctaaagggag    300
cccccgattt agagcttgac ggggaaagcc ggcgaacgtg gcgagaaagg aagggaagaa    360
agcgaaagga gcgggcgcta gggcgctggc aagtgtagcg gtcacgctgc gcgtaaccac    420
cacacccgcc gcgcttaatg cgccgctaca gggcgcgtcc cattcgccat tcaggctgcg    480
caactgttgg gaagggcgat cggtgcgggc ctcttcgcta ttacgccagc tggcgaaagg    540
gggatgtgct gcaaggcgat taagttgggt aacgccaggg ttttcccagt cacgacgttg    600
taaaacgacg gccagtgagc gcgcctcgtt cattcacgtt tttgaacccg tggaggacgg    660
gcagactcgc ggtgcaaatg tgttttacag cgtgatggag cagatgaaga tgctcgacac    720
gctgcagaac acgcagctag attaaccctg aaagataat catattgtga cgtacgttaa    780
agataatcat gcgtaaaatt gacgcatgtg ttttatcggt ctgtatatcg aggtttattt    840
attaatttga atagatatta agttttatta tatttacact tacatactaa taataaattc    900
aacaaacaat ttatttatgt ttatttattt attaaaaaaa aacaaaaact caaaatttct    960
tctataaagt aacaaaactt ttatcgaatt cctgcagccc gggggatcca ctagttctag   1020
tgttcccaca atggttaatt cgagctcgcc cggggatcta attcaattag agactaattc   1080
aattagagct aattcaatta ggatccaagc ttatcgattt cgaaccctcg accgccggag   1140
tataaataga ggcgcttcgt ctacggagcg acaattcaat tcaaacaagc aaagtgaaca   1200
cgtcgctaag cgaaagctaa gcaaataaac aagcgcagct gaacaagcta acaatcggg    1260 gtaccgctag agtcgacggt acgatccacc ggtcgccacc atggtgagca agggcgagga   1320
gctgttcacc ggggtggtgc ccatcctggt cgagctggac ggcgacgtaa acggccacaa   1380
gttcagcgtg tccggcgagg gcgagggcga tgccacctac ggcaagctga ccctgaagtt   1440
catctgcacc accggcaagc tgcccgtgcc ctggcccacc ctcgtgacca ccctgacctg   1500
gggcgtgcag tgcttcagcc gctacccccga ccacatgaag cagcacgact tcttcaagtc   1560
cgccatgccc gaaggctacg tccaggagcg caccatcttc ttcaaggacg acggcaacta   1620
caagacccgc gccgaggtga agttcgaggg cgacaccctg gtgaaccgca tcgagctgaa   1680
gggcatcgac ttcaaggagg acggcaacat cctggggcac aagctggagt acaactacat   1740
cagccacaac gtctatatca ccgccgacaa gcagaagaac ggcatcaagg ccaacttcaa   1800
```

```
gatccgccac aacatcgagg acggcagcgt gcagctcgcc gaccactacc agcagaacac   1860
ccccatcggc gacggccccg tgctgctgcc cgacaaccac tacctgagca cccagtccgc   1920
cctgagcaaa gaccccaacg agaagcgcga tcacatggtc ctgctggagt tcgtgaccgc   1980
cgccgggatc actctcggca tggacgagct gtacaagtaa agcggccgcg actctagatc   2040
ataatcagcc ataccacatt tgtagaggtt ttacttgctt taaaaaacct cccacacctc   2100
cccctgaacc tgaaacataa aatgaatgca attgttgttg ttaacttgtt tattgcagct   2160
tataatggtt acaaataaag caatagcatc acaaatttca caaataaagc attttttca   2220 ctgcattcta gttgtggttt gtccaaactc atcaatgtat cttaaagctt atcgatacgc   2280
gtacggcgcg cctaggccgg ccgatactag agcggccgcc accgcggtgg agctccagct   2340
tttgttccct ttagtgaggg ttaattagat cttaatacga ctcactatag ggcgaattgg   2400
gtaccgggcc cccctcgag gtcgacggta tcgataagct tgatatctat aacaagaaaa   2460
tatatatata ataagttatc acgtaagtag aacatgaaat aacaatataa ttatcgtatg   2520
agttaaatct aaaagtcac gtaaaagata atcatgcgtc attttgactc acgcggtcgt   2580
tatagttcaa aatcagtgac acttaccgca ttgacaagca cgcctcacgg gagctccaag   2640
cggcgactga gatgtcctaa atgcacagcg acggattcgc gctatttaga aagagagagc   2700
aatatttcaa gaatgcatgc gtcaatttta cgcagactat ctttctaggg ttaatctagc   2760
tgcatcagga tcatatcgtc gggtcttttt tccggctcag tcatcgccca agctggcgct   2820
atctgggcat cggggaggaa gaagcccgtg ccttttcccg cgaggttgaa gcggcatgga   2880
aagagtttgc cgaggatgac tgctgctgca ttgacgttga gcgaaaacgc acgtttacca   2940
tgatgattcg ggaaggtgtg ggatacattg atgagtttgg acaaaccaca actagaatgc   3000
agtgaaaaaa atgctttatt tgtgaaattt gtgatgctat tgctttattt gtaaccatta   3060
taagctgcaa taaacaagtt aacaacaaca attgcattca ttttatgttt caggttcagg   3120
gggaggtgtg ggaggttttt taaagcaagt aaaacctcta caaatgtggt atggctgatt   3180
atgatctaga gtcgcggccg ctacaggaac aggtggtggc ggccctcggt gcgctcgtac   3240
tgctccacga tggtgtagtc ctcgttgtgg gaggtgatgt ccagcttgga gtccacgtag   3300
tagtagccgg gcagctgcac gggcttcttg gccatgtaga tggacttgaa ctccaccagg   3360
tagtggccgc cgtccttcag cttcagggcc ttgtggatct cgcccttcag cacgccgtcg   3420
cgggggtaca ggcgctcggt ggaggcctcc cagcccatgg tcttcttctg cattacgggg   3480
ccgtcggagg ggaagttcac gccgatgaac ttcaccttgt agatgaagca gccgtcctgc   3540
agggaggagt cttgggtcac ggtcaccacg ccgccgtcct cgaagttcat cacgcgctcc   3600
cacttgaagc cctcggggaa ggacagcttc ttgtagtcgg ggatgtcggc ggggtgcttc   3660
acgtacacct tggagccgta ctggaactgg ggggacagga tgtcccaggc gaagggcagg   3720
gggccgccct tggtcacctt cagcttcacg gtgttgtggc cctcgtaggg gcggccctcg   3780
ccctcgccct cgatctcgaa ctcgtggccg ttcacggtgc cctccatgcg cacccttgaag   3840 cgcatgaact ccttgatgac gttcttggag gagcgcacca tggtggcgac cggtggatcc   3900
ccgatctgca ttttggatta ttctgcgggt caaatagag atgtgaaaa ttagtacgaa   3960 atcaaatgag tttcgttgaa attacaaaac tattgaaact aacttcctgg ctggggaata   4020
aaaatgggaa acttatttat cgacgccaac tttgttgaga acccctatt aaccctctac   4080 gaatattgga acaaaggaaa gcgaagaaac aggaacaaag gtagttgaga aacctgttcc   4140
```

-continued

```
gttgctcgtc atcgttttca taatgcgagt gtgtgcatgt atatatacac agctgaaacg    4200
catgcataca cattattttg tgtgtatatg gtgacgtcac aactactaag caataagaaa    4260
ttttccagac gtggctttcg tttcaagcaa cctactctat ttcagctaaa ataagtgga     4320
tttcgttggt aaaatacttc aattaagcaa agaactaact aactaataac atgcacacaa    4380
atgctcgagt gcgttcgtga tttctcgaat tttcaaatgc gtcactgcga atttcacaat    4440
ttgccaataa atcttggcga aaatcaacac gcaagtttta tttatagatt tgtttgcgtt    4500
ttgatgccaa ttgattggga aaacaagatg cgtggctgcc aatttcttat tttgtaatta    4560
cgtagagcgt tgaataaaaa aaaaatggcc gaacaaagac cttgaaatgc agtttttctt    4620
gaaattactc aacgtcttgt tgctcttatt actaattggt aacagcgagt taaaaactta    4680
cgtttcttgt gactttcgag aatgttcttt taattgtact ttaatcacca acaattaagt    4740
ataaatttt cgctgattgc gctttacttt ctgcttgtac ttgctgctgc aaatgtcaat     4800
tggttttgaa ggcgaccgtt cgcgaacgct gtttatatac cttcggtgtc cgttgaaaat    4860
cactaaaaaa taccgtagtg ttcgtaacac tttagtacag agaaaaaaaa ttgtgccgaa    4920
atgttttga tacgtacgaa taccttgtat taaaattttt tatgatttct gtgtatcact     4980
ttttttttgt gttttcgtt taaactcacc acagtacaaa acaataaaat attttaaga     5040
caatttcaaa ttgagaccctt tctcgtactg acttgaccgg ctgaatgagg atttctacct   5100
agacgaccta cttcttacca tgacattgaa tgcaatgcca cctttgatct aaacttacaa    5160
aagtccaagg cttgttagga ttggtgttta tttagtttgc ttttgaaata gcactgtctt    5220
ctctaccggc tataattttg aaactcgcag cttgactgga aatttaaaaa gtaattctgt    5280
gtaggtaaag ggtgttttaa aagtgtgatg tgttgagcgt tgcggcaacg actgctattt    5340
atgtatatat tttcaaaact tattgttttt gaagtgtttt aaatggagct atctggcaac    5400
gctgcgcata atcttacaca agcttttctt aatccatttt taagtgaaat ttgttttac     5460
tctttcggca ataattgtt aaatcgcttt aagtgggctt acatctggat aagtaatgaa     5520
aacctgcata ttataatatt aaaacatata atccactgtg ctttccccgt gtgtggccat    5580
atacctaaaa aagtttattt tcgcagagcc ccgcacggtc acactacggt tcggcgattt    5640
tcgattttgg acagtactga ttgcaagcgc accgaaagca aaatggagct ggagattttg    5700
aacgcgaaga acagcaagcc gtacggcaag gtgaaggtgc cctccggcgc cacgcccatc    5760
ggcgatctgc gcgccctaat tcacaagacc ctgaagcaga ccccacacgc gaatcgccag    5820
tcgcttcgtc tggaactgaa gggcaaaagc ctgaaagata cggacacatt ggaatctctg    5880
tcgctgcgtt ccggcgacaa gatcgggtac cgtcgactgc agaattcgaa gcttgagctc    5940
gagatctgac aatgttcagt gcagagactc ggctacgcct cgtggacttt gaagttgacc    6000
aacaatgttt attcttacct ctaatagtcc tctgtggcaa ggtcaagatt ctgttagaag    6060
ccaatgaaga acctggttgt tcaataacat tttgttcgtc taatatttca ctaccgcttg    6120
acgttggctg cacttcatgt acctcatcta taaacgcttc ttctgtatcg ctctggacgt    6180
catcttcact tacgtgatct gatatttcac tgtcagaatc ctcaccaaca agctcgtcat    6240
cgctttgcag aagagcagag aggatatgct catcgtctaa agaactaccc atttattat    6300
atattagtca cgatatctat aacaagaaaa tatatatata ataagttatc acgtaagtag   6360
aacatgaaat aacaatataa ttatcgtatg agttaaatct taaaagtcac gtaaaagata   6420
atcatgcgtc attttgactc acgcggtcgt tatagttcaa aatcagtgac acttaccgca    6480
ttgacaagca cgcctcacgg gagctccaag cggcgactga gatgtcctaa atgcacagcg    6540
```

```
acggattcgc gctatttaga aagagagagc aatatttcaa gaatgcatgc gtcaatttta   6600
cgcagactat ctttctaggg ttaaaaaaga tttgcgcttt actcgaccta aactttaaac   6660
acgttaacca tgcacgcctt taacggtgaa ctgttcgttc aggccacctg ggataccagt   6720
tcgtcgcggc ttttccggac acagttccgg atggtcagcc cgaagcgcat cagcaacccg   6780
aacaataccg cgcacagccg gaactgccgt gccggtgtgc agattaatga cagcggtgcg   6840
gcgctgggat attacgtcag cgaggacggg tatcctggct ggatgccgca gaaatggaca   6900
tggataccccc gtgagttacc cggcgggcgc gcttggcgta atcatggtca tagctgtttc   6960
ctgtgtgaaa ttgttatccg ctcacaattc cacacaacat acgagccgga agcataaagt   7020
gtaaagcctg gggtgcctaa tgagtgagct aactcacatt aattgcgttg cgctcactgc   7080
ccgctttcca gtcgggaaac ctgtcgtgcc agctgcatta atgaatcggc caacgcgcgg   7140
ggagaggcgg tttgcgtatt gggcgctctt ccgcttcctc gctcactgac tcgctgcgct   7200
cggtcgttcg gctgcggcga gcggtatcag ctcactcaaa ggcggtaata cggttatcca   7260
cagaatcagg ggataacgca ggaaagaaca tgtgagcaaa aggccagcaa aaggccagga   7320
accgtaaaaa ggccgcgttg ctggcgtttt tccataggct ccgcccccct gacgagcatc   7380
acaaaaatcg acgctcaagt cagaggtggc gaaacccgac aggactataa agataccagg   7440
cgtttccccc tggaagctcc ctcgtgcgct ctcctgttcc gaccctgccg cttaccggat   7500
acctgtccgc ctttctccct tcgggaagcg tggcgctttc tcatagctca cgctgtaggt   7560
atctcagttc ggtgtaggtc gttcgctcca agctgggctg tgtgcacgaa ccccccgttc   7620
agcccgaccg ctgcgcctta tccggtaact atcgtcttga gtccaacccg gtaagacacg   7680
acttatcgcc actggcagca gccactggta acaggattag cagagcgagg tatgtaggcg   7740
gtgctacaga gttcttgaag tggtggccta actacggcta cactagaagg acagtatttg   7800
gtatctgcgc tctgctgaag ccagttacct tcggaaaaag agttggtagc tcttgatccg   7860
gcaaacaaac caccgctggt agcggtggtt tttttgtttg caagcagcag attacgcgca   7920
gaaaaaaagg atctcaagaa gatcctttga tcttttctac ggggtctgac gctcagtgga   7980
acgaaaactc acgttaaggg attttggtca tgagattatc aaaaaggatc ttcacctaga   8040
tccttttaaa ttaaaaatga agttttaaat caatctaaag tatatatgag taaacttggt   8100
ctgacagtta ccaatgctta atcagtgagg cacctatctc agcgatctgt ctatttcgtt   8160
catccatagt tgcctgactc cccgtcgtgt agataactac gatacgggag ggcttaccat   8220
ctggccccag tgctgcaatg ataccgcgag acccacgctc accggctcca gatttatcag   8280
caataaacca gccagccgga agggccgagc gcagaagtgg tcctgcaact ttatccgcct   8340
ccatccagtc tattaattgt tgccgggaag ctagagtaag tagttcgcca gttaatagtt   8400
tgcgcaacgt tgttgccatt gctacaggca tcgtggtgtc acgctcgtcg tttggtatgg   8460
cttcattcag ctccggttcc caacgatcaa ggcgagttac atgatccccc atgttgtgca   8520
aaaaagcggt tagctccttc ggtcctccga tcgttgtcag aagtaagttg gccgcagtgt   8580
tatcactcat ggttatggca gcactgcata attctcttac tgtcatgcca tccgtaagat   8640
gcttttctgt gactggtgag tactcaacca agtcattctg agaatagtgt atgcggcgac   8700
cgagttgctc ttgcccggcg tcaatacggg ataataccgc gccacatagc agaactttaa   8760
aagtgctcat cattggaaaa cgttcttcgg ggcgaaaact ctcaaggatc ttaccgctgt   8820
tgagatccag ttcgatgtaa cccactcgtg cacccaactg atcttcagca tcttttactt   8880
```

```
tcaccagcgt ttctgggtga gcaaaaacag gaaggcaaaa tgccgcaaaa aagggaataa      8940
gggcgacacg gaaatgttga atactcatac tcttcctttt tcaatattat tgaagcattt      9000
atcagggtta ttgtctcatg agcggataca tatttgaatg tatttagaaa aataaacaaa      9060
taggggttcc gcgcacattt ccccgaaaag tgccac                                9096

<210> SEQ ID NO 2
<211> LENGTH: 8244
<212> TYPE: DNA
<213> ORGANISM: Artificial Sequence
<220> FEATURE:
<223> OTHER INFORMATION: Description of Artificial Sequence: Synthetic
      vector sequence

<400> SEQUENCE: 2
gagctcgccc ggggatctaa ttcaattaga gactaattca attagagcta attcaattag        60
gatccaagct tatcgatttc gaaccctcga ccgccggagt ataaatagag gcgcttcgtc       120
tacggagcga caattcaatt caaacaagca aagtgaacac gtcgctaagc gaaagctaag       180
caaataaaca gcgcagctg aacaagctaa acaatcgggg tacccgggga tcttgaagtt       240
cctattccga agttcctatt ctctagaaag tataggaact tcagagcgct tttgaagcta       300
ggcggcccta gagtcgacgg tacgatccac cggtcgccac catggtgagc aagggcgagg       360
agctgttcac cggggtggtg cccatcctgg tcgagctgga cggcgacgta aacggccaca       420
agttcagcgt gtccggcgag ggcgagggcg atgccaccta cggcaagctg accctgaagt       480
tcatctgcac caccggcaag ctgcccgtgc cctggcccac cctcgtgacc accctgacct       540
ggggcgtgca gtgcttcagc cgctaccccg accacatgaa gcagcacgac ttcttcaagt       600
ccgccatgcc cgaaggctac gtccaggagc gcaccatctt cttcaaggac gacggcaact       660
acaagacccg cgccgaggtg aagttcgagg gcgacaccct ggtgaaccgc atcgagctga       720
agggcatcga cttcaaggag gacggcaaca tcctggggca caagctggag tacaactaca       780
tcagccacaa cgtctatatc accgccgaca agcagaagaa cggcatcaag gccaacttca       840
agatccgcca caacatcgag gacggcagcg tgcagctcgc cgaccactac cagcagaaca       900
cccccatcgg cgacggcccc gtgctgctgc ccgacaacca ctacctgagc acccagtccg       960
ccctgagcaa agaccccaac gagaagcgcg atcacatggt cctgctggag ttcgtgaccg      1020
ccgccgggat cactctcggc atggacgagc tgtacaagta aagcggccgc gactctagat      1080
cataatcagc cataccacat ttgtagaggt tttacttgct ttaaaaaacc tcccacacct      1140
ccccctgaac ctgaaacata aaatgaatgc aattgttgtt gttaacttgt ttattgcagc      1200
ttataatggt tacaaataaa gcaatagcat cacaaatttc acaaataaag catttttttc      1260
actgcattct agttgtggtt tgtccaaact catcaatgta tcttaaagct tatcgatacg      1320
cgtacggcgc gccaaaagct tctgtctctc tttctgtaat aaactaacga tttataaagt      1380
ataaaatgtc gtaatgttta ttttggcaa catgagttta attcgaaatt gaatcaaaca      1440
caataaaaaa aagttaaaag gttaaaatca ttatattaca tcattaattc gaattcattt      1500
gggaagtttg tgggtctatt ttttaaactt tatatgaatg tttgtttagt taatttaata      1560
aaggatatcg aacagtatgc cagttttggt atttagccaa ttggagatgt tcgatgagat      1620
gttcgaactg caaccgagtt cgaggttcca acacgactgt tatacgggtt ccagccttca      1680
agttctacag aacaagtcca cgagcgccac acacagtcca cagtccacac tccactccgc      1740
tcggcgtgga agccattcgc ttcgtggcga agtgtttgtt tatccagttg acagtttgtg      1800
```

```
gaaaatcgtc acggtgagcg gatcaaacgc ggaaaacgaa cgcggacgaa cggcgagaaa      1860
agcgaggaaa aacgggtgca gagacagaga ctgattggga aatatgtgcg cctgagtttt      1920
cccggccaga aggcaaagtg ccaaatgctc tgacaaataa ttcctgtaat aatcagcgcg      1980
attgaaatca acgcgacgct cgtaaaattg caaatgcagc gcaaaagtg aacagcagtg       2040 cagcggaaat taaatcgttt tagcgagtgc caaacgggaa atagaaaatc ggcagagtag      2100
ccgaactgca gttaaaacta tctcttcctc ttattgcgac taaacaaccg gcggattaat      2160
cgaatccgaa agatggcccc caacttgcta acaatcggat tacttttgac cctgatcgcc      2220
agcggtcagg cccatctcaa tattttcctc aacttgcacg aggtgctgcg cctaatcggt      2280
aagtaatcgt gttgattttc gcctgccttt tggcttttca attaactggg caattatttg      2340
ccactttgtg tgcgttcgtt cgactttaaa tcaaatttga tttatgccaa gccgggattt      2400
tgtctcctgg gcaaacgaat gcgacttgct gggattattt actcttttg cgtaaataat        2460 atatgccttt taattgtttc tagcctcgga gctacatata aagtagtatt gtccctcctt      2520
caattggcca gctcaccgag aaacaagaaa acattctatt tgtctagcat gatttcctgt      2580
ttctttgatt taattgttcg ttagacttat ctagataaat agaaatgcta aagcgattta      2640
aatttgtatt tctttgcgtt aaattaaatt cgattggcaa gtggattcat ctctagataa      2700
gtaatccctc tataatcaaa gttttattt aaaaatcat attttttcat agtttatcca        2760
atttaaaaca atacaaaaca attttagata tattttataa acgtcttcaa aagaaaataa      2820
atagtaaaat catgtagtca aaaaatgaca ccaaaatgag tatttaaata tttagtttag      2880
tttagtttat attatttatt tagcctaact attttccata gaagaatact actctaataa     2940
gcttggggta cccggggatc ttgaagttcc tattccgaag ttcctattct tcaaatagta     3000
taggaacttc agatctgaca atgttcagtg cagagactcg gctacgcctc gtggactttg     3060
aagttgacca acaatgttta ttcttacctc taatagtcct ctgtggcaag gtcaagattc     3120
tgttagaagc caatgaagaa cctggttgtt caataacatt ttgttcgtct aatatttcac     3180
taccgcttga cgttggctgc acttcatgta cctcatctat aaacgcttct tctgtatcgc     3240
tctggacgtc atcttcactt acgtgatctg atatttcact gtcagaatcc tcaccaacaa     3300
gctcgtcatc gctttgcaga agagcagaga ggatatgctc atcgtctaaa gaactaccca     3360
ttttattata tattagtcac gatatctata acaagaaaat atatatataa taagttatca     3420
cgtaagtaga acatgaaata acaatataat tatcgtatga gttaaatctt aaaagtcacg     3480
taaaagataa tcatgcgtca ttttgactca cgcggtcgtt atagttcaaa atcagtgaca     3540
cttaccgcat tgacaagcac gcctcacggg agctccaagc ggcgactgag atgtcctaaa     3600
tgcacagcga cggattcgcg ctatttagaa agagagagca atatttcaag aatgcatgcg     3660
tcaattttac gcagactatc tttctagggt taaaaagat ttgcgcttta ctcgacctaa       3720
actttaaaca cgtcatagaa tcttcgtttg acaaaaacca cattgtggcc aagctgtgtg     3780
acgcgacgcg cgctaaagaa tggcaaacca agtcgcgcga gcgtcgactc tagaggatcc     3840
ccgggtaccg agctcgaatt cgtaatcatg gtcatagctg tttcctgtgt gaaattgtta     3900
tccgctcaca attccacaca acatacgagc cggaagcata aagtgtaaag cctggggtgc     3960
ctaatgagtg agctaactca cattaattgc gttgcgctca ctgcccgctt tccagtcggg     4020
aaacctgtcg tgccagctgc attaatgaat cggccaacgc gcgggagag gcggtttgcg     4080 tattgggcgc tcttccgctt cctcgctcac tgactcgctg cgctcggtcg ttcggctgcg     4140
gcgagcggta tcagctcact caaaggcggt aatacggtta ccacagaat cagggggataa     4200
```

```
cgcaggaaag aacatgtgag caaaaggcca gcaaaaggcc aggaaccgta aaaaggccgc    4260
gttgctggcg ttttttccata ggctccgccc ccctgacgag catcacaaaa atcgacgctc    4320
aagtcagagg tggcgaaacc cgacaggact ataaagatac caggcgtttc ccctggaag     4380 ctccctcgtg cgctctcctg ttccgaccct gccgcttacc ggatacctgt ccgcctttct    4440
cccttcggga agcgtggcgc tttctcaatg ctcacgctgt aggtatctca gttcggtgta    4500
ggtcgttcgc tccaagctgg gctgtgtgca cgaaccccc gttcagcccg accgctgcgc     4560
cttatccggt aactatcgtc ttgagtccaa cccggtaaga cacgacttat cgccactggc    4620
agcagccact ggtaacagga ttagcagagc gaggtatgta ggcggtgcta cagagttctt    4680
gaagtggtgg cctaactacg gctacactag aaggacagta tttggtatct gcgctctgct    4740
gaagccagtt accttcggaa aaagagttgg tagctcttga tccggcaaac aaaccaccgc    4800
tggtagcggt ggttttttg tttgcaagca gcagattacg cgcagaaaaa aaggatctca     4860
agaagatcct ttgatctttt ctacggggtc tgacgctcag tggaacgaaa actcacgtta    4920
agggattttg gtcatgagat tatcaaaaag gatcttcacc tagatccttt taaattaaaa    4980
atgaagtttt aaatcaatct aaagtatata tgagtaaact tggtctgaca gttaccaatg    5040
cttaatcagt gaggcaccta tctcagcgat ctgtctattt cgttcatcca tagttgcctg    5100
actccccgtc gtgtagataa ctacgatacg ggagggctta ccatctggcc ccagtgctgc    5160
aatgataccg cgagacccac gctcaccggc tccagattta tcagcaataa accagccagc    5220
cggaagggcc gagcgcagaa gtggtcctgc aactttatcc gcctccatcc agtctattaa    5280
ttgttgccgg gaagctagag taagtagttc gccagttaat agtttgcgca acgttgttgc    5340
cattgctaca ggcatcgtgg tgtcacgctc gtcgtttggt atggcttcat tcagctccgg    5400
ttcccaacga tcaaggcgag ttacatgatc ccccatgttg tgcaaaaaag cggttagctc    5460
cttcggtcct ccgatcgttg tcagaagtaa gttggccgca gtgttatcac tcatggttat    5520
ggcagcactg cataattctc ttactgtcat gccatccgta agatgctttt ctgtgactgg    5580
tgagtactca accaagtcat tctgagaata gtgtatgcgg cgaccgagtt gctcttgccc    5640
ggcgtcaata cgggataata ccgcgccaca tagcagaact ttaaaagtgc tcatcattgg    5700
aaaacgttct cggggcgaaa actctcaag gatcttaccg ctgttgagat ccagttcgat     5760
gtaacccact cgtgcaccca actgatcttc agcatctttt actttcacca gcgtttctgg    5820
gtgagcaaaa acaggaaggc aaaatgccgc aaaaaaggga ataagggcga cacggaaatg    5880
ttgaatactc atactcttcc ttttttcaata ttattgaagc atttatcagg gttattgtct    5940
catgagcgga tacatatttg aatgtattta gaaaaataaa caaatagggg ttccgcgcac    6000
atttccccga aaagtgccac ctgacgtcta agaaaccatt attatcatga cattaaccta    6060
taaaaatagg cgtatcacga ggccctttcg tctcgcgcgt ttcggtgatg acggtgaaaa    6120
cctctgacac atgcagctcc cggagacggt cacagcttgt ctgtaagcgg atgccgggag    6180
cagacaagcc cgtcagggcg cgtcagcggg tgttggcggg tgtcggggct ggcttaacta    6240
tgcggcatca gagcagattg tactgagagt gcaccatatg cggtgtgaaa taccgcacag    6300
atgcgtaagg agaaaatacc gcatcaggcg ccattcgcca ttcaggctgc gcaactgttg    6360
ggaagggcga tcggtgcggg cctcttcgct attacgccag ctggcgaaag gggatgtgc     6420 tgcaaggcga ttaagttggg taacgccagg gttttcccag tcacgacgtt gtaaaacgac    6480
ggccagtgcc aagctttgtt taaatataaa caaaattgtg atcccacaaa atgaagtggg    6540
```

| | |
|---|---:|
| gcaaaatcaa ataattaata gtgtccgtaa acttgttggt cttcaactttt ttgaggaaca | 6600 |
| cgttggacgg caaatccgtg actataacac aagttgattt aataatttta gccaacacgt | 6660 |
| cgggctgcgt gttttttgcc gacgcgtctg tgtacacgtt gattaactgg tcgattaaac | 6720 |
| tgttgaaata atttaatttt tggttcttct ttaaatctgt gatgaaattt tttaaaataa | 6780 |
| ctttaaattc ttcattggta aaaaatgcca cgttttgcaa cttgtgaggg tctaatatga | 6840 |
| ggtcaaactc agtaggagtt ttatccaaaa aagaaaacat gattacgtct gtacacgaac | 6900 |
| gcgtattaac gcagagtgca aagtataaga gggttaaaaa atatatttta cgcaccatat | 6960 |
| acgcatcggg ttgatatcgt taatatggat caatttgaac agttgattaa cgtgtctctg | 7020 |
| ctcaagtctt tgatcaaaac gcaaatcgac gaaatgtgt cggacaatat caagtcgatg | 7080 |
| agcgaaaaac taaaaaggct agaatacgac aatctcacag acagcgttga gatatacggt | 7140 |
| attcacgaca gcaggctgaa taataaaaaa attagaaact attatttaac cctagaaaga | 7200 |
| taatcatatt gtgacgtacg ttaaagataa tcatgcgtaa aattgacgca tgtgttttat | 7260 |
| cggtctgtat atcgaggttt atttattaat ttgaatagat attaagtttt attatattta | 7320 |
| cacttacata ctaataataa attcaacaaa caatttattt atgtttattt atttattaaa | 7380 |
| aaaaaacaaa aactcaaaat ttcttctata aagtaacaaa acttttaaac attctctctt | 7440 |
| ttacaaaaat aaacttattt tgtactttaa aaacagtcat gttgtattat aaaataagta | 7500 |
| attagcttaa cttatacata atagaaacaa attatactta ttagtcagtc agaaacaact | 7560 |
| ttggcacata tcaatattat gctctcgaca aataacttttt ttgcattttt tgcacgatgc | 7620 |
| atttgccttt cgccttattt tagaggggca gtaagtacag taagtacgtt ttttcattac | 7680 |
| tggctcttca gtactgtcat ctgatgtacc aggcacttca tttggcaaaa tattagagat | 7740 |
| attatcgcgc aaatatctct tcaaagtagg agcttctaaa cgcttacgca taaacgatga | 7800 |
| cgtcaggctc atgtaaaggt ttctcataaa ttttttgcga cttggacct tttctccctt | 7860 |
| gctactgaca ttatggctgt atataataaa agaatttatg caggcaatgt ttatcattcc | 7920 |
| gtacaataat gccataggcc acctattcgt cttcctactg caggtcatca cagaacacat | 7980 |
| ttggtctagc gtgtccactc cgcctttagt ttgattataa tacataacca tttgcggttt | 8040 |
| accggtactt tcgttgatag aagcatcctc atcacaagat gataaagt ataccatctt | 8100 |
| agctggcttc ggtttatatg agacgagagt aaggggtccg tcaaaacaaa acatcgatgt | 8160 |
| tcccactggc ctggagcgac tgttttcag tacttccggt atctcgcgtt tgtttgatcg | 8220 |
| cacggttccc acaatggtta attc | 8244 |

<210> SEQ ID NO 3
<211> LENGTH: 8638
<212> TYPE: DNA
<213> ORGANISM: Artificial Sequence
<220> FEATURE:
<223> OTHER INFORMATION: Description of Artificial Sequence: Synthetic
    vector sequence

<400> SEQUENCE: 3

| | |
|---|---:|
| cgtcgctaag cgaaagctaa gcaaataaac aagcgcagct gaacaagcta acaatcgggg | 60 |
| gtacccgggg atcttgaagt tcctattccg aagttcctat tctctagaaa gtataggaac | 120 |
| ttcagagcgc ttttgaagct aggcggccct agagtcgacg gtacgatcca ccggtcgcca | 180 |
| ccatggtgag caagggcgag gagctgttca ccggggtggt gcccatcctg gtcgagctgg | 240 |
| acggcgacgt aaacggccac aagttcagcg tgtccggcga gggcgagggc gatgccacct | 300 |

```
acggcaagct gaccctgaag ttcatctgca ccaccggcaa gctgcccgtg ccctggccca      360
ccctcgtgac caccttcggc tacggcctgc agtgcttcgc ccgctacccc gaccacatga      420
agcagcacga cttcttcaag tccgccatgc ccgaaggcta cgtccaggag cgcaccatct      480
tcttcaagga cgacggcaac tacaagaccc gcgccgaggt gaagttcgag ggcgacaccc      540
tggtgaaccg catcgagctg aagggcatcg acttcaagga ggacggcaac atcctggggc      600
acaagctgga gtacaactac aacagccaca acgtctatat catggccgac aagcagaaga      660
acggcatcaa ggtgaacttc aagatccgcc acaacatcga ggacggcagc gtgcagctcg      720
ccgaccacta ccagcagaac acccccatcg gcgacggccc cgtgctgctg cccgacaacc      780
actacctgag ctaccagtcc gccctgagca agacccccaa cgagaagcgc gatcacatgg      840
tcctgctgga gttcgtgacc gccgccggga tcactctcgg catggacgag ctgtacaagt      900
aaagcggccg cgactctaga tcataatcag ccataccaca tttgtagagg ttttacttgc      960
tttaaaaaac ctcccacacc tccccctgaa cctgaaacat aaaatgaatg caattgttgt     1020
tgttaacttg tttattgcag cttataatgg ttacaaataa agcaatagca tcacaaattt     1080
cacaaataaa gcattttttt cactgcattc tagttgtggt ttgtccaaac tcatcaatgt     1140
atcaagctta tcgatacgcg tacggcgcgc ctaggccggc cgatctcgcg cgccaaaagc     1200
ttctgtctct ctttctgtaa taaactaacg atttataaag tataaaatgt cgtaatgttt     1260 attttttggca acatgagttt aattcgaaat tgaatcaaac acaataaaaa aaagttaaaa     1320
ggttaaaatc attatattac atcattaatt cgaattatcg ttaatatgga tcaatttgaa     1380
cagttgatta acgtgtctct gctcaagtct ttgatcaaaa cgcaaatcga cgaaaatgtg     1440
tcggacaata tcaagtcgat gagcgaaaaa ctaaaaaggc tagaatacga caatctcaca     1500
gacagcgttg agatatacgg tattcacgac agcaggctga ataataaaaa aattagaaac     1560
tattatttaa ccctagaaag ataatcatat tgtgacgtac gttaaagata atcatgcgta     1620
aaattgacgc atgtgtttta tcggtctgta tatcgaggtt tatttattaa tttgaataga     1680
tattaagttt tattatattt acacttacat actaataata aattcaacaa acaatttatt     1740
tatgtttatt tatttattaa aaaaaaacaa aaactcaaaa tttcttctat aaagtaacaa     1800
aactttaaaa cattctctct tttacaaaaa taaacttatt ttgtacttta aaaacagtca     1860
tgttgtatta taaaataagt aattagctta acttatacat aatagaaaca aattatactt     1920
attagtcagt cagaaacaac tttggcacat atcaatatta tgctctcgac aaataacttt     1980
tttgcatttt ttgcacgatg catttgcctt tcgccttatt ttagaggggc agtaagtaca     2040
gtaagtacgt tttttcatta ctggctcttc agtactgtca tctgatgtac caggcacttc     2100
atttggcaaa atattagaga tattatcgcg caaatatctc ttcaaagtag gagcttctaa     2160
acgcttacgc ataaacgatg acgtcaggct catgtaaagg tttctcataa attttttgcg     2220
actttggacc ttttctccct tgctactgac attatggctg tatataataa agaatttat      2280 gcaggcaatg tttatcattc cgtacaataa tgccataggc cacctattcg tcttcctact     2340
gcaggtcatc acagaaacaca tttggtctag cgtgtccact ccgcctttag tttgattata     2400
atacataacc atttgcggtt taccggtact ttcgttgata gaagcatcct catcacaaga     2460
tgataataag tataccatct tagctggctt cggtttatat gagacgagag taaggggtcc     2520
gtcaaaacaa aacatcgatg ttcccactgg cctggagcga ctgttttca gtacttccgg      2580 tatctcgcgt tgtttgatc gcacggttcc cacaatggta attcgagctc gcccggggat      2640
ctaattcaat tagagactaa ttcaattaga gctaattcaa ttaggatcca gcttatcga      2700
```

```
tttcgaaccc tcgaccgccg gagtataaat agaggcgctt cgtctacgga gcgacaattc    2760
aattcaaaca agcaaagtga acacgtcgct aagcgaaagc taagcaaata aacaagcgca    2820
gctgaacaag ctaaacaatc ggggtaccgc tagagtcgac ggtaccgcgg gcccgggatc    2880
caccggtcgc caccatggtg cgctcctcca agaacgtcat caaggagttc atgcgcttca    2940
aggtgcgcat ggagggcacc gtgaacggcc acgagttcga gatcgagggc gagggcgagg    3000
gccgccccta cgagggccac aacaccgtga agctgaaggt gaccaagggc ggccccctgc    3060
ccttcgcctg gacatcctg tccccccagt tccagtacgg ctccaaggtg tacgtgaagc    3120
accccgccga catccccgac tacaagaagc tgtccttccc cgagggcttc aagtgggagc    3180
gcgtgatgaa cttcgaggac ggcggcgtgg tgaccgtgac ccaggactcc tccctgcagg    3240
acggctgctt catctacaag gtgaagttca tcggcgtgaa cttcccctcc gacggccccg    3300
taatgcagaa gaagaccatg ggctggaggg cctccaccga gcgcctgtac ccccgcgacg    3360
gcgtgctgaa gggcgagatc cacaaggccc tgaagctgaa ggacggcggc cactacctgg    3420
tggagttcaa gtccatctac atggccaaga agcccgtgca gctgcccggc tactactacg    3480
tggactccaa gctggacatc acctcccaca acgaggacta caccatcgtg gagcagtacg    3540
agcgcaccga gggcgccac cacctgttcc tgtagcggcc gcgactctag atcataatca    3600
gccataccac atttgtagag gttttacttg ctttaaaaaa cctcccacac ctccccctga    3660
acctgaaaca taaaatgaat gcaattgttg ttgttaactt gtttattgca gcttataatg    3720
gttacaaata aagcaatagc atcacaaatt tcacaaataa agcatttttt tcactgcatt    3780
ctagttgtgg tttgtccaaa ctcatcaatg tatcaagctt atcgatacgc gtacggcgcg    3840
aattcatttg ggaagtttgt gggtctattt tttaaacttt atatgaatgt tgtttagtt    3900 aatttaataa aggatatcga acagtatgcc agttttggta tttagccaat tggagatgtt    3960
cgatgagatg ttcgaactgc aaccgagttc gaggttccaa cacgactgtt atacgggttc    4020
cagccttcaa gttctacaga acaagtccac gagcgccaca cacagtccac agtccacact    4080
ccactccgct cggcgtggaa gccattcgct tcgtggcgaa gtgtttgttt atccagttga    4140
cagtttgtgg aaaatcgtca cggtgagcgg atcaaacgcg gaaaacgaac gcggacgaac    4200
ggcgagaaaa gcgaggaaaa acgggtgcag agacagagac tgattgggaa atatgtgcgc    4260
ctgagttttc ccggccagaa ggcaaagtgc caaatgctct gacaaataat tcctgtaata    4320
atcagcgcga ttgaaatcaa cgcgacgctc gtaaaattgc aaatgcagcg caaaaagtga    4380
acagcagtgc agcggaaatt aaatcgtttt agcgagtgcc aaacgggaaa tagaaaatcg    4440
gcagagtagc cgaactgcag ttaaaactat ctcttcctct tattgcgact aaacaaccgg    4500
cggattaatc gaatccgaaa gatggccccc aacttgctaa caatcggatt acttttgacc    4560
ctgatcgcca gcgtcaggc ccatctcaat attttcctca acttgcacga ggtgctgcgc    4620
ctaatcggta agtaatcgtg ttgattttcg cctgccttt ggcttttcaa ttaactgggc    4680
aattatttgc cactttgtgt gcgttcgttc gactttaaat caaatttgat ttatgccaag    4740
ccgggatttt gtctcctggg caaacgaatg cgacttgctg ggattattta ctctttttgc    4800
gtaaataata tatgccttt aattgttct agcctcggag ctacatataa agtagtattg    4860
tccctccttc aattggccag ctcaccgaga aacaagaaaa cattctattt gtctagcatg    4920
atttcctgtt tctttgattt aattgttcgt tagacttatc tagataaata gaaatgctaa    4980
agcgatttaa atttgtattt ctttgcgtta aattaaattc gattggcaag tggattcatc    5040
```

```
tctagataag taatccctct ataatcaaag ttttttattta aaaaatcata tttttttcata    5100
gtttatccaa tttaaaacaa tacaaaacaa ttttagatat attttataaa cgtcttcaaa    5160
agaaaataaa tagtaaaatc atgtagtcaa aaaatgacac caaatgagt atttaaatat     5220
ttagtttagt ttagtttata ttatttattt agcctaacta ttttccatag aagaatacta    5280
ctctaataag cttggggtac ccggggatct tgaagttcct attccgaagt tcctattctt    5340
caaatagtat aggaacttca gatccgaccg cggacatgta cagagctcga gaagtactag    5400
tggccacgtg ggccgtgcac cttaagcttg gcactggccg tcgttttaca acgtcgtgac    5460
tgggaaaacc ctggcgttac ccaacttaat cgccttgcag cacatccccc tttcgccagc    5520
tggcgtaata gcgaagaggc ccgcaccgat cgcccttccc aacagttgcg cagcctgaat    5580
ggcgaatggc gcctgatgcg gtattttctc cttacgcatc tgtgcggtat ttcacaccgc    5640
atacgtcaaa gcaaccatag tacgcgccct gtagcggcgc attaagcgcg gcgggtgtgg    5700
tggttacgcg cagcgtgacc gctacacttg ccagcgccct agcgcccgct cctttcgctt    5760
tcttcccttc ctttctcgcc acgttcgccg gctttccccg tcaagctcta atcgggggc     5820
tccctttagg gttccgattt agtgctttac ggcacctcga ccccaaaaaa cttgatttgg    5880
gtgatggttc acgtagtggg ccatcgccct gatagacggt ttttcgccct tgacgttgg    5940
agtccacgtt ctttaatagt ggactcttgt tccaaactgg aacaacactc aaccctatct   6000
cgggctattc ttttgattta tagggatttt gccgatttc ggcctattgg ttaaaaaatg    6060
agctgattta acaaaaattt aacgcgaatt ttaacaaaat attaacgttt acaattttat    6120
ggtgcactct cagtacaatc tgctctgatg ccgcatagtt aagccagccc cgacacccgc    6180
caacacccgc tgacgcgccc tgacgggctt gtctgctccc ggcatccgct tacagacaag    6240
ctgtgaccgt ctccgggagc tgcatgtgtc agaggttttc accgtcatca ccgaaacgcg    6300
cgagacgaaa gggcctcgtg atacgcctat ttttataggt taatgtcatg ataataatgg    6360
tttcttagac gtcaggtggc acttttcggg gaaatgtgcg cggaaccct atttgtttat     6420
ttttctaaat acattcaaat atgtatccgc tcatgagaca ataaccctga taaatgcttc    6480
aataatattg aaaaaggaag agtatgagta ttcaacattt ccgtgtcgcc cttattccct    6540
tttttgcggc attttgcctt cctgtttttg ctcacccaga aacgctggtg aaagtaaaag    6600
atgctgaaga tcagttgggt gcacgagtgg gttacatcga actggatctc aacagcggta    6660
agatccttga gttttcgc cccgaagaac gttttccaat gatgagcact tttaaagttc       6720
tgctatgtgg cgcggtatta tcccgtattg acgccgggca agagcaactc ggtcgccgca    6780
tacactattc tcagaatgac ttggttgagt actcaccagt cacagaaaag catcttacgg    6840
atggcatgac agtaagagaa ttatgcagtg ctgccataac catgagtgat aacactgcgg    6900
ccaacttact tctgacaacg atcggaggac cgaaggagct aaccgctttt ttgcacaaca    6960
tgggggatca tgtaactcgc cttgatcgtt gggaaccgga gctgaatgaa gccataccaa    7020
acgacgagcg tgacaccacg atgcctgtag caatggcaac aacgttgcgc aaactattaa    7080
ctggcgaact acttactcta gcttcccggc aacaattaat agactggatg gaggcggata    7140
aagttgcagg accacttctg cgctcggccc ttccggctgg ctggtttatt gctgataaat    7200
ctggagccgg tgagcgtggg tctcgcggta tcattgcagc actggggcca gatggtaagc    7260
cctcccgtat cgtagttatc tacacgacgg ggagtcaggc aactatggat gaacgaaata    7320
gacagatcgc tgagataggt gcctcactga ttaagcattg gtaactgtca gaccaagttt    7380
actcatatat actttagatt gatttaaaac ttcattttta atttaaaagg atctaggtga    7440
```

```
agatccttt tgataatctc atgaccaaaa tcccttaacg tgagttttcg ttccactgag    7500
cgtcagaccc cgtagaaaag atcaaaggat cttcttgaga tccttttttt ctgcgcgtaa    7560
tctgctgctt gcaaacaaaa aaaccaccgc taccagcggt ggtttgtttg ccggatcaag    7620
agctaccaac tcttttccg aaggtaactg gcttcagcag agcgcagata ccaaatactg    7680
ttcttctagt gtagccgtag ttaggccacc acttcaagaa ctctgtagca ccgcctacat    7740
acctcgctct gctaatcctg ttaccagtgg ctgctgccag tggcgataag tcgtgtctta    7800
ccgggttgga ctcaagacga tagttaccgg ataaggcgca gcggtcgggc tgaacggggg    7860
gttcgtgcac acagcccagc ttggagcgaa cgacctacac cgaactgaga tacctacagc    7920
gtgagctatg agaaagcgcc acgcttcccg aagggagaaa ggcggacagg tatccggtaa    7980
gcggcagggt cggaacagga gagcgcacga gggagcttcc agggggaaac gcctggtatc    8040
tttatagtcc tgtcgggttt cgccacctct gacttgagcg tcgatttttg tgatgctcgt    8100
caggggggcg gagcctatgg aaaaacgcca gcaacgcggc cttttacgg ttcctggcct    8160 tttgctggcc ttttgctcac atgttctttc ctgcgttatc ccctgattct gtggataacc    8220
gtattaccgc ctttgagtga gctgataccg ctcgccgcag ccgaacgacc gagcgcagcg    8280
agtcagtgag cgaggaagcg gaagagcgcc caatacgcaa accgcctctc cccgcgcgtt    8340
ggccgattca ttaatgcagc tggcacgaca ggtttcccga ctggaaagcg ggcagtgagc    8400
gcaacgcaat taatgtgagt tagctcactc attaggcacc ccaggcttta cactttatgc    8460
ttccggctcg tatgttgtgt ggaattgtga gcggataaca atttcacaca ggaaacagct    8520
atgaccatga ttacgaattg atccaagctt atcgatttcg aaccctcgac cgccggagta    8580
taaatagagg cgcttcgtct acggagcgac aattcaattc aaacaagcaa agtgaaca    8638
```

<210> SEQ ID NO 4
<211> LENGTH: 67
<212> TYPE: DNA
<213> ORGANISM: Artificial Sequence
<220> FEATURE:
<223> OTHER INFORMATION: Description of Artificial Sequence: Synthetic
    FRT sequence

<400> SEQUENCE: 4

```
ttgaagttcc tattccgaag ttcctattct ctagaaagta taggaacttc agagcgcttt    60
tgaagct                                                              67
```

<210> SEQ ID NO 5
<211> LENGTH: 26
<212> TYPE: DNA
<213> ORGANISM: Artificial Sequence
<220> FEATURE:
<223> OTHER INFORMATION: Description of Artificial Sequence: Synthetic
    primer

<400> SEQUENCE: 5

```
gagcttaagg gtacccgggg atcttg                                         26
```

<210> SEQ ID NO 6
<211> LENGTH: 31
<212> TYPE: DNA
<213> ORGANISM: Artificial Sequence
<220> FEATURE:
<223> OTHER INFORMATION: Description of Artificial Sequence: Synthetic
    primer

<400> SEQUENCE: 6
gactagtcga tatctagggc cgcctagctt c                                          31

<210> SEQ ID NO 7
<211> LENGTH: 33
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 7
ttggcgcgcc aaaagcttct gtctctcttt ctg                                        33

<210> SEQ ID NO 8
<211> LENGTH: 35
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 8
cggggtaccc caagcttatt agagtagtat tcttc                                      35

<210> SEQ ID NO 9
<211> LENGTH: 31
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 9
ttggcgcgcc aaggggtacc cggggatctt g                                          31

<210> SEQ ID NO 10
<211> LENGTH: 46
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 10
ccgctcgagc ggaagatctg aagttcctat actatttgaa gaatag                          46

<210> SEQ ID NO 11
<211> LENGTH: 57
<212> TYPE: DNA
<213> ORGANISM: Artificial Sequence
<220> FEATURE:
<223> OTHER INFORMATION: Description of Artificial Sequence: Synthetic
      FRT sequence

<400> SEQUENCE: 11
ttgaagttcc tattccgaag ttcctattct caaatagta taggaacttc agagcgc               57

<210> SEQ ID NO 12
<211> LENGTH: 17
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 12
cggcgactga gatgtcc                                                  17

<210> SEQ ID NO 13
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 13
ccctagaaag atagtctgcg                                               20

<210> SEQ ID NO 14
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 14
atcagtgaca cttaccgcat tgaca                                         25

<210> SEQ ID NO 15
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 15
ccagagcgat acagaagaag c                                             21

<210> SEQ ID NO 16
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 16
tgttcagtgc agagactcgg                                               20

<210> SEQ ID NO 17
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 17
tatgagttaa atcttaaaag tcacg                                         25

<210> SEQ ID NO 18
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 18
gttgaattta ttattagtat gtaagtg                                       27

```
<210> SEQ ID NO 19
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 19
agaagaacgg catcaaggc                                                   19

<210> SEQ ID NO 20
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 20
actccaagct ggacatcacc                                                  20

<210> SEQ ID NO 21
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 21
cgcagacgaa gaacaaacag ta                                               22

<210> SEQ ID NO 22
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 22
gctgtttgct tgttgttgt cat                                               23

<210> SEQ ID NO 23
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 23
gggccacacg atttatggc                                                   19

<210> SEQ ID NO 24
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 24
gtttattttt ggcaacatga g                                                21
```